US006400487B1

(12) United States Patent
Harris et al.

(10) Patent No.: US 6,400,487 B1
(45) Date of Patent: Jun. 4, 2002

(54) METHOD AND APPARATUS FOR SCREENING CHEMICAL COMPOUNDS

(75) Inventors: Timothy D. Harris, Toms River; Richard L. Hansen, Pennington; William Karsh, Plainsboro; Neal A. Nicklaus, East Windsor; Jay K. Trautman, Pennington, all of NJ (US)

(73) Assignee: Praelux, Inc., Lawrenceville, NJ (US)

( * ) Notice: Subject to any disclaimer, the term of this patent is extended or adjusted under 35 U.S.C. 154(b) by 0 days.

(21) Appl. No.: 09/724,253

(22) Filed: Nov. 28, 2000

Related U.S. Application Data

(60) Division of application No. 09/333,749, filed on Jun. 15, 1999, which is a continuation of application No. 09/300,335, filed on Apr. 27, 1999, now abandoned, which is a continuation of application No. PCT/US99/05589, filed on Mar. 16, 1999, which is a continuation-in-part of application No. 09/042,527, filed on Mar. 16, 1998, now abandoned.

(51) Int. Cl.[7] .............................................. G02B 26/08
(52) U.S. Cl. ..................... 359/210; 359/823; 250/201.2
(58) Field of Search ........................ 359/210, 823–824, 359/900, 490, 495, 629, 634; 250/201.2–201.5

(56) References Cited

U.S. PATENT DOCUMENTS

| | | | |
|---|---|---|---|
| 4,000,252 A | 12/1976 | Kosak | 424/1 |
| 4,271,139 A | 6/1981 | Hart | 424/1 |
| 4,447,546 A | 5/1984 | Hirschfeld | 436/527 |
| 4,538,299 A | 8/1985 | DeForest | 382/21 |
| 4,568,649 A | 2/1986 | Bertoglio-Matte | 436/534 |
| 4,582,809 A | 4/1986 | Block et al. | 436/527 |
| 4,844,617 A | 7/1989 | Kelderman et al. | 356/372 |
| 5,054,926 A | 10/1991 | Dabbs et al. | 356/345 |
| 5,091,652 A | 2/1992 | Mathies et al. | 250/458.1 |
| 5,099,521 A | 3/1992 | Kosaka | 382/6 |
| 5,107,422 A | 4/1992 | Kamentsky et al. | 364/413.08 |
| 5,132,526 A | 7/1992 | Iwasaki | 250/201.3 |
| 5,142,517 A * | 8/1992 | Takahashi | 250/201.5 |
| 5,242,797 A | 9/1993 | Hirschfeld | 435/6 |
| 5,248,876 A | 9/1993 | Kerstens et al. | 250/561 |
| 5,304,810 A | 4/1994 | Amos | 250/458.1 |
| 5,355,215 A | 10/1994 | Schroeder et al. | 356/317 |
| 5,375,175 A | 12/1994 | Kino et al. | 382/8 |
| 5,377,001 A | 12/1994 | Malin et al. | 356/237 |
| 5,452,125 A | 9/1995 | White et al. | 359/368 |
| 5,465,147 A | 11/1995 | Swanson | 356/345 |
| 5,491,084 A | 2/1996 | Chalfie et al. | 435/189 |
| 5,547,849 A | 8/1996 | Baer et al. | 435/7.24 |
| 5,556,764 A | 9/1996 | Sizto et al. | 435/7.24 |
| 5,561,554 A | 10/1996 | White et al. | 359/368 |
| 5,659,384 A | 8/1997 | Ina | 355/53 |

(List continued on next page.)

FOREIGN PATENT DOCUMENTS

| | | |
|---|---|---|
| EP | 0 871 052 A1 | 10/1998 |
| WO | WO 98/38490 | 9/1998 |
| WO | WO 98/45704 | 10/1998 |
| WO | WO 98/55866 | 12/1998 |

OTHER PUBLICATIONS

Richard V. Johnson, "Focus error detection in optical data storage systems," *SPIE vol. 200 Laser Recording and Information Handling*, pp. 73–78 (Aug. 1979).

(List continued on next page.)

Primary Examiner—James Phan
(74) Attorney, Agent, or Firm—Fish & Neave; James F. Haley, Jr.; Kevin T. Roddy

(57) ABSTRACT

Methods and apparatus for screening large numbers of chemical compounds and performing a wide variety of fluorescent assays, including live cell assays. The methods utilize a laser linescan confocal microscope with high speed, high resolution and multi-wavelength capabilities and real time data-processing. Imaging may be done at video-rates and with use of ultraviolet illumination.

29 Claims, 28 Drawing Sheets

U.S. PATENT DOCUMENTS

| | | | |
|---|---|---|---|
| 5,661,035 A | 8/1997 | Tsien et al. | 436/63 |
| 5,665,543 A | 9/1997 | Foulkes et al. | 435/6 |
| 5,665,562 A | 9/1997 | Cook | 435/35 |
| 5,687,251 A | 11/1997 | Erler et al. | 382/133 |
| 5,760,901 A | 6/1998 | Hill | 356/345 |
| 5,844,598 A | 12/1998 | Janesick | 348/79 |
| 5,848,177 A | 12/1998 | Bauer et al. | 382/128 |
| 5,876,946 A | 3/1999 | Burbaum et al. | 435/7.1 |
| 5,889,881 A | 3/1999 | MacAulay et al. | 382/133 |
| 5,915,048 A | 6/1999 | Hill et al. | 382/255 |
| 5,989,835 A | 11/1999 | Dunlay et al. | 435/7.2 |

OTHER PUBLICATIONS

Charles J. Koester, "Scanning Mirror Microscope With Optical Sectioning Characteristics: Applications in Opthalmology," *Applied Optics,* 19(11), pp. 1749–1757 (1980).

Donald K. Cohen, Wing Ho Gee, M. Ludeke, and Julian Lewkowicz, "Automatic focus control: the astigmatic lens approach," *Applied Optics,* 23(4), pp. 565–570 (1984).

G.J. Brakenhoff, H.T.M. van der Voort, E.A. van Spronsen, W.A.M. Linnesmans, and N. Nanninga, "Three–Dimensional Chromatin Distribution in Neuroblastoma Nuclei Shown by Confocal Scanning Laser Microcsopy," *Nature,* 317, pp. 748–749 (1985).

Roger Y. Tsien and Martin Poenie, "Fluorescence ratio imaging: a new window into intracellular ionic signaling," *Trends in Biochemical Science,* 11, pp. 450–455 (Nov. 1986).

J.G. White, W.B. Amos, and M. Fordham, "An Evaluation of Confocal Versus Conventional Imagining of Biological Structures by Fluorescence Light Microscopy," *The Journal of Cell Biology,* 105, pp. 41–48 (1987).

Stephen C. Baer, "Tandem scanning slit microscopy," *SPIE vol. 1139 Optical Storage and Scanning Technology,* pp. 99–101 (1989).

Jeff W. Lichtman, William J. Sunderland, Robert S. Wilkinson, "High–Resolution Imaging of Synaptic Structure With a Simple Confocal Microscope," *The New Biologist,* 1(1), pp. 75–82 (1989).

D.H. Burns, R.B. Hatangadi, F.A. Spelman, "Scanning Slit Aperture Confocal Microscopy for Three–Dimensional Imaging," *J. Scanning Microscopy,* 12, pp. 156–160 (1990).

Bonita F. Bowman, Julian A. Peterson, and James T. Stull, "Pre–steady–state Kinetics of the Activation of Rabbit Skeletal Muscle Myosin Light Chain Kinase by $Ca^{2+}$/Calmodulin," *J. Biol. Chem.,* 267(8), pp. 5346–5354 (1992).

G.J. Brakenhoff and K. Visscher, "Imaging modes for bilateral confocal scanning microscopy," *J. of Microscopy,* 171(1), pp. 17–26 (1993).

David R. Sandison and Watt W. Webb, "Background Rejection and Signal–to–noise Optimization in Confocal and Alternative Fluorescence Microscopes," *Applied Optics,* 33(4), pp. 603–615 (1994).

W.B. Amos and J.G. White, "Direct View Confocal Imaging Systems Using a Slit Aperture," *Handbook of Biological Confocal Microscopy,* pp. 403–415, ed. James B. Pawley, Plenum Press, New York (1995).

Roger Y. Tsien and Brian J. Bacskai, "Video–Rate Confocal Miscropy," *Handbook of Biological Confocal Microscopy,* pp. 459–478, ed. James B. Pawley, Plenum Press, New York (1995).

Charles J. Koester, "Comparison of Various Optical Sectioning Methods: The Scanning Slit Confocal Microscope," *Handbook of Biological Confocal Microscopy,* pp. 525–534, ed. James B. Pawley, Plenum Press, New York (1995).

D. R. Sandison, D.W. Piston, R.M. Williams and W. W. Webb, "Quantitative Comparison of Background Rejection, Signal–to–noise Ratio, and Resolution in Confocal and Full–field Laser Scanning Microcsopes," *Applied Optics,* 34(19), pp. 3576–3588 (1995).

David M. Shotton, "Electronic light microscopy:present capabilities and future prospect," *Histochem. and Cell Biol.,* 104(2), pp. 97–137 (1995).

Hakan Ancin, Badrinath Roysam, Thomas E. Dufresne Matthew M. Chestnut, Gregg M. Ridder, Donald H. Szarowski and James N. Turner, "Advances in Automated 3–D Image Analysis of Cell Populations Imaged by Confocal Microscopy," *Cytometry,* 25, pp. 221–235 (1996).

James R. Broach & Jeremy Thorner, "High–Throughput Screening for Drug Discovery," *Nature,* 384, pp. 14–16 (1996).

Frans H.M.M. van de Put and Austin C. Elliott, "Imaging of Intracellular Calcium Stores in Individual Permeablized Pancreatic Acinar Cells," *J. Biol. Chem.,* 271(9), pp. 4999–5006 (1996).

Joseph G. Hacia, Lawrence C. Brody, Mark S. Chee, Stephen P.A. Fodor & Francis S. Collins, "Detection of Heterozygous Mutations in BRCA1 Using High Density Oligonucleotide Arrays and Two–Color Fluorescence Analysis," *Nature Genetics,* 14, pp. 441–447 (1996).

David J. Lockhart, Helin Dong, Michael C. Byrne, Maximillian T. Follettie, Michael V. Gallo, Mark S. Chee, Michael Mittman, Chunwei Wang, Michiko Kobayashi, Heidi Horton, and Eugene L. Brown, "Expressing Monitoring By Hybridization to High–Density Oligonucleotide Arrays," *Nature Biotechnology,* 14, pp. 1675–1680 (1996).

Te–Tuan Yang, Steven R. Kain, Paul Kitts, Anu Kondepudi, Mary M. Yang and Douglas C. Youvan, "Dual color microscopic imagery of cells expressing the green fluorescent protein and a red–shifted variant," *Gene,* 173, pp. 19–23 (1996).

"Scintillation Proximity Assay," *1996 Amersham Life Science Catalog,* pp. 252–258.

Editorial, "To Affinity . . . and Beyond," Nature Genetics, 14, pp. 367–0370 (1996).

Kenneth A. Giuliano, Robbin L. Debiasio, R. Terry Dunlay, Albert Gough, Joanne M. Volosky, Joseph Zock, George N. Pavlakis, and D. Lansing Taylor, "High–Content Screening: A New Approach to Easing Key Bottlenecks in the Drug Discovery Process," *J. of Biomolecular Screening,* 2(4), pp. 249–259 (1997).

Jesus E. Gonzalez and Roger Y. Tsien, "Improved indicators of cell membrane potential that use fluorescence resonance energy transfer," *Chemistry and Biology,* 4(4), pp. 269–277 (1997).

Markus Hoth, Christopher M. Fanger, and Richard S. Lewis, "Mitochondrial Regulation of Store–operated Calcium signaling in T Lymphocytes," *J. Cell Biology,* 137(3), pp. 633–648 (1997).

Steven D. Kahl, Frederick R. Hubbard, G. Sitta Sittampalam, and Joseph M. Zock, "Validation of a High Throughput Scintillation Proximity Assay for 5–Hydroxytryptamine Receptor Binding Activity," *Journal of Biomolecular Screening,* 2(1), pp. 33–40 (1997).

Yasutaka Kakinoki, Jeremy Somers and David L. Brautigan, "Multisite Phosphorylation and the Nuclear Localization of Phosphatase Inhibitor 2–Green Fluorescent Protein Fusion Protein during S Phase of the Cell Growth Cycle," *J. Biol. Chem.,* 272(51), pp. 32308–32314 (1997).

Atsushi Miyawaki Juan Llopis, Roger Helm, J. Michael McCaffery, Joseph A. Adfams, Mitsuhiko Ikura, and Roger Y. Tsien, "Fluorescent $Ca^{2+}$ based on green fluorescent proteins and calmodulin," *Nature,* 388, pp. 882–887 (1997).

Hideo Mogami, Chris Lloyd Mills and David V. Gallacher, "Phopholipase C inhibitor, U72122, releases intracellular $Ca^{2+}$, potentiates $Ins(1,4,5)$ $P_3$–mediated $Ca^{2+}$ release and directely activates ion channels in mouse pancreatic acinar cells," *Biochem. J.,* 324, pp. 645–651 (1997).

D.D. Mosser, A.W. Caron, L. bourget, P. Jolicouer and B. Massie, "Use of a Dicistronic Expression Cassette Encoding the Green Fluorescent Protein for the Screening and Selection of Cells Expressing Inducible Gene Products," *BioTechniques,* 22(1), pp. 150–161 (1997).

R.R. Muldoon, J.P. Levy, S.R. Kain, P.A. Kitts and C.J. Link Jr., "Tracking and Quantiation of Retroviral Mediated Transfer Using a Completely Humanized, Red–Shifted Green Fluorescent Protein Gene," *BioTechniques,* 22(1), pp. 162–167 (1997).

Ian Parker, Nick Callamaras, W. Gil Wier, "A high–resolution, confocal laser–scanning microscope and flash photolysis system for physiological studies," *Cell Calcium,* 21(6), pp. 441–452 (1997).

Tullio Pozzan, "Calcium turns turquoise into gold," *Nature,* 388, pp. 834–835 (1997).

Micah S. Siegel and Ehud Y. Isacoff, "A Genetically Encoded Optical Probe of Membrane Voltage," *Neuron,* 19, pp. 735–741 (1997).

Frans H.M.M. van de Put and Austin C. Elliott, "The Endoplasmic Reticulum Can Act as a Functional $CA^{2+}$ Store in All Subcellular Regions of the Pancreatic Acinar Cell," *J. Biol. Chem.,* 272(4), pp. 27764–27770 (1997).

"Flashplate Products for High Throughput Screening and Other Assays," *NEN Life Science Products 1997 Research Products Catalog,* pp. C3–C13.

"Elisa," DOC. NO. T1306, *Peirce Chemical Technical Library,* (uploaded and last modified Jun. 1997) <http://www.piercenet.com/Lib>.

Robert P. Bennett, Cindy A. Cox and James P. Hoeffler, "Fusion of Green Fluorsecent Protein with the Zeocin™–Resistant Marker Allows Visual Screening and Drug Selection of Transfected Eukaryotic Cells," *BioTechniques,* 24(3), pp. 478–482 (1998).

Michael J. Berridge, Martin D. Bootman and Peter Lipp, "Calcium—a life and death signal," *Nature,* 395, pp. 645–648 (1998).

Andrzej Deptala, Elzbieta Bedner, Wojciech Gorczyca and Zbigniew Darzynkiewicz, "Activation of Nuclear Factor Kappa B (NF–κB) Assayed by Laser Scanning Cytometry (LSC)," *Cytometry,* 33, pp. 376–382 (1998).

Earnshaw, "Evaluation of Flashplate in a Helicase Assay," *NEN Life Science Products,* (visited Jun. 15, 1998) <http://www.NENlifesci.com/fn025.htm>.

Gloria J.F. Ding, Paul a. Fischer, Robert C. Boltz, Jack A. Schmidt, James J. Colaianne, Albert Gough, Richard A. Rubin and Douglas K. Miller, "Characterization and Quantitation of NF–κB Nuclear Translocation Induced by Interleukin–1 and Tumor Necrosis Factor–α," *J. Biol. Chem.,* 44, pp. 28897–28905 (1998).

Earnshaw, "Evaluation of Flashplate in a Helicase Assay," *NEN Life Science Products,* (visited Jun. 15, 1998) <http://www.NENlifesci.com/fn025.htm>.

Gero Miesenbock, dino A. De Angelis and James E. Rothman, "Visualising secretion and synaptic transmission with pH–sensitive green fluorescent proteins," *Nature,* 394, pp. 192–195 (1998).

Xaio–Ping Sun, Nick Callamaras, Jonathan S. Marchant and Ian Parker, A continuum of $InsP_3$–mediated elementary $Ca^{2+}$ signalling events in Xenopus oocytes, *J. Physiology,* 509.1, pp. 67–80 (1998).

Roger Y. Tsien and Atsushi Miyawaki, "Seeing the Machinery of Live Cells," *Science,* 280, pp. 1954–1955 (1998).

"Flashplate Products and Applications," *NEN Life Science Products,* (visited Jun. 15, 1998) <http://www.NENlifesci.com/p_srv_14.htm#77>.

"Overview of Flashplate," *NEN Life Science Products,* (visited Jun. 15, 1998) <http://www.NENlifesci.com/p_srv_13.htm#74>.

David K. Hanzel, John Q. Trojanowski, Richard F. Johnston, and Jeanne F. Loring, "High–throughput quantitative histological analysis of Alzheimer's disease pathology using a confocal digital microscanner," *Nature Biotechnology,* 17, pp. 53–57, (1999).

Tim Harris, Jay Trautman and Rich Hansen, "Rapid Confocal Imaging: A High Sensitivity, High Throughput Method for Drug Discovery," Mar. 5, 1999, "Miniaturization Technologies" Conference sponsored by IBC.

* cited by examiner

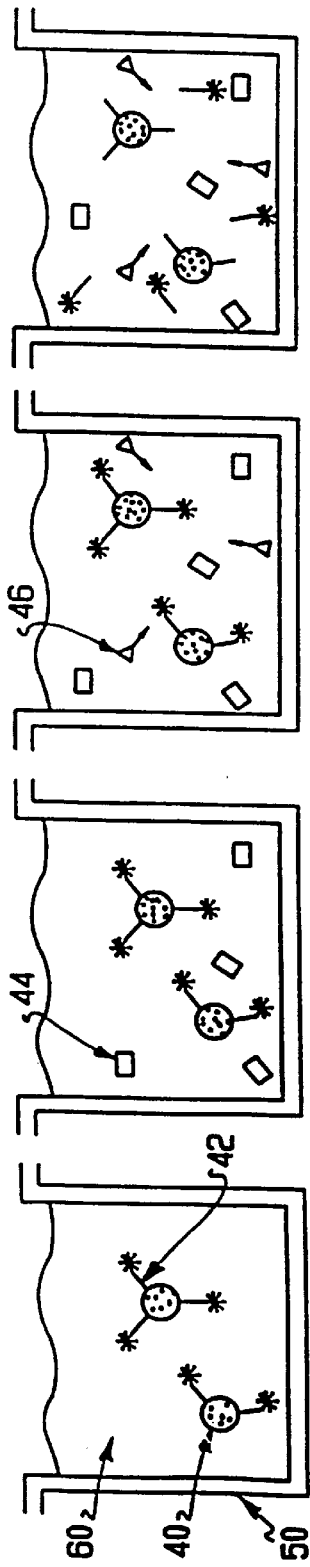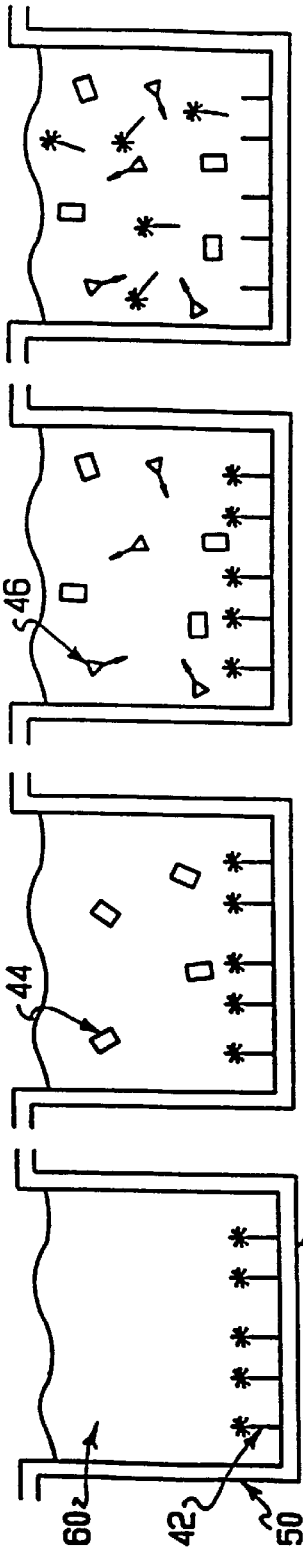

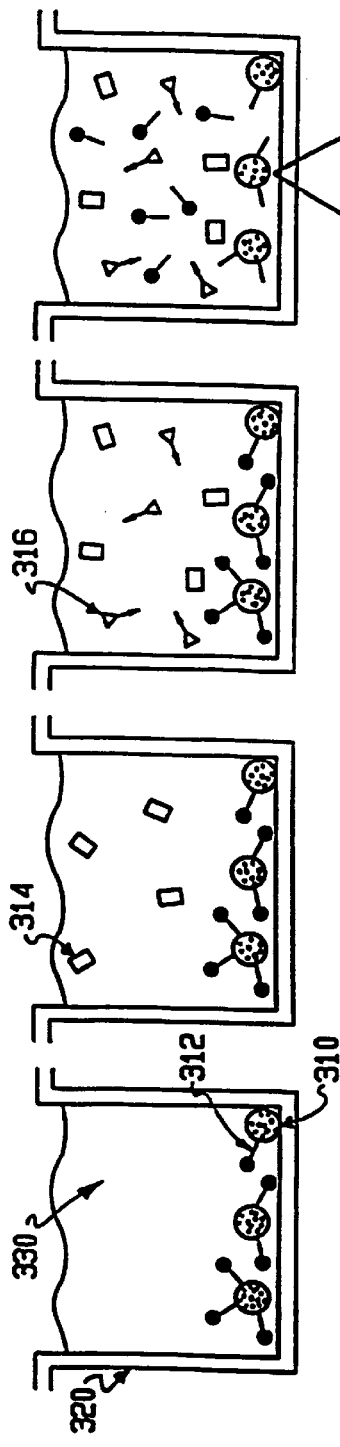
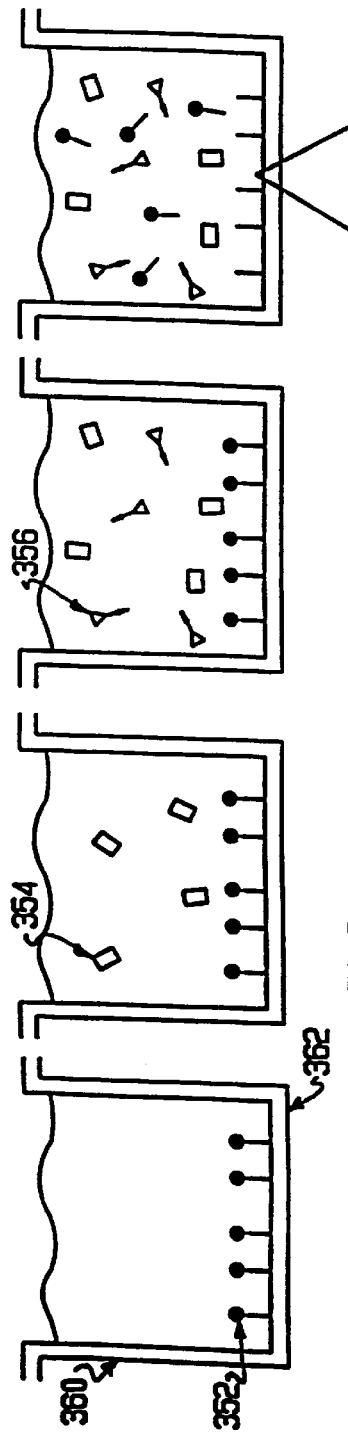

Texas Red Labeled Antibody
(No Activation)

Hoechst Overlay

Texas Red Labeled Antibody
(with Activation)

Hoechst Overlay

Threshold the Hoechst Nuclear Marker Image to Create a Binary Mask.

Erode Mask to Capture Inner Nuclei Intensity.

Dilate Mask for Cytoplasmic Intensity.

Apply Annular and Eroded Masks to Transcription Factor Image and Measure Respective Intensities.

Pre-Injection t = 0 s 1.2 s 2.4 s 3.6 s 4.8 s 6.0 s 7.2 s 8.4 s 9.6 s 10.8 s 12.0 s 13.2 s 14.4 s 15.6 s 0 Seconds 0.6 Seconds 3.0 Seconds 5.4 Seconds 7.8 Seconds 10.2 Seconds 12.6 Seconds 15.0 Seconds Fluorescein Labeled Peptide Ligand 20nM LDS 751 Cytoplasm Stain Generated Mask Overlay of A and B Showing Variable Receptor Activity 256 nM Ligand Scaled 200 – 400
Counts Full Scale.

256 nM Ligand with 1 µM
Hoechst Overlay.

256 nM Ligand with 10 µM
Competitor Scaled 200 – 400
Counts Full Scale.

256 nM Ligand with 10 µM
Competitor and 1 uM Hoechst
Overlay.

Unlabeled Beads

17 Fluors/Bead

170 Fluors/Bead

1700 Fluors/Bead
(Scale Reduced 10x)

METHOD AND APPARATUS FOR SCREENING CHEMICAL COMPOUNDS

This is a divisional of application Ser. No. 09/333,749, filed Jun. 15, 1999, which is a continuation of application Ser. No. 09/300,335, filed Apr. 27, 1999, now abandoned, which is a continuation of international application PCT/US99/05589, filed Mar. 16, 1999, which designated the United States and which is a continuation-in-part of application Ser. No. 09/042,527, filed Mar. 16, 1998, now abandoned.

FIELD OF THE INVENTION

The present invention relates to methods and apparatus for identifying pharmacological agents useful for the diagnosis and treatment of disease by performing a variety of assays on cell extracts, cells or tissues where the measurement of biological activity involves the use of various embodiments of a line-scan confocal imaging system and associated data processing routines.

BACKGROUND OF THE INVENTION

There is currently a need in drug discovery and development and in general biological research for methods and apparatus for accurately performing cell-based assays. Cell-based assays are advantageously employed for assessing the biological activity of chemical compounds and the mechanism-of-action of new biological targets. In a cell-based assay, the activity of interest is measured in the presence of both competing and complementary processes. As pertains to chemical compound screening, information is available as to the specific activity of the compound. For example, it is possible to assess not only whether a compound binds the target of the assay, but also whether it is an agonist or an antagonist of the normal activity of the target. Frequently, the target is a cell-surface receptor. In some signaling pathways, the member of the pathway of greatest potential therapeutic value is not the receptor but an intracellular signaling protein associated with the receptor. It is, therefore, desirable to develop methods to assay activity throughout the pathway, preferably in the cellular milieu.

In addition, there is a need to quickly and inexpensively screen large numbers of chemical compounds. This need has arisen in the pharmaceutical industry where it is common to test chemical compounds for activity against a variety of biochemical targets, for example, receptors, enzymes and nucleic acids. These chemical compounds are collected in large libraries, sometimes exceeding one million distinct compounds. The use of the term chemical compound is intended to be interpreted broadly so as to include, but not be limited to, simple organic and inorganic molecules, proteins, peptides, nucleic acids and oligonucleotides, carbohydrates, lipids, or any chemical structure of biological interest.

In the field of compound screening, cell-based assays are run on collections of cells. The measured response is usually an average over the cell population. For example, a popular instrument used for ion channel assays is disclosed in U.S. Pat. No. 5,355,215. A typical assay consists of measuring the time-dependence of the fluorescence of an ion-sensitive dye, the fluorescence being a measure of the intra-cellular concentration of the ion of interest which changes as a consequence of the addition of a chemical compound. The dye is loaded into the population of cells disposed on the bottom of the well of a multiwell plate at a time prior to the measurement. In general, the response of the cells is heterogeneous in both magnitude and time. This variability may obscure or prevent the observation of biological activity important to compound screening. The heterogeneity may arise from experimental sources, but more importantly, heterogeneity is fundamental in any population of cells. Among others, the origin of the variability may be a consequence of the life-cycle divergence among the population, or the result of the evolutionary divergence of the number of active target molecules. A method that mitigates, compensates for, or even utilizes the variations would enhance the value of cell-based assays in the characterization of the pharmacological activity of chemical compounds.

Quantification of the response of individual cells circumvents the problems posed by the non-uniformity of that response of a population of cells. Consider the case where a minor fraction of the population responds to the stimulus. A device that measures the average response will have less sensitivity than one determining individual cellular response. The latter method generates a statistical characterization of the response profile permitting one to select the subset of active cells. Additional characterization of the population will enhance the interpretation of the response profile.

Various measurement devices have been used in the prior art in an attempt to address this need. Flow-cytometer-based assays are widely practiced and measure cell properties one at a time by passing cells through a focused laser beam. Several disadvantages accompany this method. Most important to the pharmaceutical industry is that assays can not readily be performed on compounds disposed in microtiter plates. In addition, the throughput is poor, typically 10–100 seconds per sample, the observation time of each cell is <1 ms, prohibiting kinetic assays, and finally, only the cell-averaged signal can be determined.

In addition, many assays require determination of the relative locations of the fluorescence signals. Devices called scanning cytometers, as disclosed in U.S. Pat. No. 5,107,422 and U.S. Pat. No. 5,547,849, are widely used for imaging single cells. In order to gain acceptable speed, these devices operate at low (~5–10 $\mu$m) resolution. Thus, these devices offer little advantage over flow cytometers for assays requiring spatial information on the distribution of the fluorescence signals.

An additional alternative technology is the fast-camera, full-field microscope. These devices have the ability to obtain images at a resolution and speed comparable to the present invention, on certain samples. However, they are not confocal and are consequently susceptible to fluorescence background and cannot be used to optically section the sample. In addition, simultaneous, multi-parameter data is not readily obtained.

In contrast to the prior art, the present invention can be used to perform multi-parameter fluorescence imaging on single cells and cell populations in a manner that is sufficiently rapid and versatile for use in compound screening. Methods and apparatus are provided for obtaining and analyzing both the primary response of individual cells and additional measures of the heterogeneity of the sample population. In addition, the locations of these multiple fluorophores can be determined with sub-cellular resolution. Finally, the present invention can be used to image rapidly changing events at video-rates. Together these capabilities enable new areas of research into the mechanism-of-action of drug candidates.

The present invention may also be employed in an inventive fluorescence-based biochemical assay, somewhat analogous to the surface scintillation assay ("SSA") which is among the more widely used methods for screening chemical compounds.

FIGS. 1(a)–1(f) depict the steps of a receptor-binding SSA. In FIG. 1(a), soluble membranes 10 with chosen receptors 12 are added to a well 20 containing a liquid 30. These membranes are isolated from cells expressing the receptors. In FIG. 1(b), radio-labeled ligands 14 are added to the well. The ligand is known to have a high binding affinity for the membrane receptors. The most common radio labels are $^3$H, $^{35}$S, $^{125}$I, $^{33}$P and $^{32}$P. In FIG. 1(c), beads 16 are added to the well. The beads are coated with a material, such as wheat germ agglutinin, to which the membranes strongly adhere. The beads have a diameter of 3–8 µm and are made of plastic doped with a scintillant. Alternatively, the order of the operations depicted in FIGS. 1(b) and 1(c) may be interchanged.

The radiolabels decay by emitting high energy electrons, or beta particles, which travel approximately 1–100 µm before stopping, depending on the radio-isotope. If the radiolabels are bound to the membranes attached to the beads, the beta particles may travel into the beads and cause bursts of luminescence. If the radio-labels are dispersed throughout the liquid, the emitted beta particles will not generally excite luminescence in the beads. In FIG. 1(d), the luminescence of the beads caused by decay of the radio labels is detected. In FIG. 1(e), a test compound 18 is added to the well. The purpose of the assay is to determine the extent to which this compound will displace the radio-labeled ligands. If radio-labeled ligands are displaced and diffuse into the liquid, the luminescence of the beads will be reduced. In FIG. 1(f), the luminescence of the beads is again detected. By measuring the reduction in luminescence, the activity of the test compound can be determined.

FIGS. 2(a)–2(f) depict an alternative embodiment of a receptor-binding SSA. This embodiment is essentially the same as that described in FIGS. 1(a)–1(f) except that instead of using beads, the embodiment shown in FIGS. 2(a)–2(f) uses a well bottom 22 made of plastic doped with scintillant and coated with a material to which the membranes adhere. Consequently, instead of detecting the luminescence of the beads, the embodiment shown in FIGS. 2(a)–2(f) detects the luminescence of the well bottom.

FIGS. 3(a)–3(d) depict the steps of an embodiment of an enzyme SSA. In FIG. 3(a), scintillant-doped beads 40 with radio-labeled peptides 42 attached thereto are added to a well 50 containing a liquid 60. In FIG. 3(b), a test compound 44 is added to the well. In FIG. 3(c), enzymes 46 are added to the well. If not inhibited, enzymes 46 will cleave radio-labeled peptides 42 from beads 40. As a result, the radio label will diffuse into the solution, and radio-label decay will not produce luminescence in beads 40. If, on the other hand, test compound 44 inhibits enzymes 46, typically by blocking the enzyme active site, enzymes 46 will not cleave the radio label and the decay of the radio label will produce luminescence in the beads. In FIG. 3(d), the luminescence of the beads is measured and the activity of the test compound can be determined.

FIGS. 4(a)–4(d) depict an alternative embodiment of an enzyme SSA. In FIG. 4(a), radio-labeled peptides 42 are attached to a scintillant-doped well bottom 52. In FIG. 4(b), the test compound 44 is added to the well. In FIG. 4(c), enzymes 46 are added to the well. In FIG. 4(d), the luminescence of the well bottom is measured to determine the activity of the test compound.

The above examples illustrate the general principle of the SSA, namely that the activity of interest is assayed by a change in the number of radio labels within a radio-decay length of the scintillant. One of the attractions of SSAs is that the radio labels not attached to the scintillant need not be removed from the well in a wash step. That is SSAs are homogeneous assays.

A radioinunnoassay (RIA) is a specific form of a receptor binding assay in which the receptor is an antibody and the ligand is most often a natural or synthetic peptide, protein, carboydrate or small organic molecule. RIAs are an indirect method for measuring the concentration of ligand in any prepared sample, most often a biological sample such as plasma, cerebrospinal fluid, urine, or cellular extract. In a standard RIA, the antibody has a specific affinity for the ligand and the assay contains the antibody, a fixed concentration of radiolabeled ligand and an unknown concentration of non-labelled ligand. The concentration of the unlabelled ligand is determined by the degree to which it binds to the antibody and thereby blocks binding of the labelled ligand. RIAs are most often performed as heterogenous assays that require the separation of bound ligand from unbound ligand with a wash step. RIAs have also been developed using an SSA configuration in which the antibody receptor is attached to a scintillant filled bead and the wash step is eliminated.

SSAs and RIAs, however, suffer from a number of disadvantages. First, these assays require handling radioactive material, which is both expensive and time consuming. Second, these assays are only effective in large wells. The rate of luminescence emission from the beads or well bottoms is proportional to the beta particle emission rate. A typical $^3$H assay yields less than one detected photon per $^3$H decay. To increase the speed of the assay, the quantity of radio-labeled ligand must be increased, and correspondingly the quantities of membranes, beads and test compound. In order to perform a tritium SSA in 10–60 seconds, $10^7$ beads must be used. This quantity of beads requires a well of approximately 150 µL. SSAs are not effective in the µL-volume wells desirable for screening large numbers of compounds.

As described below, the present invention, inter alia, replaces the radio-labeled ligands of the SSA and the RIA with fluorescent-labeled ligands. In so doing, it introduces a homogenous format for the RIA and it advantageously retains the homogeneous format of the SSA. This is particularly important in µL-volume wells, for which surface tension renders washing impractical. However, in a homogeneous format, fluorescence can be a problem as can be illustrated with the receptor-binding assay. When the test compound is added, some fluorescent-labeled ligands are displaced and diffuse freely throughout the volume of the well, while others remain attached to the membranes. It is the fluorescence of the fluorescent-labeled ligands attached to the membranes that is used to determine the activity of the test compound. If the fluorescence is detected from the entire well, however, the emission from the fluorescent-labeled ligands in the volume of the well will obscure the emission from the fluorescent-labeled ligands attached to the membranes.

One method addressing this problem is described in U.S. Pat. No. 5,355,215 to Schroeder et al. and shown in FIGS. 5(a) and 5(b). According to the Schroeder et al. method, the samples are illuminated by a beam 134 of light that is directed at the bottom of the well at an oblique angle, shown as A in FIG. 5, so that it does not illuminate the entire well. In addition, while the beam illuminates area 114', fluorescence is detected only from area 114a which is under the well volume which receives the least amount of illumination.

The Schroeder et al. method, however, suffers from a number of disadvantages. First, because it detects only a small portion of the well bottom, the Schroeder et al. method can only be performed with a sufficient degree of accuracy on fairly large wells. It is not suitable to image samples disposed in the approximately 1-mm diameter wells of a 1536-well plate. Second, the geometric constraints of the angled illumination preclude the use of high numerical aperture collection optics, necessary to achieve sufficient sensitivity and resolution to image micron-sized objects, such as individual cells, at the bottom of the well.

Another approach to this problem uses a point-scan microscope. For example, in U.S. Pat. No. 5,547,849 to Baer et al., the use of a point-scan confocal system is taught. Baer et al. teach a method to increase the slow speed of image acquisition, inherent in point-scan confocal techniques, by sacrificing spatial resolution. If, for example, one expands the diameter of the illumination beam on the sample by a factor of 10, then the illumination area is increased 100-fold, permitting one to scan 100-times faster, under certain conditions. The speed increase is achieved, however, at the expense of resolution. Further, the detection devices appropriate to said scanning method, as disclosed in the '849 patent, are inferior, principally in terms of sensitivity, to those advantageously used in the present invention. Finally, the degree of background rejection is diminished along with the resolution. Thus the device disclosed in the '849 patent has lesser sensitivity, higher background and lower resolution than the present invention, all of which are important in the present application.

The present invention includes novel embodiments of a line-scan confocal microscope. Line-scan confocal microscopes are known in art. Two representative embodiments are the system disclosed by White et al. in U.S. Pat. No. 5,452,125 and that published by Brakenhoff and Visscher in *J. Microscopy* 171 17–26 (1993), shown in FIG. 7. Both use a scanning mirror to sweep the illumination across the sample. The same mirror de-scans the fluorescence radiation. After spatial filtering with a slit, the fluorescence is rescanned for viewing by eye. The use of the oscillating mirror enables these microscopes to rapidly scan a field-of-view. Line illumination is advantageous principally in applications requiring rapid imaging. The potential speed increase inherent in the parallelism of line illumination as compared to point illumination is, however, only realized if the imaging system is capable of detecting the light emitted from each point of the sample along the illumination line, simultaneously. An essential feature of the disclosed apparatus is the use of a detection device having manifold, independent detection elements in a plane conjugate to the object plane.

According to the present invention, the sample must lie in a "plane", where the depth-of-field of the imaging system determines the precision of "planarity". In a preferred embodiment, the imaged area is 1 mm$^2$ and the depth-of-field is 10 $\mu$m. Thus, if the entire field is to be in focus simultaneously, the sample must be flat to 1 part in 100. This is true of many sample substrates (e.g. microtiter plates) over a local area (such as the central area of the well bottom). It is not practical, however, to require that the sample substrate be flat over its entire surface. For a microtiter plate having an extent of ~100 mm, planarity of 1 part in 10,000 would be necessary.

The present invention provides for an optical autofocus system which maintains in "focus" the portion of the sample substrate being imaged. An optical autofocus mechanism has the advantage of being fast and being operational with non-conducting substrates such as plastic microtiter plates and microscope slides. Advantageously, this focus mechanism operates with negligible delay, that is, the response time of the focusing mechanism is short relative to the image acquisition-time, preferably a fraction of a second. Optically-based autofocus mechanisms suitable for the present application are known. For example, an astigmatic-lens-based system for the generation of a position error signal suitable for servo control is disclosed in *Applied Optics* 23 565–570 (1984), and a focus error detection system utilizing a "skew beam" is disclosed in *SPIE* 200 73–78 (1979). In a preferred embodiment of the present invention, the sample substrate is a microtiter plate. In this case, the preferred means of accomplishing the focusing depends further on the properties of the plate. If the thickness of the plate bottom were uniform to within a fraction of the depth-of-focus, then a focusing mechanism that maintained the plate bottom at a constant offset from the object plane would be adequate. Presently, commonly used microtiter plates are not sufficiently uniform. Thus, the focusing mechanism must track the surface on which the sample resides, which is typically the inside of the microtiter plate well. An aspect of the present invention is a novel autofocus mechanism for rapidly focusing on a discontinuous surface, such as the well bottom of a microtiter plate.

There is, therefore, a need for a method and apparatus for screening large numbers of chemical compounds accurately, quickly and inexpensively, in a homogeneous format. In addition, there is a need for a methods and apparatus that can perform multi-parameter fluorescence imaging with sufficient resolution to image individual cells and sub-cellular events. There is also a need for an imaging system that can additionally monitor a statistically significant population of cells at video-rates.

SUMMARY OF THE INVENTION

The present invention relates to a line-scan confocal microscope and the use of a line-scan confocal imaging (LCI) system to assay biological activity.

In a preferred embodiment, the line-scan confocal imaging system employs laser light sources of multiple wavelengths for illuminating the sample and exciting fluorophores to emit electromagnetic energy. These wavelengths include the ultraviolet spectrum as well as the visible.

The present invention is able to conduct a rapid series of assays on micro-well plates by use of an autofocus capability which allows the LCI system to rapidly move from one well to another but not lose the advantage of the confocal microscope's inherent ability to resolve thin optical sections.

In various embodiments of the present invention the sample is moved to effect a scan of the line of illumination over the sample. In other embodiments, an oscillating mirror is used to produce a rapidly moving line of illumination effecting a scan of a sample which remains at a fixed position. By way of example, images can be obtained at a rate of up to 50 frames per second.

The present invention preferably provides for integrated dispensing allowing the addition of substances to initiate rapidly changing biological events, such as the propagation of an action potential in nerve or muscle cells.

The present invention preferably makes use of a multi-element solid state detection device such as a charged coupled device (CCD). This device is preferably read continuously. In a preferred embodiment, the present invention uses a rectangular CCD which avoids the need for a full two dimensional detector and allows higher read speeds. In addition, a larger effective field-of-view is achievable in the stage-scanning embodiment.

The present invention also provides in a preferred embodiment, a capability to conduct specialized data analysis simultaneously with data acquisition to allow it to operate in a high-throughput screening mode.

This invention provides methods of performing a wide variety of biological assays utilizing fluorescence. In one embodiment the target of interest may be in a fixed or live cell or in a subcellular organelle or on the cell membrane. These assays involve the determination of one or more parameters which requires the excitation of one or more fluorescent labels which are, in general, sensitive to different wavelengths of incident light. In addition these assays require the simultaneous and precise imaging of the emitted light at one or more wavelengths from which the location in two or three dimensions and the intensity of the fluorescently labeled species and their correlations are determined.

In addition, this invention provides methods to perform assays which require either a single imaging of a response, by means of fluorescent emission, or rapidly repeated imaging of the same area or cell. In various embodiments, imaging is performed at rates as high as 50 frames per second. This ability to image rapidly, in multiple wavelengths and with high spatial resolution allows the present invention to perform assays that could not previously be performed or to perform them in a superior manner.

The present invention relates to several methods for screening chemical compounds and for performing many types of assays involving the use of fluorophores or fluorescent probes. In general these assays and screening procedures involve the use of a test compound and reagents some or all of which are intrinsically fluorescent, tagged with fluorescent labels or are metabolized into fluorescent product. The test compound and the reagents may be combined in a variety of ways.

In one embodiment, the reagents are added to a well containing a liquid. This may be a single well or one of many wells on a multiwell plate. The biological activity of interest is determined by the presence or absence of fluorophores disposed on the bottom of the well or on the surface of beads disposed on the bottom of the well as measured with a line-scan confocal microscope. This embodiment has in common with the SSA format the determination of activity from the localization of the detected species. In the case of the SSA, the localization is proximal to the scintillant. In the present method, the localization is to a region of the well, preferably the bottom. In the case of the SSA, sensitivity to the proximal species is determined by the decay length of the beta particles. In the present method, sensitivity to the localized fluorophore is determined by the optical-sectioning depth of the confocal microscope.

In addition, the present invention can perform high throughput assays requiring scanning multiple samples in a rapid and automatic manner. These samples may be individual micro-wells and may involve wells containing a liquid and live or fixed cells or components of cells. The present invention also provides environmental controls required to retain liquid samples or sustain live cells during the analysis.

BRIEF DESCRIPTION OF THE DRAWINGS

These and other objects, features and advantages of the invention will be more readily apparent from the following detailed description in which:

FIGS. 3(a)–3(d) illustrate a first enzyme SSA.

FIGS. 4(a)–4(d) illustrate a second enzyme SSA.

FIGS. 17(a)–17(d) illustrate a first embodiment of an enzyme assay according to the present invention.

FIGS. 18(a)–18(d) illustrate a second embodiment of an enzyme assay according to the present invention.

FIG. 25(a) graphically depicts competitive binding of labeled and unlabeled ligands to a cell surface receptor. FIGS. 25(b)–(d) show images of immunofluorescence at indicated points on the graph.

DETAILED DESCRIPTION OF THE INVENTION

Figure 1A:
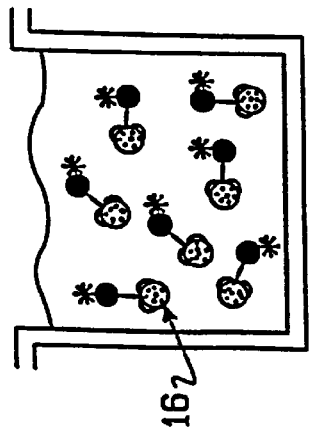
FIGS. 1(a)–1(f) illustrate a first receptor-binding SSA.
Figure 1B:
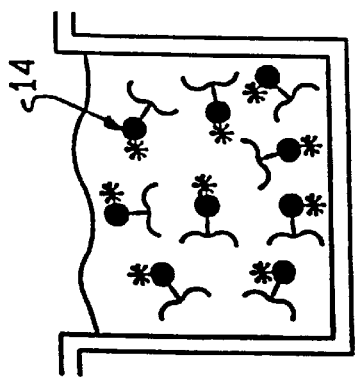
Figure 1C:
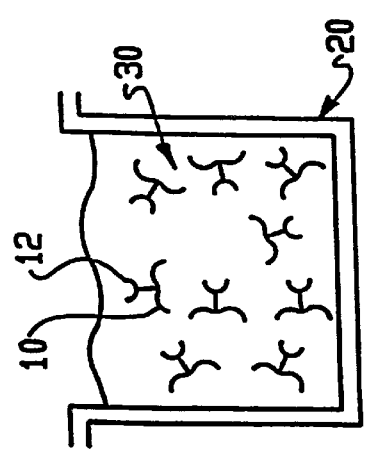
Figure 1D:
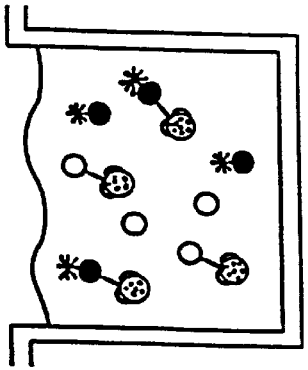
Figure 1E:
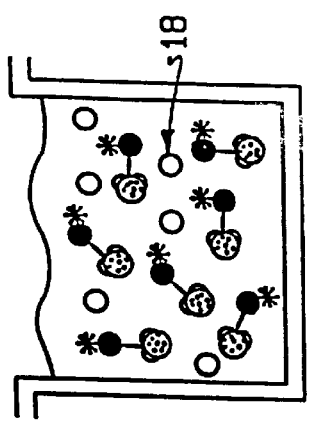
Figure 1F:
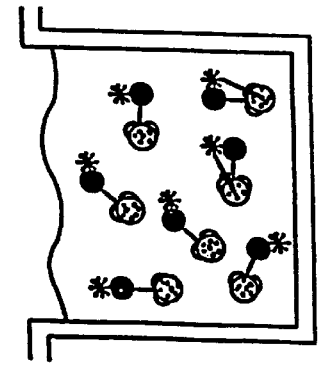
Figure 2A:
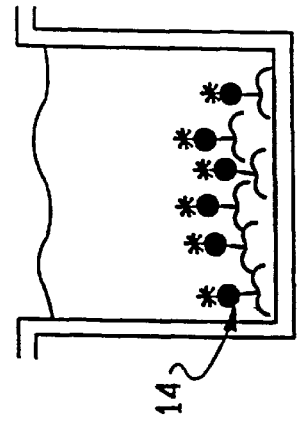
FIGS. 2(a)–2(f) illustrate a second receptor-binding SSA.
Figure 2B:
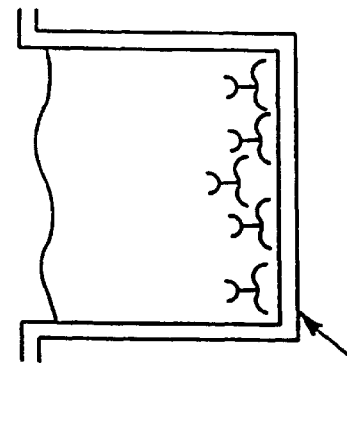
Figure 2C:
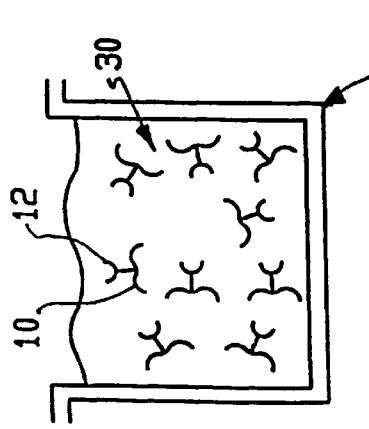
Figure 2D:
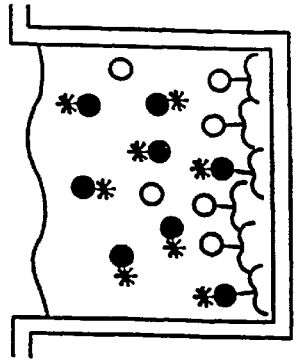
Figure 2E:
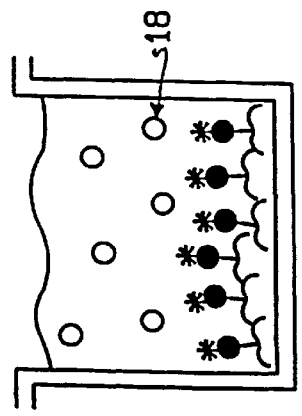
Figure 2F:
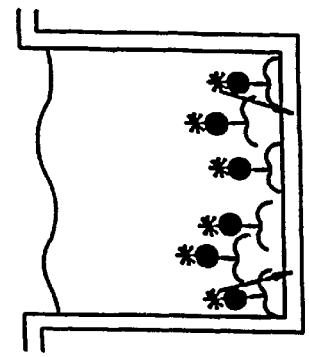
Figure 5A:
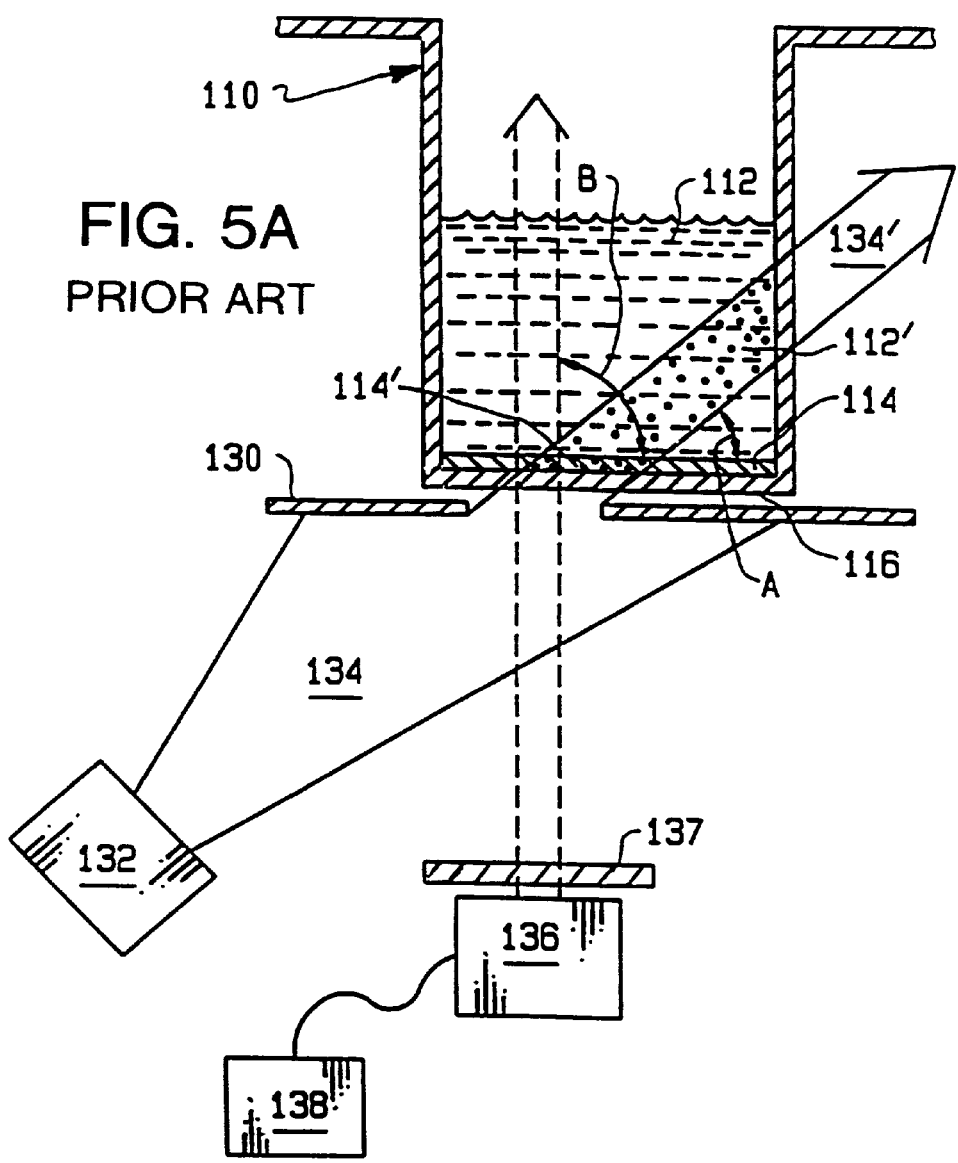
FIGS. 5(a) and 5(b) are schematic views of a prior art apparatus for imaging samples disposed on bottom of a well.
Figure 5B:
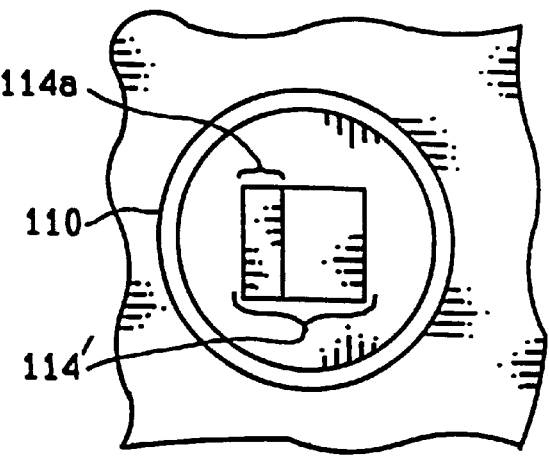

All patent applications, publications, and other references that are listed herein are hereby incorporated by reference in their entireties.

The present invention if useful for identifying pharmacological agents for the treatment of disease. It provides a high throughput method for conducting a wide variety of biological assays where one or more fluorescent reagents are employed to measure a biological response. Such assays can be conducted on chemical compounds or any molecule of biological interest, included but not limited to drug candidates, such as those found in combinatorial libraries. In addition, this invention provides a method for the diagnosis of pathological states from cell and tissue samples. This invention also provides a method for profiling multiple biological responses of drug candidates on whole cells using fluorescent reagents.

The techniques of the present invention may be used in assays in which data is acquired on individual cells, on a cellular or sub-cellular level, sufficiently rapidly so as to permit the acquisition of such data on a sufficient number of cells to constitute a statistically meaningful sample of the cell population. The present invention is able to make simultaneous measurements on multiple parameters and is also able to correlate multiple signals from individual cells. It may therefore be employed to assay heterogeneous cellular responses and to assay responses confined to a small subset of cells.

In addition, the present invention can image the simultaneous activation of multiple signal pathways and can correlate multiple signals simultaneously and over time. This capability is vital when the temporal response of individual cells or a comparison of the temporal response of individual cells is required for the specific assay.

In addition, the present invention can image fluorescent signals from the confocal plane of cells in the presence of unbound fluorophore or in the presence of intrinsically fluorescent chemical compounds, including potential drug candidates.

These assays may make use of any known fluorophore or fluorescent label including but not limited to fluorescein, rhodamine, Texas Red, Amersham Corp. stains Cy3, Cy5, Cy5.5 and Cy7, Hoechst's nuclear stains and Coumarin stains. (See Haugland R. P. Handbook of Fluorescent Probes and Research Chemicals $6^{th}$ Ed., 1996, Molecular Probes, Inc., Eugene, Oreg.)

These assays include but are not limited to receptor-binding assays, assays of intracellular electric potential or pH, assays of ion concentrations, enzyme activity assays, trafficking assays, kinetic imaging assays and assays of rare cellular events.

Receptor-binding and enzyme activity assays may be bead-based or cell-based assays. Some examples of bead-based assays are described in WO 98/55866. However, the method described therein makes use of point scan confocal technology and the present linescan confocal imaging system would have a significant advantage in terms of rate of data acquisition.

OPTICAL CONFIGURATION

Figure 6:
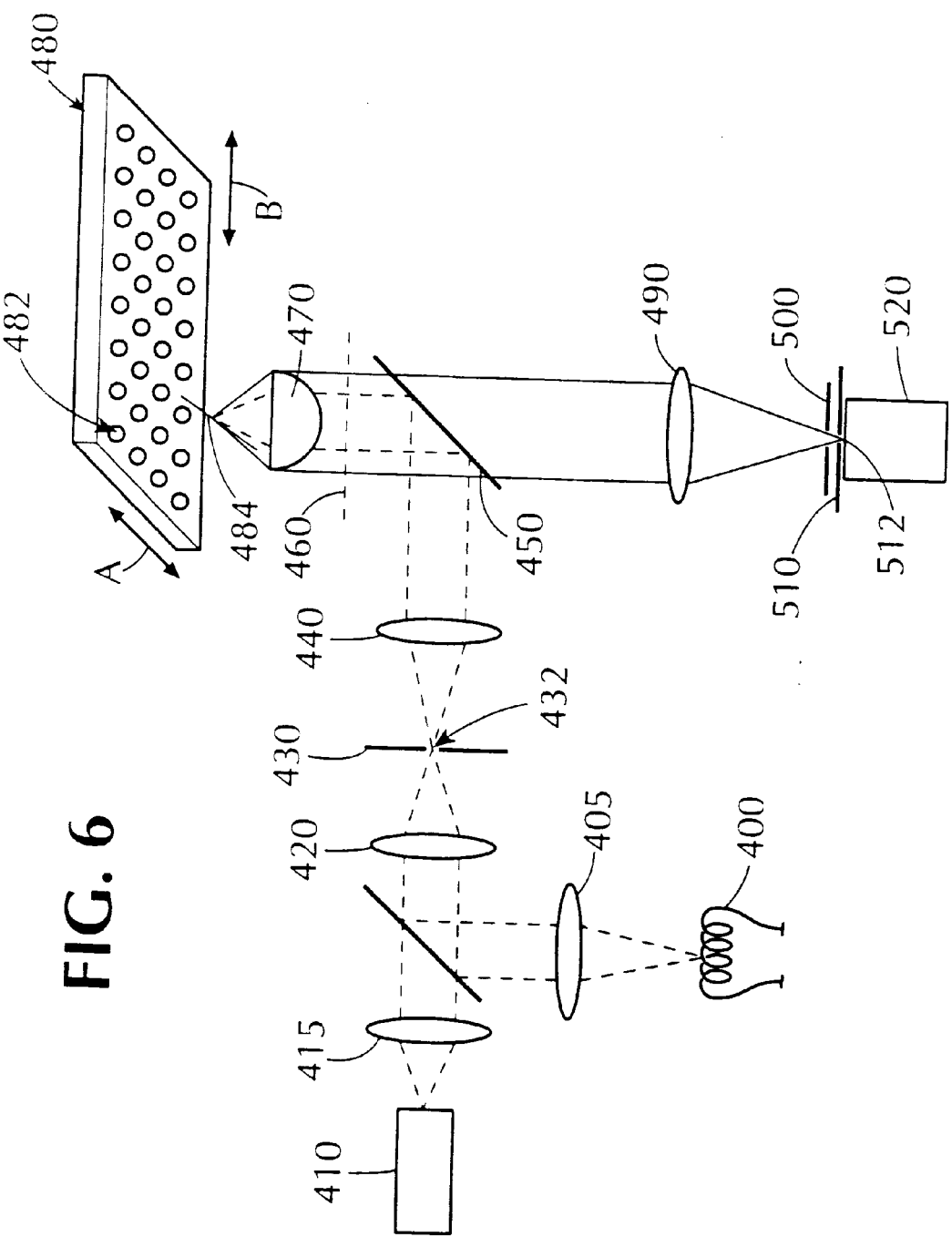
FIG. 6 is a schematic view of a first embodiment of a line-scan confocal microscope used to image samples according to the present invention.
Figure 7:
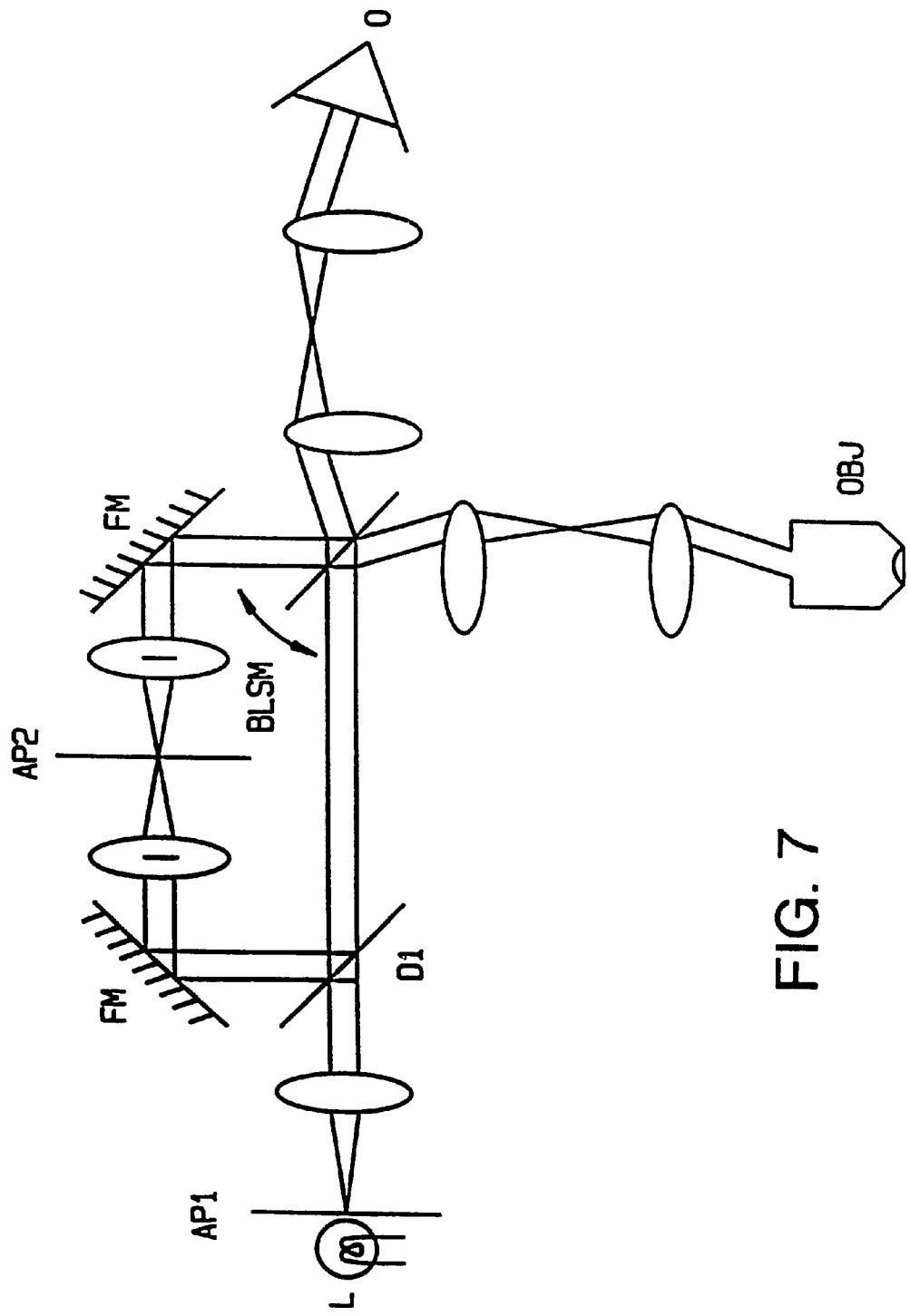
FIG. 7 is a schematic view of a prior art microscope.

FIG. 6 shows a first embodiment of the present invention. The microscope comprises a source 400 or 410 of electromagnetic radiation for example, in the optical range, 350–750 nm, a cylindrical lens 420, a first slit mask 430, a first relay lens 440, a dichroic mirror 450, an objective lens 470, a microtiter plate 480 containing a two-dimensional array of sample wells 482, a tube lens 490, a filter 500, a second slit mask 510 and a detector 520. These elements are arranged along optical axis OA with slit apertures 432, 512 in masks 430, 510 extending perpendicular to the plane of FIG. 6. The focal lengths of lenses 440, 470 and 490 and the spacings between these lenses as well as the spacings between mask 430 and lens 440, between objective lens 470 and microtiter plate 480 and between lens 490 and mask 510 are such as to provide a confocal microscope. In this embodiment, electromagnetic radiation from a lamp 400 or a laser 410 is focused to a line using a cylindrical lens 420. The shape of the line is optimized by a first slit mask 430. The slit mask 430 is depicted in an image plane of the optical system, that is in a plane conjugate to the object plane. The illumination stripe formed by the aperture 432 in the slit mask 430 is relayed by lens 440, dichroic mirror 450 and objective lens 470 onto a microtiter plate 480 which contains a two-dimensional array of sample wells 482. For convenience of illustration, the optical elements of FIG. 6 are depicted in cross-section and the well plate in perspective. The projection of the line of illumination onto well plate 480 is depicted by line 484 and is also understood to be perpendicular to the plane of FIG. 6. As indicated by arrows A and B, well plate 480 may be moved in two dimensions (X, Y) parallel to the dimensions of the array by means not shown.

In an alternative embodiment, the slit mask 430 resides in a Fourier plane of the optical system, that is in a plane conjugate to the objective back focal plane (BFP) 460. In this case the aperture 432 lies in the plane of the figure, the lens 440 relays the illumination stripe formed by the aperture 432 onto the back focal plane 460 of the objective 470 which transforms it into a line 484 in the object perpendicular to the plane of FIG. 6.

In an additional alternative embodiment the slit mask 430 is removed entirely. According to this embodiment, the illumination source is the laser 410, the light from which is focused into the back focal plane 460 of the objective 470. This can be accomplished by the combination of the cylindrical lens 420 and the spherical lens 440 as shown in FIG. 6, or the illumination can be focused directly into the plane 460 by the cylindrical lens 420.

An image of the sample area, for example a sample in a sample well 482, is obtained by projecting the line of illumination onto a plane within the sample, imaging the fluorescence emission therefrom onto a detector 520 and moving the plate 480 in a direction perpendicular to the line of illumination, synchronously with the reading of the detector 520. In the embodiment depicted in FIG. 6, the fluorescence emission is collected by the objective lens 470, projected through the dichroic beamsplitter 450, and imaged by lens 490 through filters 500 and a second slit mask 510 onto a detector 520, such as is appropriate to a confocal imaging system having an infinity-corrected objective lens 470. The dichroic beamsplitter 450 and filter 500 preferentially block light at the illumination wavelength. The detector 520 illustratively is a camera and may be either one dimensional or two dimensional. If a one dimensional detector is used, slit mask 510 is not needed. The illumination, detection and translation procedures are continued until the prescribed area has been imaged. Mechanical motion is simplified if the sample is translated at a continuous rate. Continuous motion is most useful if the camera read-time is small compared to the exposure-time. In a preferred embodiment, the camera is read continuously. The displacement d of the sample during the combined exposure-time and read-time may be greater than or less than the width of the illumination line W, exemplary 0.5 W≦d≦5 W. All of the wells of a multiwell plate can be imaged in a similar manner.

Alternatively, the microscope can be configured to focus a line of illumination across a number of adjacent wells, limited primarily by the field-of-view of the optical system. Finally, more than one microscope can be used simultaneously.

The size and shape of the illumination stripe 484 is determined by the width and length of the Fourier transform stripe in the objective lens back focal plane 460. For example, the length of the line 484 is determined by the width of the line in 460 and conversely the width in 484 is determined by the length in 460. For diffraction-limited performance, the length of the illumination stripe at 460 is chosen to overfill the objective back aperture. It will be evident to one skilled in the art that the size and shape of the illumination stripe 484 can be controlled by the combination of the focal length of the cylindrical lens 420 and the beam size at 420, that is by the effective numerical aperture in each dimension, within the restrictions imposed by aberrations in the objective, and the objective field of view.

The dimensions of the line of illumination 484 are chosen to optimize the signal to noise ratio. Consequently, they are sample dependent. Depending on the assay, the resolution may be varied between diffraction-limited, i.e., less than 0.5 $\mu$m, and approximately 5 $\mu$m. The beam length is preferably determined by the objective field of view, exemplary between 0.5 and 1.5 mm. A Nikon ELWD, 0.6 NA, 40X× objective, for example, has a field of view of approximately 0.75 mm. The diffraction-limited resolution for 633 nm radiation with this objective is approximately 0.6 $\mu$m or approximately 1100 resolution elements.

The effective depth resolution is determined principally by the width of aperture 512 in slit mask 510 or the width of the one dimensional detector and the image magnification created by the combination of the objective lens 470 and lens 490. The best depth resolution of a confocal microscope approaches 1 $\mu$m. In the present application, a depth resolution of 5–10 $\mu$m may be sufficient or even advantageous.

For example, when the sample of interest, such as a live cell, contains insufficient fluorophores in a diffraction-limited volume to permit an adequate signal-to-noise image in a sufficiently brief image-acquisition time, it is advantageous to illuminate and collect the emission from a larger than diffraction-limited volume. A similar situation prevails in the case of video-rate kinetics studies of transient events such as ion-channel openings. Practically, this is accomplished by underfilling the back aperture of the objective lens, which is equivalent to increasing the diameter of the illumination aperture. The effective numerical aperture ("NA") of the illumination is less than the NA of the objective. The fluorescence emission is, however, collected with the full NA of the objective lens. The width of aperture 512 must be increased so as to detect emission from the larger illumination volume. At an aperture width a few times larger than the diffraction limit, geometrical optics provides an adequate approximation for the size of the detection-volume element:

Lateral Width: $a_d = d_d/M$,

Axial Width: $Z_d = \sqrt{2}a_d/\tan\alpha$, where M is the magnification, $d_d$ is the width of aperture 512 and $\alpha$ is the half-angle subtended by the objective 470. It is an important part of the present invention that the illumination aperture 432 or its equivalent in the embodiment having no aperture and the detection aperture 512 be independently controllable.

MULTI-WAVELENGTH CONFIGURATION

An embodiment enabling multi-wavelength fluorescence imaging is preferred for certain types of assays. It is generally advantageous and often necessary that two or more measurements be made simultaneously since one important parameter in a biological response is time.

Figure 8A:
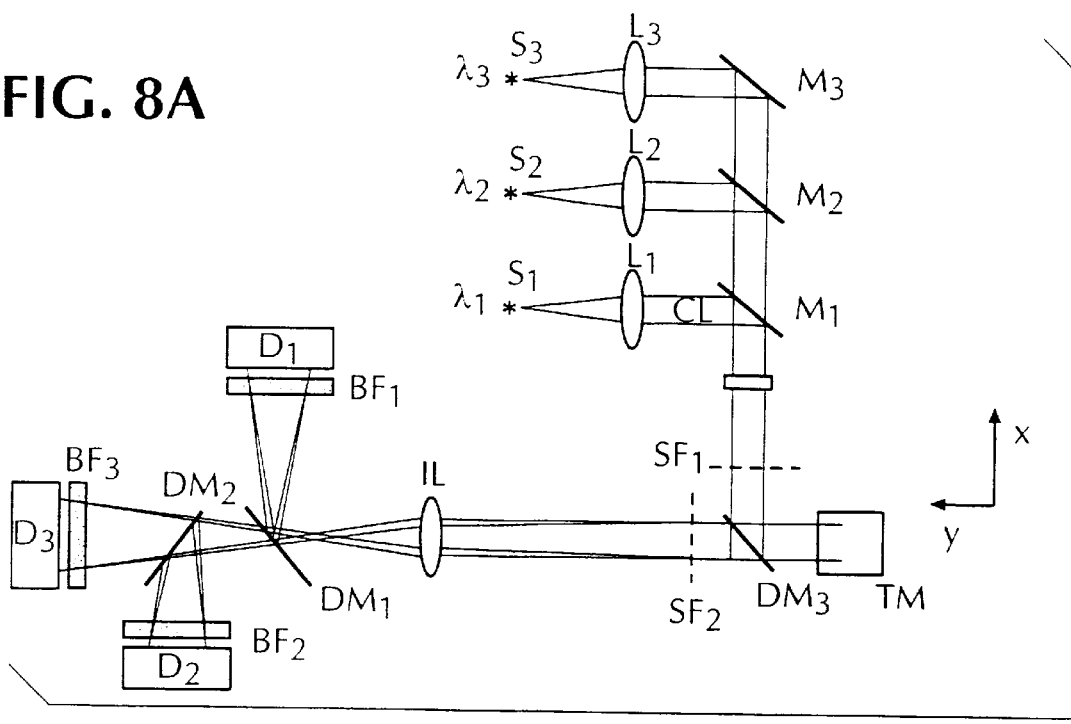
FIGS. 8(a) and 8(b) are, respectively, a top view and a side view of the ray path of a multicolor embodiment of the present invention, without a scanning mirror.
Figure 8B:
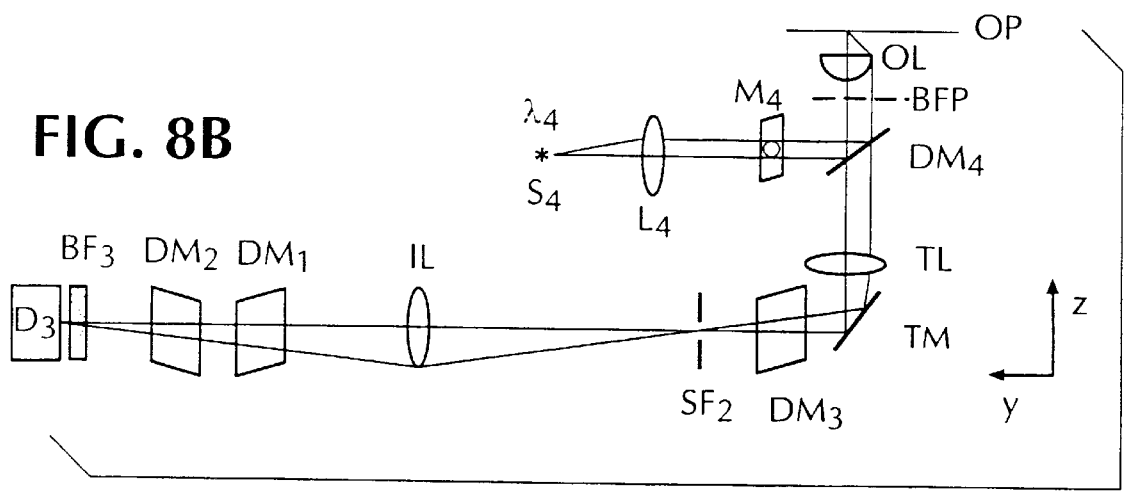

The number of independent wavelengths or colors will depend on the specific assay being performed. In one embodiment three illumination wavelengths are used. FIGS. 8(a) and 8(b) depict the ray paths in a three-color line-scan confocal imaging system, from a top view and a side view respectively. In general, the system comprises several sources $S_n$ of electromagnetic radiation, collimating lenses $L_n$, and mirrors $M_n$ for producing a collimated beam that is focused by cylindrical lens CL into an elongated beam at first spatial filter $SF_1$, a confocal microscope between first spatial filter $SF_1$, and second spatial filter $SF_2$ and an imaging lens IL, beamsplitters $DM_1$ and $DM_2$ and detectors $D_n$ for separating and detecting different wavelength components of fluorescent radiation from the sample. Spatial filters SF, and $SF_1$ and $SF_2$ preferably are slit masks.

In particular, FIG. 8(a) depicts sources, $S_1$, $S_2$ and $S_3$, for colors $\lambda_1$, $\lambda_2$ and $\lambda_3$, and lenses $L_1$, $L_2$ and $L_3$ that collimate the light from the respective sources. Lenses $L_1$, $L_2$ and $L_3$, preferably are adjusted to compensate for any chromaticity of the other lenses in the system. Mirrors $M_1$, $M_2$ and $M_3$ are used to combine the illumination colors from sources $S_n$. The mirrors $M_2$ and $M_1$ are partially transmitting, partially reflecting and preferentially dichroic. $M_2$, for example, should preferentially transmit $\lambda_3$, and preferentially reflect $\lambda_2$. It is thus preferential that $\lambda_3$ be greater than $\lambda_2$.

Operation of the microscope in a confocal mode requires that the combined excitation beams from sources $S_n$ be focused to a "line", or an highly eccentric ellipse, in the object plane OP. As discussed in connection to FIG. 6 above, a variety of configurations may be used to accomplish this. In the embodiment depicted in FIG. 8, the combined illumination beams are focused by cylindrical lens CL into an elongated ellipse that is coincident with the slit in the spatial filter $SF_1$. As drawn in FIGS. 8a and 8b, the slit mask $SF_1$ resides in an image plane of the system, aligned perpendicular to the propagation of the illumination light and with its long axis in the plane of the page of FIG. 8a. The lenses TL and OL relay the illumination line from the plane containing $SF_1$ to the object plane OP. A turning mirror, TM, is for convenience. In another embodiment, $DM_3$ is between TL and OL and CL focuses the illumination light directly into the BFP. Other embodiments will be evident to one skilled in the art.

Referring to FIG. 8(b), the light emitted by the sample and collected by the objective lens, OL, is imaged by the tube lens, TL, onto the spatial filter, $SF_2$. $SF_2$ is preferentially a slit aligned so as to extend perpendicular to the plane of the page. Thus, the light passed by filter $SF_2$ is substantially a line of illumination. $SF_2$ may be placed in the primary image plane or any plane conjugate thereto. $DM_3$ is partially reflecting, partially transmitting and preferably "multichroic". Multi-wavelength "dichroic" mirrors, or "multichroic" mirrors can be obtained that preferentially reflect certain wavelength bands and preferentially transmit others.

$\delta\lambda_1$ will be defined to be the fluorescence emission excited by $\lambda_1$. This will, in general, be a distribution of wavelengths somewhat longer than $\lambda_1$. $\delta\lambda_2$ and $\delta\lambda_3$ are defined analogously. $DM_3$ preferentially reflects $\lambda_n$, and preferentially transmits $\delta\lambda_n$, n=1,2,3. The light transmitted by $SF_2$ is imaged onto the detection devices, which reside in planes conjugate to the primary image plane. In FIG. 8(a), an image of the spatial filter $SF_2$ is created by lens IL on all three detectors, $D_n$. This embodiment is preferred in applications requiring near-perfect registry between the images generated by the respective detectors. In another embodiment, individual lenses $IL_n$ are associated with the detection devices, the lens pairs IL and $IL_n$ serving to relay the image of the spatial filter $SF_2$ onto the respective detectors $D_n$. The light is split among the detectors by mirrors $DM_1$ and $DM_2$. The mirrors are partially transmitting, partially reflecting, and preferentially dichroic. $DM_1$ preferentially reflects $\delta\lambda_1$ and preferentially transmits $\delta\lambda_2$ and $\delta\lambda_3$. The blocking filter, $BF_1$, preferentially transmits $\delta\lambda_1$ effectively blocking all other wavelengths present. $DM_2$ preferentially reflects $\delta\lambda_2$ and preferentially transmits $\delta\lambda_3$. The blocking filters, $BF_2$ and $BF_3$, preferentially transmit $\delta\lambda_2$ and $\delta\lambda_3$ respectively, effectively blocking all other wavelengths present

SCANNING MIRROR CONFIGURATION

In some embodiments of this invention, rapid data acquisition requires framing images at video rates. Video-rate imaging generally refers to 30 or 60 frames per second. In the present use, it is intended to connote frame rates with an order-of-magnitude of 30 Hz. In a preferred embodiment, video-rate imaging is achieved by illuminating along one dimension of the sample plane and scanning the illumination beam in the direction perpendicular thereto so as to effect a relative translation of the illumination and sample. The scanning stage is generally massive. Consequently, it cannot be moved sufficiently rapidly.

Figure 9A:
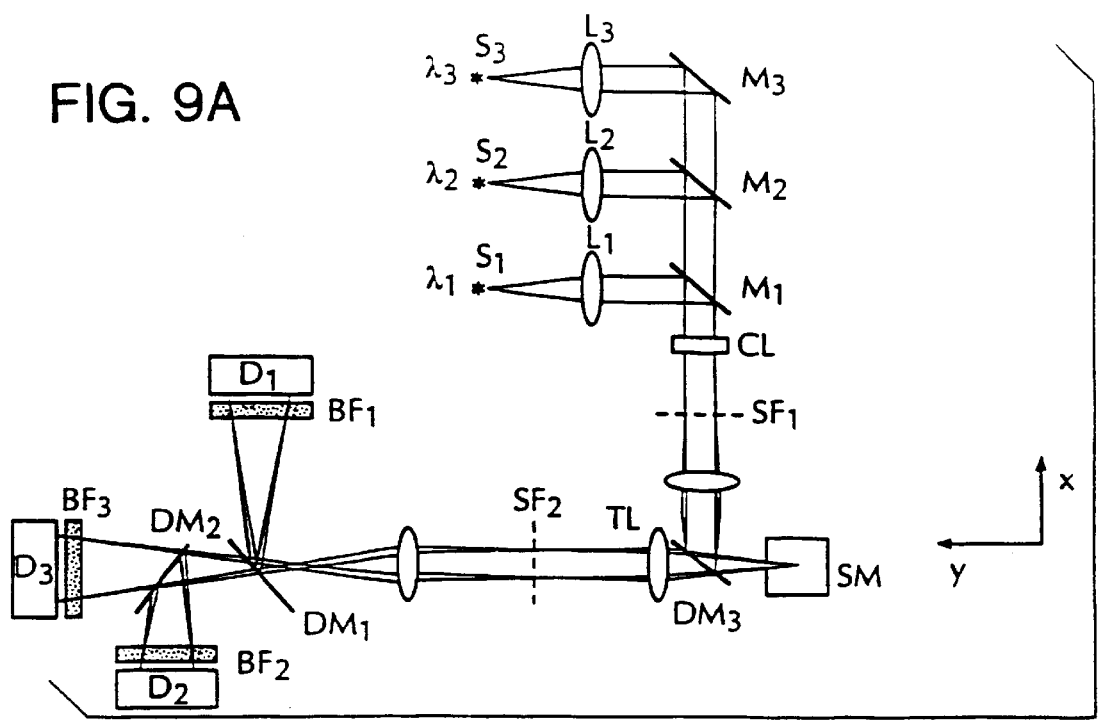
FIGS. 9(a) and 9(b) are, respectively, a top view and a side view of the ray path of thy multicolor embodiment of the present invention with the scanning mirror.
Figure 9B:
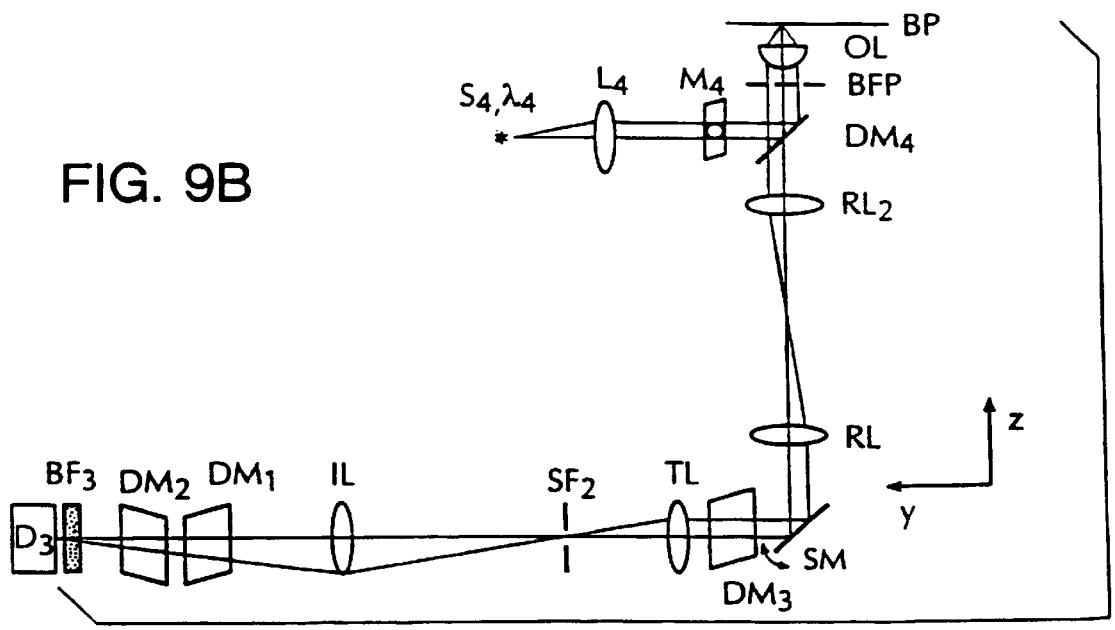
Figure 9C:
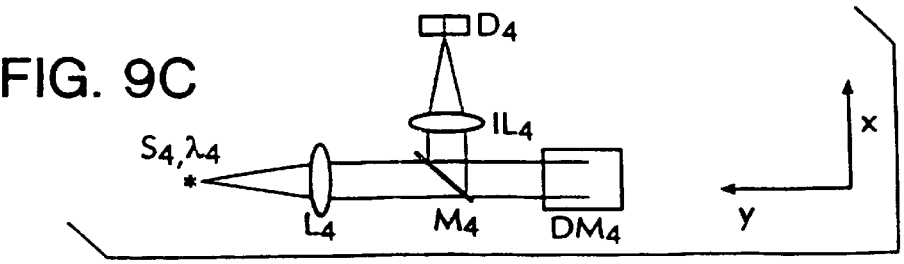
FIG. 9(c) is a top view of the ray path of the single beam autofocus.

FIG. 9 depicts an embodiment of the invention utilizing a scanning mirror, SM. The mirror is advantageously placed in a plane conjugate to the objective back focal plane (BFP): A rotation in the BFP (or a plane conjugate thereto) effects a translation in the object plane (OP) and its conjugate planes. The full scan range of SM need only be a few degrees for typical values of the focal lengths of the lenses $RL_1$ and $RL_2$. As shown in FIG. 9, this lens pair images the BFP onto the SM at a magnification of one, but a variety of magnifications can be advantageously used. The limiting factors to the image acquisition rate are the camera read-rate and the signal strength. In the imaging mode described above, data can be acquired continuously at the camera read-rate, exemplary 1 MHz. With a scanning mirror, it is preferable to acquire data uni-directionally. The idealized scanning motion allowing one to acquire data continuously is the sawtooth. In practice, the combination of turn-around and return scan times will constitute $\sim\frac{1}{3}-\frac{2}{3}$ of the scan period. Assuming 50% dead-time, a mirror oscillation frequency of 50 Hz and a pixel acquisition rate of 1 MHz, ~10,000 pixels would be acquired per frame at 50 frames per second, which is sufficient to define and track individual objects, such as cells, from frame to frame. $10^4$ pixels per image is, however, $10^2$-times fewer than was generally considered above. Depending on the application, it is advantageous to acquire relatively smaller images at high resolution, e.g. 50-$\mu$m×50-$\mu$m at 0.5-$\mu$m×0.5-$\mu$m pixelation, or relatively larger images at lower resolution, e.g. 200-$\mu$m×200-$\mu$m at 2-$\mu$m pixelation.

AUTOFOCUS

According to the present invention, the sample must lie in the object plane of an imaging system. Accordingly, the invention provides an autofocus mechanism that maintains the portion of the sample in the field-of-view of the imaging system within the object plane of that system. The precision of planarity is determined by the depth-of-field of the system. In a preferred embodiment, the depth-of-field is approximately 10 $\mu$m and the field-of-view is approximately 1 $mm^2$.

The disclosed autofocus system operates with negligible delay, that is, the response time is short relative to the image acquisition-time, exemplary 0.01–0.1 s. In addition, the autofocus light source is independent of the illumination light sources and the sample properties. Among other advantages, this configuration permits the position of the sample carrier along the optical axis of the imaging system to be determined independent of the position of the object plane.

Figure 8C:
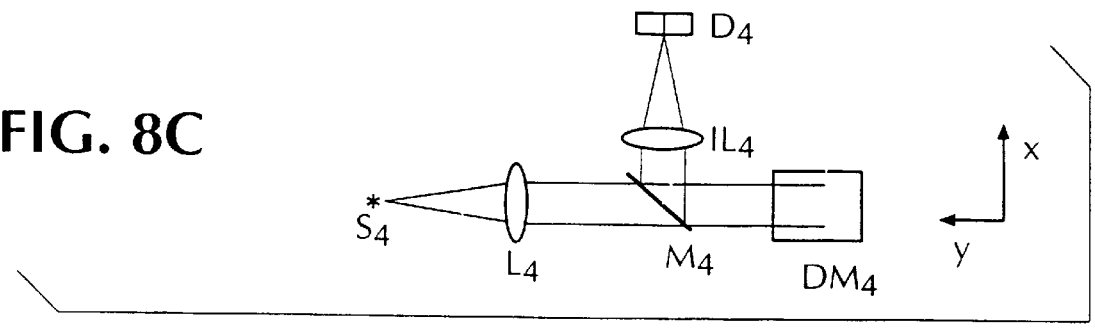
FIG. 8(c) is a top view of the ray path of a single beam autofocus.

One embodiment of a single-beam autofocus is provided in FIGS. 8 and 9, where a separate light source, $S_4$ of wavelength $\lambda_4$, and detector $D_4$ are shown. The wavelength $\lambda_4$ is necessarily distinct from the sample fluorescence, and preferentially a wavelength that cannot excite appreciable fluorescence in the sample. Thus, $\lambda_4$ is preferentially in the near infrared, exemplary 800–1000 nm. The partially transmitting, partially reflecting mirror, $DM_4$, is preferentially dichroic, reflecting $\lambda_4$ and transmitting $\lambda_n$ and $\delta\lambda_n$, n=1,2,3. Optically-based autofocus mechanisms suitable for the present application are known. For example, an astigmatic-lens-based system for the generation of a position error signal suitable for servo control is disclosed in *Applied Optics* 23 565–570 (1984). A focus error detection system utilizing a "skew beam" is disclosed in *SPIE* 200 73–78 (1979). The latter approach is readily implemented according to FIGS. 8 and 9, where $D_4$ is a split detector.

For use with a microtiter plate having a sample residing on the well bottom, the servo loop must, however, be broken to move between wells. This can result in substantial time delays because of the need to refocus each time the illumination is moved to another well.

Figure 10:
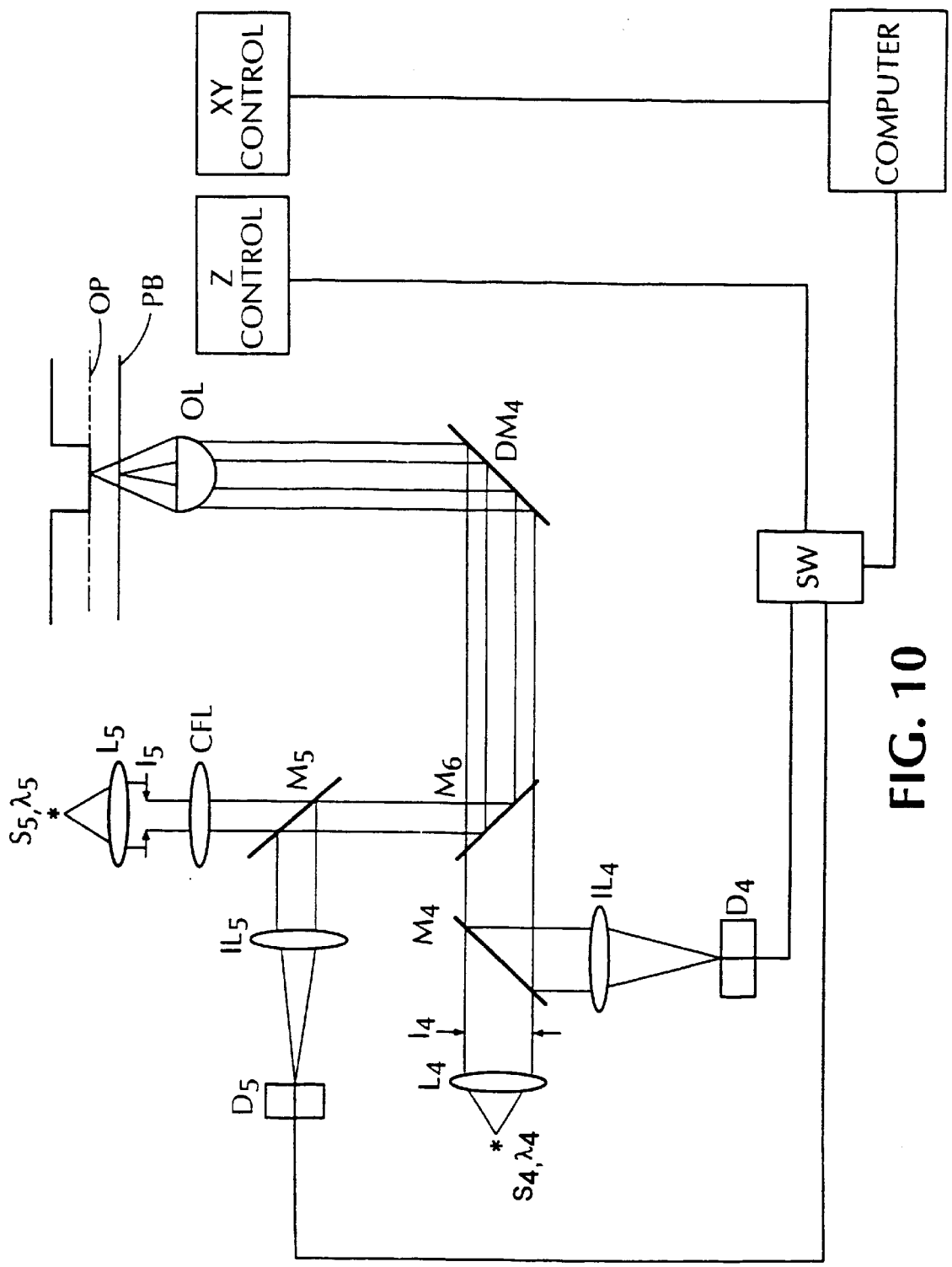
FIG. 10 is a side view of the two beam autofocus system.

Continuous closed-loop control of the relative position of the sample plane and the object plane is provided in a preferred embodiment of the present invention, depicted in FIG. 10. This system utilizes two independent beams of electromagnetic radiation. One, originating from $S_5$, is focused on the continuous surface, exemplary the bottom of a microtiter plate. The other, originating from $S_4$, is focused on the discontinuous surface, exemplary the well bottom of a microtiter plate. In one embodiment, the beams originating from $S_4$ and $S_5$ have wavelengths $\lambda_4$ and $\lambda_5$, respectively. $\lambda_4$ is collimated by $L_4$, apertured by iris $I_4$, and focused onto the discontinuous surface by the objective lens OL. $\lambda_5$ is collimated by $L_5$, apertured by iris $I_5$, and focused onto the continuous surface by the lens CFL in conjunction with the objective lens OL. The reflected light is focused onto the detectors $D_4$ and $D_5$ by the lenses $IL_4$ and $IL_5$, respectively. The partially transmitting, partially reflecting mirror, $DM_4$, is preferentially dichroic, reflecting $\lambda_4$ and $\lambda_5$ and transmitting $\lambda_n$ and $\delta\lambda_n$, n=1,2,3. The mirrors, $M_4$, $M_5$ and $M_6$, are partially transmitting, partially reflecting. In the case that $\lambda_4$ and $\lambda_5$ are distinct, $M_6$ is preferentially dichroic.

According to the embodiment wherein the sample resides in a microtiter plate, $\lambda_4$ is focused onto the well bottom. The object plane can be offset from the well bottom by a variable distance. This is accomplished by adjusting $L_4$ or alternatively by an offset adjustment in the servo control loop. For convenience of description, it will be assumed that $\lambda_4$ focuses in the object plane.

The operation of the autofocus system is as follows. If the bottom of the sample well is not in the focal plane of objective lens OL, detector $D_4$ generates an error signal that is supplied through switch SW to the Z control. The Z control controls a motor (not shown) for moving the microtiter plate toward or away from the objective lens. Alternatively, the Z control could move the objective lens. If the bottom PB of the microtiter plate is not at the focal plane of the combination of the lens CFL and the objective lens OL, detector $D_5$ generates an error signal that is applied through switch SW to the Z control. An XY control controls a motor (not shown) for moving the microtiter plate in the object plane OP of lens OL.

As indicated, the entire scan is under computer control. An exemplary scan follows: At the completion of an image in a particular well, the computer operates SW to switch control of the servo mechanism from the error signal generated by $D_4$ to that generated by $D_5$; the computer then directs the XY control to move the plate to the next well, after which the servo is switched back to $D_4$.

The "coarse" focusing mechanism utilizing the signal from the bottom of the plate is used to maintain the position of the sample plane to within the well-to-well variations in the thickness of the plate bottom, so that the range over which the "fine" mechanism is required to search is minimized. If, for example, the diameter of the iris $I_5$ is 2 mm and $IL_5$ is 100 mm, then the image size on the detector will be ~100 $\mu$m. Similarly, if the diameter of the iris $I_4$ is 0.5 mm and $IL_4$ is 100 mm, then the image size on the detector will be ~400 $\mu$m. The latter is chosen to be less sensitive so as to function as a "coarse" focus.

As with the single-beam embodiment described above, the wavelengths $\lambda_4$ and $\lambda_5$ are necessarily distinct from the sample fluorescence, and preferentially wavelengths that cannot excite appreciable fluorescence in the sample. Thus, $\lambda_4$ and $\lambda_5$ are preferentially in the near infrared, such as 800–1000 nm. In addition, the two wavelengths are preferably distinct, for example $\lambda_4$=830 nm, $\lambda_5$=980 nm.

In an alternative embodiment of two-beam autofocus, $\lambda_4=\lambda_1$ and the two beams may originate from the same source. Preferentially, the two beams are polarized perpendicular to one another and $M_6$ is a polarizing beamsplitter.

Pseudo-closed loop control is provided in the preferred embodiment of single-beam autofocus which operates as follows. At the end of a scan the computer operates SW to switch control to a sample-and-hold device which maintains the Z control output at a constant level while the plate is moved on to the next well after which SW is switched back to $D_4$.

DETECTION DEVICES

An essential feature of the disclosed apparatus is the use of a detection device having manifold, independent detection elements in a plane conjugate to the object plane. As discussed above, line illumination is advantageous principally in applications requiring rapid imaging. The potential speed increase inherent in the parallelism of line illumination as compared to point illumination is, however, only realized if the imaging system is capable of detecting the light emitted from each point of the sample along the illumination line, simultaneously.

It is possible to place a charge-coupled device (CCD), or other camera, at the output of the prior art imaging systems described above (White et al., U.S. Pat. No. 5,452,125 and Brakenhoff and Visscher, *J. Microscopy* 171 17–26 (1993)). The resulting apparatus has three significant disadvantages compared to the present invention. One is the requirement of rescanning the image onto the two-dimensional detector, which adds unnecessary complexity to the apparatus. Another is the requirement of a full two-dimensional detector having sufficient quality over the 1000 pixel×1000 pixel array that typically constitutes the camera. The third disadvantage is the additional time required to read the full image from the two-dimensional device.

The present invention is designed to avoid these disadvantages and optimize not only imaging speed, within the constraints of high-sensitivity and low-noise detection, but also throughput. One embodiment uses a continuous-read line-camera, and in a preferred embodiment a rectangular CCD is used as a line-camera. Both embodiments have no dead-time between lines within an image or between images. An additional advantage of the present invention is that a larger effective field-of-view is achievable in the stage-scanning embodiment, discussed below.

The properties required of the detection device can be further clarified by considering the following preferred embodiment. The resolution limit of the objective lens is <1 $\mu$m, typically ~0.5 $\mu$m, and the detector comprises an array of ~1000 independent elements. Resolution, field-of-view (FOV) and image acquisition-rate are not independent variables, necessitating compromise among these performance parameters. In general, the magnification of the optical system is set so as to image as large a FOV as possible without sacrificing resolution. For example, a ~1 mm field-of-view could be imaged onto a 1000-element array at 1-$\mu$m pixelation. If the detection elements are 20-$\mu$m square, then the system magnification would be set to 20×. Note that this will not result in 1-$\mu$m resolution. Pixelation is not equivalent to resolution. If, for example, the inherent resolution limit of the objective lens is 0.5 $\mu$m and each 0.5 $\mu$m×0.5 $\mu$m region in the object plane is mapped onto a pixel, the true resolution of the resulting digital image is not 0.5 $\mu$m. To achieve true 0.5-$\mu$m resolution, the pixelation would need to correspond to a region ~0.2 $\mu$m×0.2 $\mu$m in the object plane. In one preferred embodiment, the magnification of the imaging system is set to achieve the true resolution of the optics.

Figure 11C:
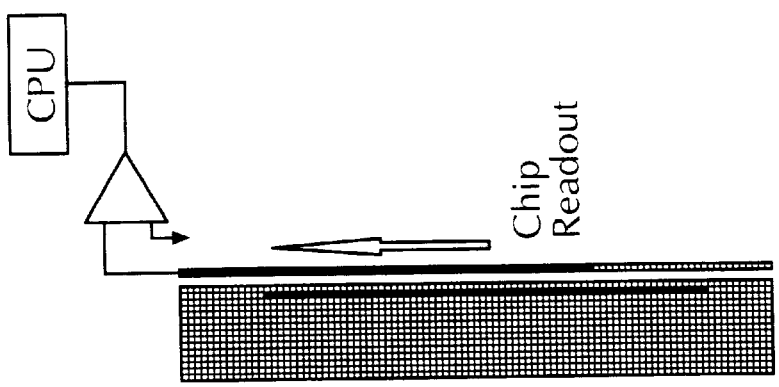
FIGS. 11(a)–11(c) illustrate the rectangular CCD camera and a readout register.
Figure 11B:
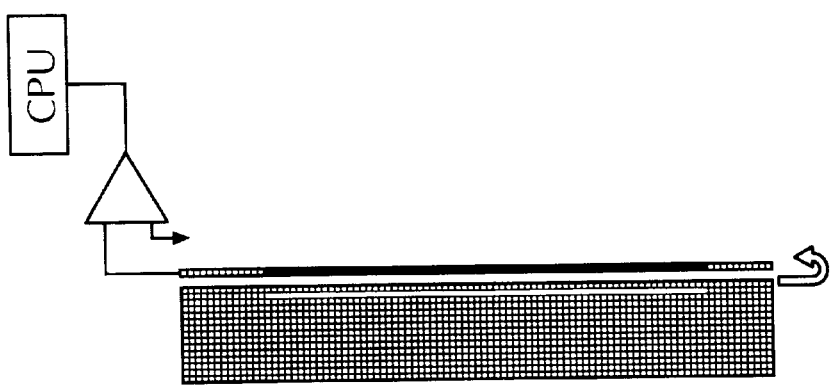
Figure 11A:
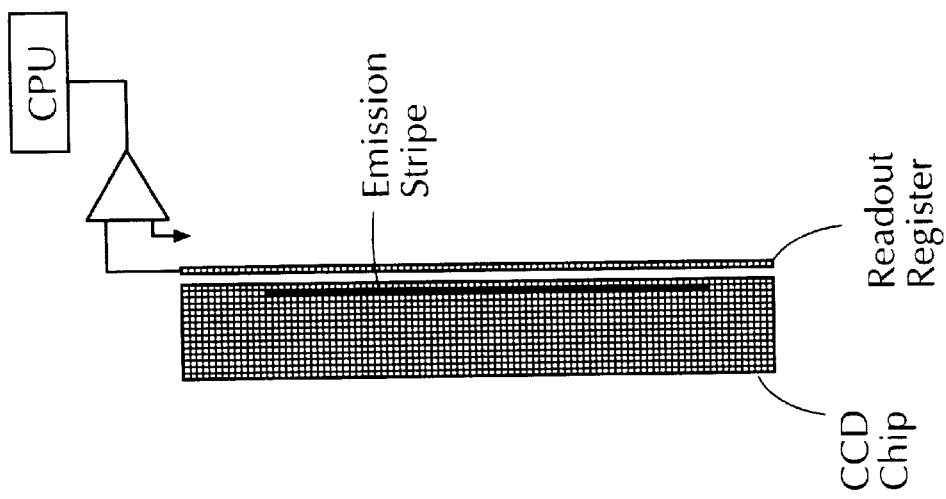

Presently, the highest detection efficiency, lowest noise detection devices having sufficient read-out speed for the present applications are CCD cameras. In FIG. 11, a rectangular CCD camera is depicted having an m×n array of detector elements where m is substantially less than n. The image of the fluorescence emission covers one row that is preferably proximate to the read register. This minimizes transfer time and avoids accumulating spurious counts into the signal from the rows between the illuminated row and the read-register.

In principle, one could set the magnification of the optical system so that the height of the image of the slit $SF_2$ on the CCD camera is one pixel, as depicted in FIG. 11. In practice, it is difficult to maintain perfect alignment between the illumination line and the camera row-axis, and even more difficult to maintain alignment among three cameras and the illumination in the multi-wavelength embodiment as exemplified in FIGS. 8 and 9. By binning together a few of the detector elements, exemplary two to five, in each column of the camera the alignment condition can be relaxed while suffering a minimal penalty in read-noise or read-time.

An additional advantage of the preferred embodiment having one or more rectangular CCD cameras as detection devices in conjunction with a variable-width detection spatial filter, $SF_2$ in FIGS. 8 and 9 and 510 in FIG. 6, each disposed in a plane conjugate to the object plane, is elucidated by the following. As discussed above, in one embodiment of the present invention the detection spatial filter is omitted and a line-camera is used as a combined detection spatial filter and detection device. But as was also discussed above, a variable-width detection spatial filter permits the optimization of the detection volume so as to optimize the sample-dependent signal-to-noise ratio. The following preferred embodiment retains the advantage of a line-camera, namely speed, and the flexibility of a variable detection volume. The magnification is set so as to image a diffraction-limited line of height h onto one row of the camera The width of the detection spatial filter d is preferably variable $h \leq d \leq 10$ h. The detectors in the illuminated columns of the camera are binned, prior to reading, which is an operation that requires a negligible time compared to the exposure- and read-times.

In one preferred embodiment, the cameras are Princeton Instruments NTE/CCD-1340/100-EMMD. The read-rate in a preferred embodiment is 1 MHz at a few electrons of read-noise. The pixel format is 1340×100, and the camera can be wired to shift the majority of the rows (80%) away from the region of interest, making the camera effectively 1340×20.

In addition to the above mentioned advantage of a continuous read camera, namely the absence of dead-time between successive acquisitions, an additional advantage is that it permits the acquisition of rectangular images having a length limited only by the extent of the sample. The length is determined by the lesser of the camera width and the extent of the line illumination. In a preferred embodiment the sample is disposed on the bottom of a well in a 96-well microtiter plate, the diameter of which is 7 mm. A strip 1 $\mu$m×1 mm is illuminated and the radiation emitted from the illuminated area is imaged onto the detection device. The optical train is designed such that the field-of-view is ~1 mm². According to the present invention, an image of the well-bottom can be generated at 1-$\mu$m pixelation over a 1×7-mm field.

ENVIRONMENTAL CONTROL

In an embodiment of the present invention, assays are performed on live cells. Live-cell assays frequently require a reasonable approximation to physiological conditions to run properly. Among the important parameters is temperature. It is desirable to incorporate a means to raise and lower the temperature, in particular, to maintain the temperature of the sample at 37 C. In another embodiment, control over relative humidity, and/or $CO_2$ and/or $O_2$ is necessary to maintain the viability of live cells. In addition, controlling humidity to minimize evaporation is important for small sample volumes.

Three embodiments providing a microtiter plate at an elevated temperature, preferably 37 C, compatible with the LCI system follow.

The imaging system preferably resides within a light-proof enclosure. In a first embodiment, the sample plate is maintained at the desired temperature by maintaining the entire interior of the enclosure at that temperature. At 37 C, however, unless elevated humidity is purposefully maintained, evaporation cooling will reduce the sample volume limiting the assay duration.

A second embodiment provides a heated cover for the microwell plate which allows the plate to move under the stationary cover. The cover has a single opening above the well aligned with the optical axis of the microscope. This opening permits dispensing into the active well while maintaining heating and limited circulation to the remainder of the plate. A space between the heated cover plate and microwell plate of approximately 0.5 mm allows free movement of the microwell plate and minimizes evaporation. As the contents of the interrogated well are exposed to ambient conditions though the dispenser opening for at most a few seconds, said contents suffer no significant temperature change during the measurement.

In a third embodiment, a thin, heated sapphire window is used as a plate bottom enclosure. A pattern of resistive heaters along the well separators maintain the window temperature at the desired level.

In additional embodiments, the three disclosed methods can be variously combined.

INTEGRATED DISPENSER

One embodiment of the video-rate configuration of the imaging system is further configured to initiate kinetic assays, in particular ion-channel assays, with a timed reagent dispense. Initiation of channel opening is accomplished by dispensing a solution into the micro well. For example, voltage-gated channels can be opened by addition of a solution of KCl to depolarize the plasma membrane. The time-dependence of the channel opening and subsequent closing and the corresponding change in intracellular concentration is often sufficiently rapid to require video-rate imaging. The intrinsic speed of the imaging system is irrelevant, however, unless the channel response can be initiated rapidly.

One embodiment of the present invention provides an integrated dispenser. For assays run in 96- or 384-well plates, addition volumes in this range 20–100 $\mu$L are desirable. A single head dispenser, as is appropriate, for example, to the addition of an agonist of ion-channel activity, is the IVEK Dispense 2000. Comparable units are available from CAVRO. More generally, it is desirable to be able to dispense a unique compound into each well. One embodiment provides a single head dispenser on a robotic motion device that shuttles the dispense head between the analysis station, the source plate containing the unique compounds and the tip cleansing station. The latter is a wash station for a fixed tip dispenser and a tip changing station for a disposable tip dispenser. This system provides the desired functionality relatively inexpensively, but it is low throughput, requiring approximately 30 seconds per compound aspiration-dispense-cleanse cycle. An alternative embodiment is provided by integrating a multi-head dispenser such as the Hamilton Microlab MPH-96 into the disclosed LCI system. The MPH-96 consists of 96 independent fixed tip dispensers mounted to a robotic motion device capable of executing the aspirate-dispense-wash cycle described above.

In an additional preferred embodiment of the invention, employed in automated screening assays, the imaging system is integrated with plate-handling robots, such as the Zymark Twister.

DARK FIELD CONFOCAL CONFIGURATION

Figure 12A:
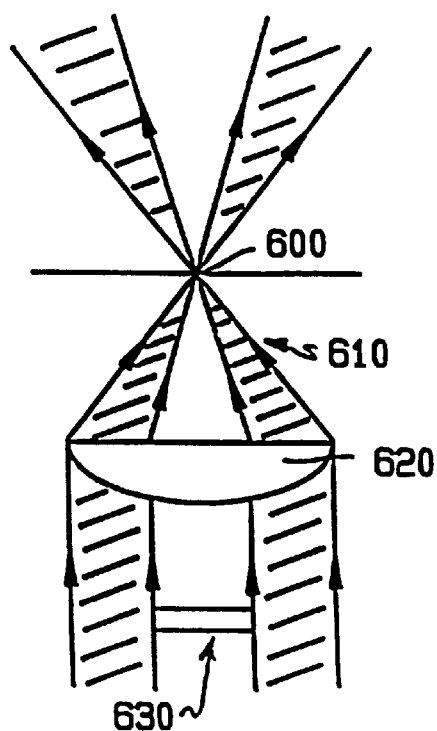
FIGS. 12(a) and 12(b) are cross-sectional views of ray paths formed by the line-scan confocal microscope in present invention employing conventional dark-field imaging.
Figure 12B:
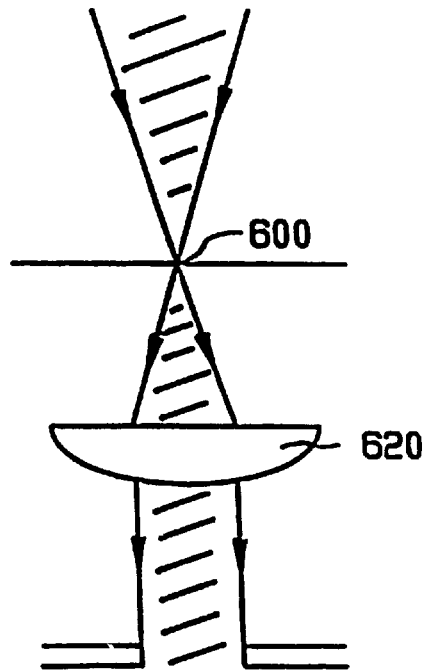

In the case that the desired lateral resolution is less than the diffraction limit, the background fluorescence due to the supernatant liquid can be decreased by an inventive application of the dark-field imaging technique. FIGS. 12(a) and 12(b) depict the ray paths in conventional dark-field. In FIG. 12(a), a sample 600 is illuminated by a hollow cone of light 610 from an objective lens 620. This cone of light is created, for example, by placing an opaque bar 630 at lens 440 in FIG. 10(a). In FIG. 12(b), the fluorescent emission from sample 600 is then collected through the center of the objective lens 620. Because of the differing angles of illumination and collection, the only plane which is both illuminated and detected is the plane containing sample 600.

Figure 13A:
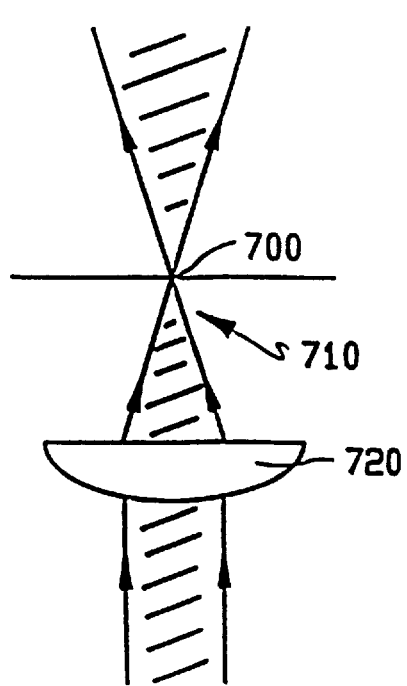
FIGS. 13(a) and 13(b) are cross-sectional views of ray paths formed by the line-scan confocal microscope in the present invention using inverse dark-field imaging.
Figure 13B:
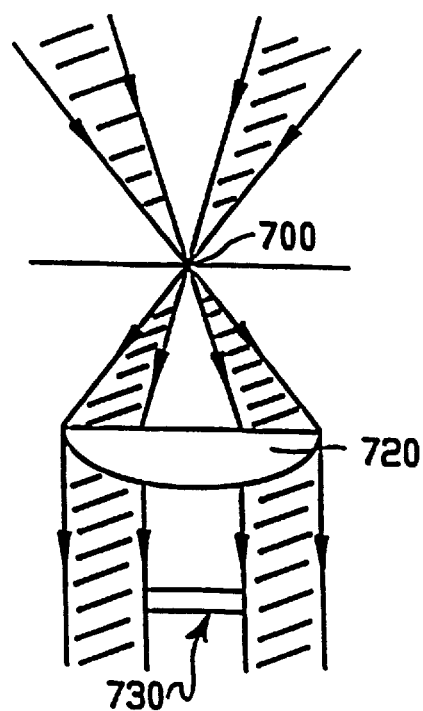

FIGS. 13(a) and 13(b) depict the ray paths in inverted dark-field. In FIG. 13(a), a sample 700 is illuminated with a beam of light 710 that passes through the center of an objective lens 720. In FIG. 13(b), fluorescent emissions are then collected only from around the outside of objective lens 720. Collection from around the outside of the objective may be achieved by placing, for example, an opaque bar 730 at lens 490 in FIG. 10(a). Like conventional dark-field, inverted dark-field involves illumination at one angle and collection at a different angle so that only the sample plane is both illuminated and detected.

Figure 14:
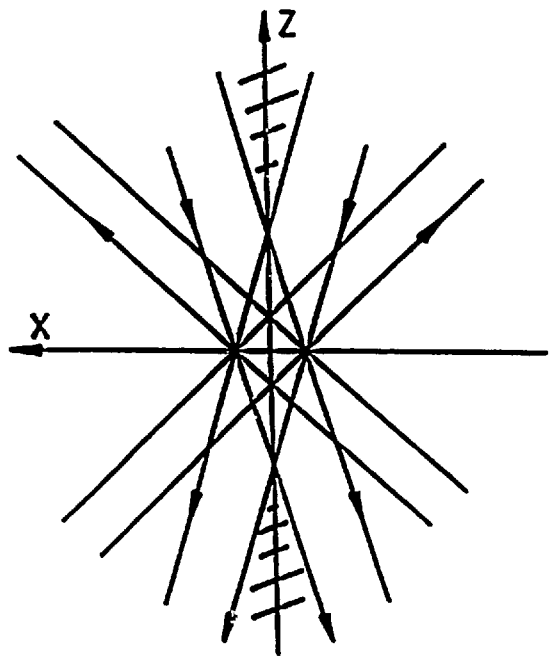
FIG. 14 is a cross-sectional view of ray paths formed by the line-scan confocal microscope in the present invention using inverse dark-field imaging, where an area larger than the diffraction-limited area of the sample plane is illuminated.

FIG. 14 depicts the focal region in the case described above where it is advantageous to illuminate a larger than diffraction-limited area of the sample plane. The illumination and collection rays are the same as those in the inverted dark-field geometry of FIG. 13. If a stop is placed in a plane conjugate to the objective back focal plane having a width matched to the illumination beam, the dark-field configuration is achieved. That this configuration confers a decrease in the out-of-plane fluorescence impinging on the detector can be understood from FIG. 14. The fluorescence from the shaded regions above and below the object plane is not passed by the stop. In point-scan confocal, fluorescence from these out-of-plane regions is rejected efficiently by the detection aperture. In line-scan confocal, the out-of-plane fluorescence from one lateral position along the line contributes to the background signal at other points along the line: this is the origin of the degradation in signal-to-background in line-scan relative to point-scan confocal. The inverse dark-field configuration of line-scan confocal recovers a significant fraction of the background rejection attributes of point-scan confocal while retaining the speed advantage of the linescan configuration.

REAL-TIME DATA ANALYSIS

The present invention is capable of generating megabytes of data per second, continuously. In one embodiment, the system is integrated with a fast high-density, high volume storage device to which the data can be spooled in real time for subsequent analysis. In a preferred embodiment, data analysis is run essentially simultaneously with data acquisition. Thus, the data is processed prior to storage. In general, only the results of the analysis are archived, but it is advantageous to archive selected raw data, as well.

Examples of real time analysis routines are provided below in conjunction with each of the assay groups. In all cases, procedures are used to optimize the software code for operation on the hardware platform of interest. In a presently preferred embodiment, the computer is a 32-bit processor such as the Pentium II. In this case, all data is accessed in 32-bit parcels.

In general the acquisition and analysis of the data comprises a number of discrete steps. First, the fluorescence is converted into one or more digital images in which the digital values are proportional to the intensity of the fluorescent radiation incident on each pixel of the detection device. Within this step a correction is made for the non-uniform response of the imaging system across the field of view wherein the background subtracted data are divided by a so-called flat-field file. Second, a binary bitmap is generated from one of the digital images in which all values meeting certain criteria are replaced by one, all values failing to meet the criteria are replaced by zero. In one embodiment, the criteria include a threshold value determined from the image itself. Third, the bitmap is searched for groups of contiguous value-one pixels. In one embodiment the groups are further tested against minimum- and/or maximum-size criteria. Fourth, for the qualified groups, the values of the corresponding pixels in the same image or in another image are summed and recorded, and the average and other statistical properties of the sums determined and recorded. Additions to and variations on this basic procedure appropriate to the various assays are disclosed below.

ASSAYS

Numerous variations of the assay methods described below can be practiced in accordance with the invention. In general, a characteristic spatial and/or temporal distribution of one or more fluorescently-labeled species is used to quantify the assay. Advantageously, the fluorescence is observed from an essentially planar surface using a line-scan confocal microscope. This section is organized by assay-type according generally to increasing degree of complexity in the associated data analysis routine. The organization is not strict, however, because the analysis algorithms are often applicable to more than one assay-type.

BINDING ASSAYS

A first assay-type that can be advantageously performed according to the methods of the present invention is a binding assay. In general, the degree of binding of a fluorescently-labeled ligand to the target of interest is quantified from the analysis of one or more fluorescence images of a sample containing at least the target and the labeled ligand and obtained with the disclosed line-scan confocal imaging system. The ligands utilized include, but are not limited to, fluorophore conjugated natural and synthetic peptides and proteins, sugars, lipids, nucleic acid sequences, viral particles, bacteriophage particles, natural and synthetic toxins, known pharmaceutical agents, small organic molecules or synthetic analogues of neuro-transmitters or intrinsically fluorescent small molecules, peptides or proteins, synthetic compounds from combinatorial libraries, random peptides, proteins from cDNA expression libraries, and peptidomimetics. (See Haugland R. P. Handbook of Fluorescent Probes and Research Chemicals $6^{th}$ Ed. Chap. 18.) The targets include, but are not limited to cellular extracts or purified preparations of receptors, ligand-gated and ion-gated channel proteins, enzymes, transcription factors, cytoskeletal proteins, and antibodies and can be derived from viruses, bacteria, bacteriophages, invertebrate and vertebrate cells. Exemplary receptors include but are not limited to acetylcholine, adrenergic ($\alpha$ and $\beta$), muscarinic, dopamine, glycine, glutamine, serotonin, aspartate, gamma-amino butyric acid (GABA), purinergic, histamine, norepinephrine, Substance P, Neuropeptide Y, enkephaline, neurotensin, cholecystokinin (CCK), endorphin (opiod), melanocrotin/ACTH, somatostatin, parathyroid hormone, growth hormone, thyrotropin, thyroxin, cytokine, chemokine, insulin, insulin-like growth factor (IGF), stem cell factor, Luteinizing hormone-releasing hormone, gonadotropin, angiotensin, endothelin, neurotensin, interferon, bradykinin, vasopressin, oxytocin, vasoactive intestinal polypeptide (VIP), corticotropin releasing-hormone, neurotrophin, erythropoetin, prostaglandin, leukotriene, thromboxane A2, calcitonin, T-cell, LDL/HDL, Epidermal growth factor (EGF), Estrogen, and Galainan.

BEAD-BASED BINDING

FIGS. 15(*a*)–15(*f*) depict the steps of an embodiment of a receptor-binding assay that can be performed according to the present invention. In FIG. 15(*a*), membranes 210 prepared from cells or tissues and containing the receptor target 212 are added to a well 220 containing a liquid 230. In FIG. 15(*b*), fluorescent-labeled ligands 214 are added to well 220; these ligands bind to the membrane receptors 212. In FIG. 15(*c*), beads 224 are added to the well 220. Alternatively, the order of 15(*b*) and 15(*c*) may be interchanged, and in a preferred embodiment, the membraneoated beads are prepared separately, prior to addition to the well. Beads 224 have a diameter in the range of approximately 1–20 µm and are coated with a material, such as wheat germ agglutinin, to which the membranes 210 adhere or have a surface that allows for the direct covalent or non-covalent binding of membranes.

Figure 15C:
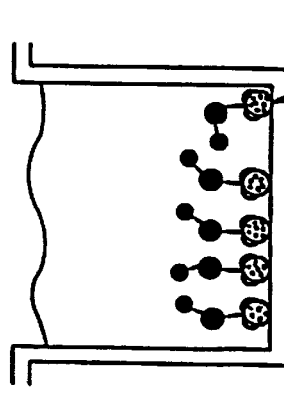
FIGS. 15(a)–15(f) illustrate a first embodiment of a receptor-binding assay according to the present invention.
Figure 15B:
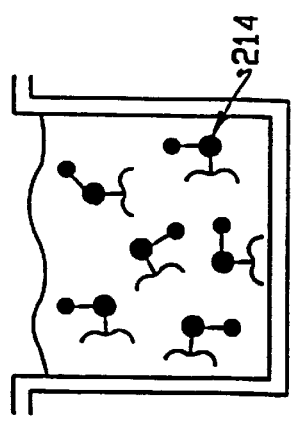
Figure 15A:
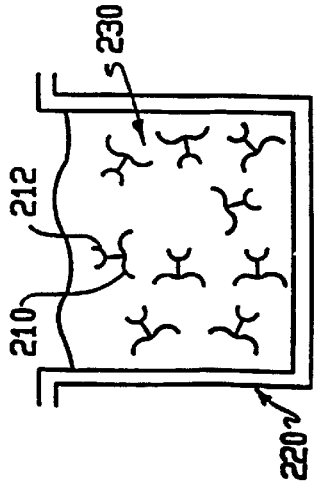
Figure 15F:
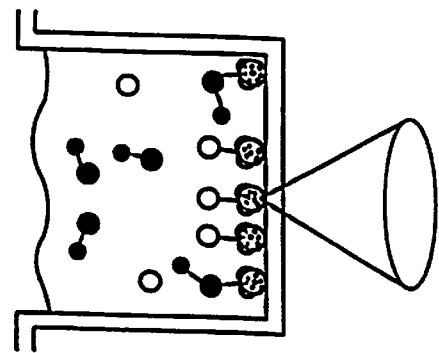
Figure 15E:
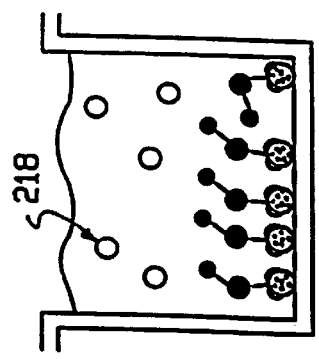

The foregoing steps are the same as those of the corresponding steps in the prior art SSA depicted in FIGS. 1(*a*)–1(*f*) except that the labels are fluorescent rather than radioactive. However, in the present invention, beads 224 are not luminescent and they have a density such that they sink to, or can be spun down to, the bottom of the well or are magnetic so that they can be moved to the bottom of the well using an external magnet In FIG. 15(d), the fluorescent labels are imaged using, for example, a line-scan confocal microscope schematically depicted as element 240. In FIG. 15(e), a test compound 218 is added to the well. As in the prior art assays, the purpose of the present assay is to determine the extent to which the test compound displaces the fluorescently-labeled ligands 214 from the membrane receptors 212. In FIG. 15(f), the fluorescent labels still bound to the membranes 210 are imaged. By comparing the two fluorescent images, the activity of the test compound can be determined.

Figure 15D:
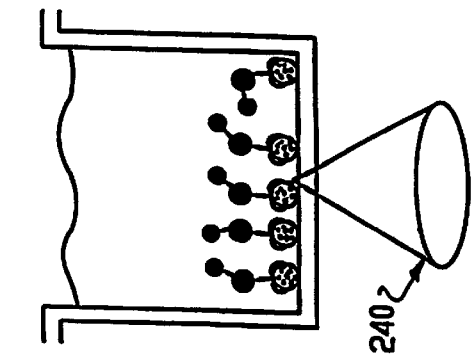

In an alternative embodiment of the assay depicted in FIGS. 15(a)–15(f), the imaging step depicted in FIG. 15(d) can be eliminated and the activity of the test compound can be determined by comparing the image obtained in FIG. 15(f) to the image of a control well or the image expected from the known quantity of the fluorescent-labeled ligands added to the well and their known affinity to the receptors.

In a specific embodiment of the assay depicted in FIGS. 15(a)–15(f), the receptor is an antibody that recognizes the ligand, and the fluorescently-labeled ligand is added to the reaction along with a sample containing an unknown amount of unlabelled ligand. As in prior art radioimmunoassays, the purpose of the present assay is to determine the concentration of unlabelled ligand in the sample by measuring extent to which it displaces the fluorescently-labeled ligands 214 from the antibody receptor.

SURFACE BINDING

Figure 16A:
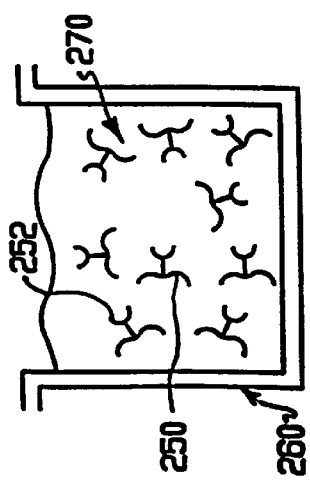
FIGS. 16(a)–16(f) illustrate a second embodiment of a receptor binding assay according to the present invention.
Figure 16B:
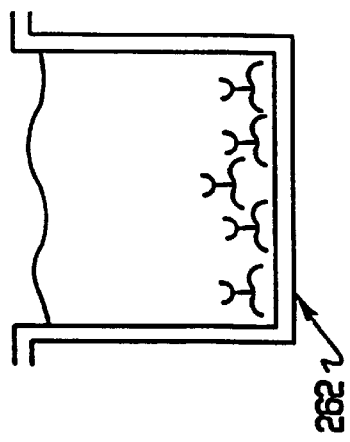
Figure 16C:
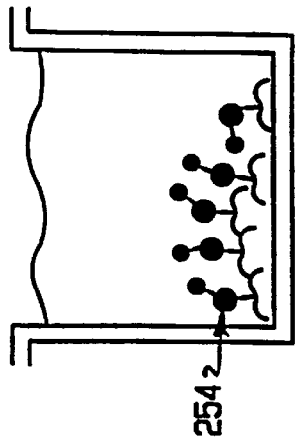

FIGS. 16(a)–16(f) depict the steps of a second embodiment of a receptor 10 binding assay according to the present invention. In FIG. 16(a), membranes 250 prepared from cells or tissues and containing the receptor target 252 are added to a well 260 containing a liquid 270. The well bottom 262 is coated with a material such as wheat germ agglutinin, to which the membranes adhere. In FIG. 16(b), membranes 250 are shown bound to this material. In FIG. 16(c), fluorescently-labeled ligands 254 are added to well 260 and bind to the membrane receptors 252. Alternatively, the order of FIGS. 16(b) and 16(c) may be interchanged.

Figure 16D:
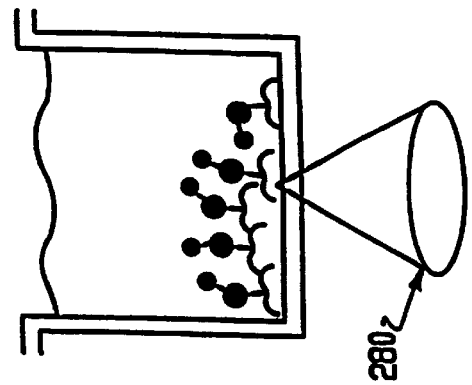
Figure 16E:
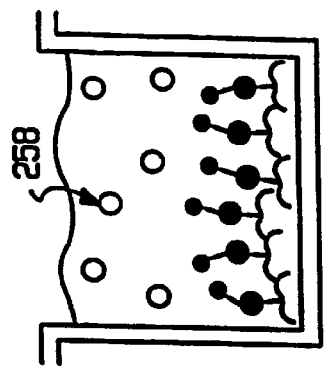
Figure 16F:
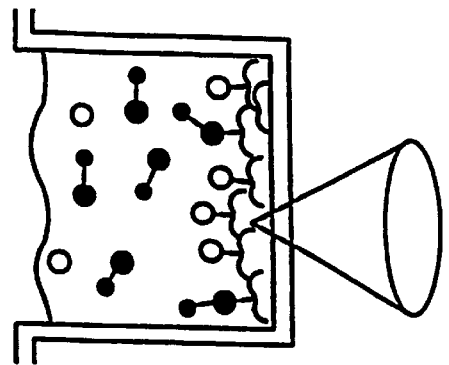

In FIG. 16(d), the fluorescence of the fluorescent labels is imaged using, for example, a line-scan confocal microscope schematically depicted by element 280. In FIG. 16(e), a test compound 258 is added to well 260. In FIG. 16(f), the fluorescent labels still attached to the membranes 250 are imaged and compared to the first image to determine the activity of test compound 258.

In an alternative embodiment of the assay depicted in FIGS. 16(a)–16(f), the imaging in FIG. 16(d) can be eliminated and the activity of the test compound can be determined by comparing the image obtained in FIG. 16(f) to the image of a control well or the image expected from the known quantity of the fluorescent-labeled ligands added to the well and their known affinity to the receptors.

CELL-BASED BINDING

In an alternative embodiment, ligand-target binding is advantageously assayed on collections of cells expressing the target. In general, there are a number of advantages to cell-based assays for screening chemical compounds. In particular, the activity of interest is measured in the presence of both competing and complementary cellular processes affecting the biological activity of the compound. In cellular assays, cells prepared from cell lines or tissues are placed in tissue culture wells or on microscope slides. The cells can be live and intact or permeabilized with reagents such as digoxigenin, or, alternatively, fixed with reagents such as formaldehyde. One or more fluorescent-labelled ligands are added to the cells along with any non-fluorescent reagents required for the assay; the fluorescent-labelled ligands bind to one or more components of the cells. A test compound is then added to the cells. Alternatively, the order of addition of fluorescent ligands and chemical compounds may be interchanged. The fluorescent labels are imaged using, for example, a line-scan confocal microscope schematically depicted as element 240. The purpose of the present assay is to determine the extent to which the test compound displaces the fluorescently-labeled ligands from the receptors. The fluorescent labels still bound to the cells are imaged in the presence and the absence of test compound. By comparing the two fluorescent images, the activity of the test compound can be determined.

In an alternative embodiment of a cell-based receptor binding assay, the imaging step in the absence of compound can be eliminated and the activity of the test compound can be determined by comparing the image obtained in the presence of compound to the image of a control well or the image expected from the known quantity of the fluorescent-labeled ligands added to the well and their known affinity to the receptors.

ADVANTAGES OF LINESCAN CONFOCAL IMAGING IN BINDING ASSAYS

In a first embodiment, ligand-target binding is performed with one excitation wavelength and one emission wavelength. Data are provided in FIG. 27 exemplifying the speed and sensitivity of the present invention. A detailed analysis of its performance relative to the prior art wherein ligands are radio-labeled to allow for their detection, follows. The prior art for receptor-ligand assays includes SSA formats as well as formats in which bound and unbound ligand are physically separated and the amount of ligand bound to the receptor is measured by the addition of liquid scintillant.

First, the present invention can be used in small-volume wells, exemplary 1 $\mu$L. In a receptor-ligand binding assay employing radio-labeled ligand, each radio label, $^3$H for example, can decay only once, producing at most 90 photons per decay, at a decay rate of less than $10^{-8}$ per second. A single fluorescent molecule, will produce $10^4$–$10^7$ photons in total, and it will emit between $10^3$ and $10^6$ photons per second. Thus, the count-rate for a fluorescent label is approximately $10^{11}$ relative to $^3$H. The present invention, therefore, requires immensely fewer labels, membranes and beads per well. For example, while a tritium SSA requires $10^7$ beads per well, the present invention requires less than $10^3$ beads per well. As a result, the present invention can be performed in $\mu$L-volume wells and in far less time. In addition, in an SSA it is difficult to alter the imaging time, because radio labels decay at a fixed rate. In contrast, the excitation rate of fluorescent labels can be increased so as to increase the photon emission rate, thereby reducing the required imaging time. The excitation rate cannot, however, be increased without limit. In fact, it is the existence of the so-called saturation limit of the fluorophore emission rate that underlies the substantial advantage of the line-scan confocal over the point-scan confocal in the present application. Second, the present invention does not require the time and expense of handling radioactivity. Third, because the present invention can be performed in small-volume wells, the compound and reagent consumption is much lower than for SSAs resulting in further cost reductions. Finally, the present invention does not require scintillant-doped beads or well bottoms, reducing costs even further.

The present invention uses a line-scan confocal microscope to image the fluorescence of the sample in the well.

The confocal aspect of the microscope allows for optical sectioning, i.e., detection of fluorescence from the plane in which the sample is located while minimizing the detection of fluorescence from the bulk of the solution. This eliminates the need for wash steps to remove unbound fluorescent-labeled ligand; this step, while it is not required in an SSA, is still required in any receptor-ligand binding assay, including RIA, in which scintillant containing beads are not used. The confocal aspect of the microscope also eliminates any interference that may originate from intrinsic fluorescent test compounds. The line-scan aspect allows the sample to be imaged more rapidly than in traditional point-scanning without losing appreciable background rejection. The speed increase depends on the fluorophore density, the lateral resolution, the field of view, and parameters of the hardware including the objective NA, the detection sensitivity and camera read-rate. Theoretically, the speed increase can approach the number of pixels per line, which is 1000 in a preferred embodiment of the present invention. Practically, the increase is approximately 100×.

In order to quantify these advantages, an exemplary sample will be described. The assay is cell-based, wherein the location of the fluorescence is to be resolved to a precision of 1 $\mu$m. Thus the image of a 1-mm diameter sample area will consist of ~$10^3$ lines of ~$10^3$ pixels. The fluorescence signal of interest might originate from ligands on the cell surface or from a localized source within the cell, such as a receptor in the nucleus. In either case, the local concentration of the fluorophore is the important parameter. For an engineered cell line expressing ~$10^5$ receptors per cell, the cell-averaged concentration is ~1 $\mu$M. A few thousand receptors localized in the nucleus results in a comparable local concentration. Consistent with the desired lateral resolution of 1 $\mu$m, there are ~$2 \times 10^3$ fluorophores per pixel. It is assumed that the intrinsic cellular background fluorescence is less than, but on the order of, the label fluorescence, and that the desired signal-to-noise ratio is minimally 10. Then, the number of detected photons needs to be nearly $10^3$, taking into account the shot noise of the signal and background and the read noise of a high quality solid state detector. The collection and detection efficiency of the present device, using an approximately 0.7 NA objective, blocking filters, and a solid state camera is ~1%, requiring that ~$10^5$ photons be emitted per pixel, or ~$10^2$ photons per molecule. It is desirable that the image be acquired in less than 1 second, preferably in a fraction of a second. If the pixels are acquired in a serial fashion, then the pixel dwell-time must be less than 1 $\mu$s, requiring a photon emission rate of greater than $10^8$ per second per molecule. This is beyond the saturation value of most fluorophores, which is typically $10^6$. Importantly, the flux required to achieve saturation, $10^5$–$10^6$ W/cm$^2$, is sufficient to drive non-linear photo-induced bleaching of the fluorophores, as well. Finally, the highest efficiency detection devices cannot be used at the data rates required in serial scanning. By contrast, the emission rate per fluorophore need only be ~$10^5$ if $10^3$ pixels are illuminated simultaneously. The increased rejection of background fluorescence of point-scan confocal does not warrant the disadvantage of dramatically decreased scan speed.

The exemplary data of FIG. 27 demonstrate that the disclosed system has sufficient sensitivity to quantify tens of fluorophores per bead, while clearly resolving hundreds of individual beads in less than 1 second. Comparable data can be acquired in cell-based binding experiments, as will be exemplified below.

DATA ANALYSIS

The data analysis routines are closely related whether the binding be cell-based or bead-based and are presented together, below. The data can be analyzed by the following routines, the simplest of which is the Threshold Image Analysis algorithm. The purpose of the routine is to determine the amount of a fluorescently-labeled species that is localized in a contiguous or punctuate manner so as to exceed a minimum fluorescence intensity, and optionally so as to not exceed a maximum fluorescence intensity. In one embodiment the analysis is used to assay the activity of a chemical compound.

The steps of the algorithm are as follows:
1. Acquire a digitized image of the labeled species.
2. Open file row-by-row and
    i. Subtract camera offset value from image,
    ii. Multiply each row in the image by the inverse of the corresponding row in the flat-field image file.
3. Optionally, histogram the image to determine the background level.
4. Establish selection criteria including a minimum value and optionally a maximum value. The values are determined, for example, as a fixed multiple of the mean background level, as a fixed number of counts above the mean background level, by statistical analysis on the background histogram peak width or by using a predetermined value.
5. Compare each pixel in the image to the selection criteria. For each pixel in the image meeting the criteria, add the value to a running sum. The total number of qualified pixels and the average intensity are reported.

This routine is used advantageously to process data similar to that in FIG. 27, in which the individual beads are clearly distinguishable from the background and the artefacts due to clumped beads or cells are small. Such a routine is appropriate for the assay-type having membranes bound to the well bottom, as well.

A second routine applicable to analyzing binding data is the Localization Analysis algorithm which entails an additional shape analysis protocol. As with the Threshold routine, the purpose is to determine the amount of a fluorescently-labeled species that is localized in a contiguous or punctuate manner. In one embodiment the analysis is used to assay the activity of a chemical compound.

The steps of the algorithm are as follows:
1. Acquire image of the labeled species.
2. Open file row-by-row and
    i. Subtract camera offset value from the image,
    ii. Multiply each row in the image by the inverse of the corresponding row in the flat-field image file.
3. Optionally, histogram and sum the pixel values of the image.
4. Establish selection criteria including a minimum value and optionally a maximum value. The values are determined, for example, as a fixed multiple of the mean background level, as a fixed number of counts above the mean background level, by statistical analysis on the background histogram peak width or by using a predetermined value.
5. Compare each pixel in the image to the selection criteria. All qualified pixels are assigned a value of 1 and all others are assigned a value of 0, thereby effecting a 16- to 1-bit compression.
6. "Clean" the edge of the image by setting to 0 all 1-valued contiguous pixels in the binary mask having an edge-touching member.

7. Search the bitmap for objects, defined as groups of contiguous value-1 pixels, by:
   i. Searching the image in a line-by-line pattern to find a pixel of value 1.
   ii. Determining all value-1 pixels contiguous to the pixel identified in i).
   iii. Optionally, applying a minimum and maximum size filter to the object, the sizes having been previously determined.
   iv. If the object qualifies, proceed to step 8, otherwise change all 1-valued pixels in the object to 0 and continue searching for next object.
   v. If the end of the bitmap is reached, proceed to step 9.
8. For each object passing the filter criteria:
   i. Optionally, create a new rectangular bitmap with extended borders that contains the object plus n extra 0 pixels in each direction from the edge of the object. n is the number of dilation steps to be performed below and has been previously determined.
   ii. If step 8.i. was implemented, then dilate the object by applying a dilation step n times in which pixels of value 0 that touch 1-valued pixels are set to value 1.
   iii. For each collection of 1-valued pixels in either the dilated bitmap, or in the original bitmap if step 8.i. was not implemented, sum and average the corresponding pixel values from the image to calculate the average pixel intensities under the mask.
   iv. Change to 0 all pixels of the object in the original bitmap image and return to step 7 to search for more objects.
9. After all objects have been counted, the average intensity of the fluorescently-labeled species per object and optionally the fraction of the total intensity of the species localized is calculated for all objects in the image and reported together with statistical information such as the standard deviation.

The distinguishing operation in this routine, shared by all the following algorithms, is the creation of the binary mask in steps 4–6. Mask generation is depicted in FIG. 20. The selection criteria of objects for the mask can optionally include minimum and maximum values, size and shape. For example, in one embodiment, the analysis routine for the bead-based assays include a roundness filter in step 7.iii.

In a second embodiment, the emission of two or more fluorescently-labeled species is detected simultaneously, excited by one or more illumination wavelengths. As applied in a binding assay, the first fluorescently-labeled species is used to identify the object to which the second fluorescently-labeled species binds. Two examples of two-color cell-based binding assays are provided in FIGS. 24 and 26. An exemplary procedure that can be used to analyze such images is the Co-localization Analysis routine which is designed to determine the amount of a first fluorescently-labeled species localized with respect to a second fluorescently-labeled species. In one embodiment the analysis is used to assay the activity of a chemical compound, for example, where activity depends on a subcellular localization of interest. The steps of the algorithm are as follows:

1. Acquire digitized images of the first and second labeled species respectively.
2. Open files row-by-row and
   i. Subtract respective camera offset values from each image,
   ii. Multiply each row in each image by the inverse of the corresponding row in its respective flat field image file.
3. Optionally, histogram the image of the first species to determine the background level and sum the intensity of the image of the second species.
4. Establish selection criteria including a minimum value and optionally a maximum value. These values are determined, for example, as a fixed multiple of the mean background level, as a fixed number of counts above the mean background level, by statistical analysis on the background histogram peak width or by using a predetermined value.
5. Compare each pixel in the image of the first species to the selection criteria All qualified pixels are assigned a value of I and all others are assigned a value of 0, thereby effecting a 16- to 1-bit compression.
6. "Clean" the edge of the image by setting to 0 all 1-valued contiguous pixels in the binary mask having an edge-touching member.
7. Search the bitmap for objects, defined as groups of contiguous value-1 pixels, by:
   i. Searching the image in a line-by-line pattern to find a pixel of value 1.
   ii. Determining all value-1 pixels contiguous to the pixel identified in i).
   iii. Optionally, applying a minimum and maximum size filter to the object, the sizes having been previously determined.
   iv. If the object qualifies, proceed to step 8, otherwise change all 1-valued pixels in the object to 0 and continue searching for next object.
   v. If the end of the bitmap is reached, proceed to step 9.
8. For each object passing the filter criteria:
   i. Optionally, create a new rectangular bitmap with extended borders that contains the object plus n extra 0 pixels in each direction from the edge of the object. n is the number of dilation steps to be performed below and has been previously determined.
   ii. If step 8.i. was implemented, then dilate the object by applying a dilation step n times in which pixels of value 0 that touch 1-valued pixels are set to value 1.
   iii. For each collection of 1-valued pixels in either the dilated bitmap, or the original bitmap if step 8.i. was not executed, sum and average the corresponding pixel values from the image of the second species to calculate the average pixel intensities under the mask.
   iv. Change to 0 all pixels of the object in the original bitmap image and return to step 7 to search for more objects.
9. After all objects have been counted, the average intensity of the second fluorescently-labeled species per object and optionally the fraction of the total intensity of the second species co-localized with the first species is calculated for all objects in the image and reported together with statistical information such as the standard deviation.

The advantage of this more elaborate routine is that the object, whether it be a cell or a bead, can be independently identified. As exemplified in FIG. 24, not all cells respond. The independent identification of cells, enables, for example, the ratio of responding to non-responding cells to be tabulated along with the degree of response among those that respond. This algorithm, despite its additional complexity, can be implemented so as to analyze 1-Megapixel images in under 1 second on a Pentium II platform.

TRANSLOCATION ASSAYS

An additional assay-type that can be performed advantageously according to the second embodiment, that is where the emission of two or more fluorescently-labeled species is detected simultaneously, excited by one or more illumination wavelengths, is the translocation assay. In these assays, the translocation of interest is of one or more species, which may be proteins, lipids or other molecular complexes or sub-cellular structures such as vesicles, from one well-defined region of a cell to another. These include but are not limited to: synaptin (vesicle membrane protein), transcription factors (NF-κB, NFAT, AP-1), hormone receptors, LDL/HDL receptors, Tcell receptors, and PTH receptors.

The prototypical translocation assay is a special case of the co-localization measurement. Exemplary, the co-localization of the first and second species is quantified by the fraction of the second species co-localized with respect to the first, or the ratio of the second species co-localized with the first and that resident elsewhere in the cell. An expanded analysis routine preferentially used to process translocation image data is provided below.

Exemplary translocation images and analysis procedures are provided in FIGS. 19–21. The labeled location is the cell nucleus, the label being a fluorophore specific for DNA, such as Hoechst 33342. Other nucleic acid specific stains are known in the art (e.g., see Haugland, R. P. Handbook of Fluorescent Probes and Research Chemicals, $6^{th}$ Ed. Chapter 8). The second species is a transcription factor whose migration from the cytoplasm to the nucleus is the subject of the assay. This protein can be labeled by a variety of methods, including expression as a fusion with GFP, and contacting the sample with a fluorescently-labeled antibody specific to the transcription factor protein.

The following Translocation Data Analysis routine can be used to determine the amount of a first fluorescently-labeled species that is distributed in a correlated or anti-correlated manner with respect to a second fluorescently-labeled species. In one embodiment the analysis is used to assay the activity of a chemical compound.

The steps of the algorithm are as follows:

1. Acquire images of the first and second labeled species respectively.
2. Open files row-by-row and
   i. Subtract respective camera offset values from each image,
   ii. Multiply each row in each image by the inverse of the corresponding row in its respective flat-field image file.
3. Optionally, histogram the image of the first species to determine the background level and sum the intensity of the image of the second species.
4. Establish selection criteria including a minimum value and optionally a maximum value. These values are determined, for example, as a fixed multiple of the mean background level, as a fixed number of counts above the mean background level, by statistical analysis on the background histogram peak width or by using a predetermined value.
5. Compare each pixel in the image of the first species to the selection criteria. All qualified pixels are assigned a value of 1 and all others are assigned a value of 0, thereby effecting a 16- to 1-bit compression.
6. "Clean" the edge of the image by setting to 0 all 1-valued contiguous pixels in the binary mask having an edge-touching member.
7. Search the bitmap for objects, defined as groups of contiguous value-1 pixels, by:
   i. Searching the image in a line-by-line pattern to find a pixel of value 1.
   ii. Determining all value-1 pixels contiguous to the pixel identified in i).
   iii. Optionally, applying a minimum and maximum size filter to the object, the size having been previously determined.
   iv. If the object qualifies, proceed to step 8, otherwise change all 1-valued pixels in the object to 0 and continue searching for next object.
   v. If the end of the bitmap is reached, proceed to step 9.
8. For each object passing the filter criteria:
   i. Create a new rectangular bitmap with extended borders that contains the object plus n extra 0 pixels in each direction from the edge of the object. n is the number of dilation steps to be performed below and has been previously determined.
   ii. Dilate the object by applying a dilation step n times in which pixels of value 0 that touch 1-valued pixels are set to value 1.
   iii. Compare the dilated bitmap with the original full size bitmap. Set to 0 all pixels in the dilated bitmap that are 1-valued in the corresponding region of the original bitmap. This produces an annular mask and ensures only one object is captured when the bitmap borders were increased during dilation.
   iv. Create another bitmap from the original object, erode it m times by setting to 0 value-1 pixels touching value-0 pixels. m is typically equal to n and determined previously.
   v. For each collection of 1-valued pixels in the annular and eroded bitmaps, average the corresponding pixel values from the image of the second species to calculate the average pixel intensities under the eroded and annular masks.
   vi. Calculate the ratio of eroded to annular intensities for each object and save in a table.
   vii. Change to 0 all pixels of the object in the original bitmap image and return to step 7 to search for more objects.
9. After all objects have been counted, the average intensity ratio of all objects in the image is calculated along with statistical information such as the standard deviation.

The new feature of this routine over those disclosed above is the creation in Step 8 of two daughter masks, one an annular extension of the primary mask, and one an eroded version of the primary mask. The latter is used to quantify the co-localization of species-two with species-one, the transcription factor and the cell nucleus (actually, DNA), respectively, in the present example. The former mask is used to quantify species-two not co-localized. In the present example, the ratio of these two quantities is formed on an cell-by-cell basis and the results tabulated.

According to the methods of the present invention, the data acquisition and analysis can be performed in approximately one second. For comparison, two prior art examples are cited. In Ding et al. (J. Biol. Chem, 273, 28897–28905 (1998)), a comparable two-color translocation assay was performed. The advantages of the present invention include: 1) approximately 50× faster image acquisition per data channel, 2) simultaneous two-color image acquisition, 3) superior sensitivity of approximately 10×, permitting lower staining levels, 4) confocal detection, allowing elimination of a rinse step, 5) focus-time of approximately 0.1 s compared to approximately 30 s, 6) data analysis time of approximately 0.2 s/frame compared to 3–6 s/frame, and 7) continuous image acquisition. The second example of prior art is Deptala et al. (Cytometry, 33, 376–382, (1998)). The present invention provides 1) higher spatial resolution, approximately 4×, 2) approximately 16× higher pixel acquisition rates, 3) faster data analysis, 4) autofocus operable in microtiter plates, and 5) data analysis time of approximately 0.2 s/frame compared to 3–6 s/frame.

ENDOCYTOSIS, EXOCYTOSIS AND RECEPTOR SEQUESTRATION

Endocytosis and exocytosis, generally, and receptor sequestration and recycling, specifically, are additional processes that can be assayed according to the first or second embodiments and the associated image analysis protocols disclosed above. Fluorescence labeling can be accomplished according to a variety of known methods. For example, an elegant experiment comprising the labeling of both the receptor and ligand is disclosed by Tarasova et al. (J. Biol. Chem., 272, 14817–14824 (1997)). The present imaging system is approximately 50× faster per data channel and acquires the two images simultaneously. In addition, the present analysis protocols, the Co-localization algorithm for example, can be used to process sequestration image data in real-time. No such examples are known in the prior art.

Many other assays requiring similar imaging and analysis capabilities are known in the art. For example, assays involving phagocytosis and related cellular events, (e.g., J. Immunology, (1983) 130, 1910; J. Leukocyte Biol. (1988) 43, 304); additional assays involving both receptor-mediated and non-receptor-mediated endocytosis and exocytosis (e.g. Neuron 14, 983 (1995); J. Physiol. 460, 287 (1993) and Science 255, 200 (1992), including receptor-mediated endocytosis of Low-Density Lipoprotein Complexes (see J. Cell Biol. 121, 1257 (1993) and the delivery of Transferin to vertebrate cells (see Cell 49, 423 (1994)); imaging the endocytosis and lateral mobility of fluorescently-labeled epidermal growth factor (see Proc. Natl. Acad. Sci. USA 75, 2135 (1975); J. Cell Biol. 109, 2105 (1989)); monitoring the uptake and internal processing of exogenous materials by endocytosis of fluorescent dextrans (see J. Biol. Chem. 269, 12918 (1994)), and the imaging of the endocytosis-mediated recycling of synaptic vesicles in actively firing neurons by use of hydrophilic dyes (see Nature 314, 357 (1985)). In addition, the genetic engineering of cell lines expressing green fluorescent protein (GFP)fused to proteins that localize to exocytotic and secretory vesicles (such as chromogranin B, a secretory granule protein (see J. Cell Sci. 110, 1453 (1997) or tPA which is localized to growth cones in differentiated neuronal cells (see Mol. Biol. Cell 9: 2463 (1998)) allow for the monitoring of exocytosis. A wide variety of fluorescent labels are available for such assays (See Haugland R. P. Handbook of Fluorescent Probes and Research chemicals, $6^{th}$ Ed. Chap. 17).

ION CHANNELS

A third embodiment of the present invention, one version of which is depicted in FIG. 9, can be used to image the time-dependent response of one or more fluorescently-labeled species at a rate of approximately 30 frames per second. This permits the capture of transient phenomenon, such as the opening and closing of ion channels. Exemplary ion channels include but are not limited to: $K^+$-gated voltage, $Na^+$-gated voltage, $Ca^{++}$-gated voltage, $Cl^-$, $Na^+/K^+$ATPase, and P-glycoproteins.

The following Kinetic Imaging Data Analysis algorithm defines and tracks individual cells from frame to frame, enabling simultaneous kinetic analysis on a sufficient number of cells to obtain statistically meaningful data. The steps of the algorithm are as follows:

1. Acquire one (indicator only), two (marker and indicator or two indicators) or more digitized images as a function of time.
2. Open files row-by-row and
   i. Subtract respective camera offset values from each image,
   ii. Multiply each row in each image by the inverse of the corresponding row in its respective flat-field image file. Subtract respective camera offset values from each image.
3. Optionally, histogram the image of the first species to determine the background level.
4. Establish selection criteria including a minimum value and optionally a maximum value. The values are determined, for example, as a fixed multiple of the mean background level, as a fixed number of counts above the mean background level, by statistical analysis on the background histogram peak width or by using a predetermined value.
5. Compare each pixel in the image of the first species to the selection criteria. All qualified pixels are assigned a value of 1 and all others are assigned a value of 0, thereby effecting a 16- to 1-bit compression.
6. "Clean" the edge of the image by setting to 0 all 1-valued contiguous pixels in the binary mask having an edge-touching member.
7. Search the bitmap for objects, defined as groups of contiguous value-1 pixels, by:
   i Searching the image in a line-by-line pattern to find a pixel of value 1.
   ii Determining all value-1 pixels contiguous to the pixel identified in i.
   iii. Optionally, applying a minimum and maximum size filter to the object, the size having been previously determined.
   iv. If the object qualifies, proceed to step 8, otherwise change to 0 all 1-valued pixels in the object and continue searching for next object.
   v. If the end of the bitmap is reached, proceed to step 9.
8. For each object passing the filter criteria: average the corresponding pixels from each of the images in the time series. If a single indicator is used, record the intensities. If ratiometric indicators are used, divide the value of one image by the other for each image in the time series and record the results.
9. After all objects have been analyzed, the results of the analysis of step 8 are reported for each object. Kinetic parameters, including the rise time, fall time and amplitude are reported for each object as are statistical information derived from the set of kinetic analyses and from the set of all objects at fixed times.

Two examples of the use of the present invention to image and analyze transient events associated with ion channels are provided in FIGS. 22 and 23. These assays used the $Ca^{++}$-sensitive dye, Fluo-3 to indicate the changes in intra-cellular $Ca^{++}$ concentration. In the first of the experiments, the change was caused by a $Ca^{++}$ second signal initiated by the activation of acetylcholine receptors, and in the second experiment the change was due to activation of voltage-gated $Ca^{++}$ channels.

Ion channels have been an area of intense research activity in recent years. The advantages of the present invention over the prior art will be made clear by the following comparisons.

In compound screening applications, a prior art standard, cited in the Background Section, is disclosed in U.S. Pat.

No. 5,355,215. This device, used primarily for detecting induced changes in intracellular $Ca^{2+}$, includes a dispenser to initiate transient events. The principal advantages of the present invention over this prior art are the following: 1) imaging and analysis permitting the determination of individual cellular responses as compared to a response averaged over the well, 2) increased sensitivity, requiring lower reagent loading and lower illumination intensity, and enabling smaller sample volumes, and 3) the acquisition of images at video rates compared to a maximum rate of 1 point per second.

In research applications, the system of Tsien and co-workers disclosed in the Handbook of Biological Confocal Microscopy, J. B. Pawley, ed., Plenum Press, New York, 1995, pp. 459–478, serves as a standard. It has a demonstrated capability to image at rates beyond the present invention. This cannot be accomplished, however, on samples presently of interest. The prior art requires $10^2 10^3$ greater fluorophores per pixel to achieve rates comparable to the present invention at a comparable signal-to-noise ratio. In addition, the present invention can acquire images at 12- or 16-bit resolution, giving it a 4–16× greater dynamic range.

A second example of a research system is disclosed in Sun et al., J. Physiology, 509, 67–80, 1998. According to Sun, data is generated at rates up to 650 Hz per 600-pixel line with 5 microsecond per pixel integration time, using a conventional spot scanning confocal microscope. Only one-dimensional "imaging" is performed. Transients can be monitored for objects lying along the scanned line. In addition, this rate could only be achieved with 1-$\mu$s pixel integration time, requiring a 102–103 greater concentration of fluorophores to achieve image quality comparable to the present invention.

The capabilities of the present invention to image and analyze changes in intra-cellular ion concentrations in response to external stimuli has multiple applications in compound screening and in general biological research applications. (See e.g. J. Cell Biol. 137(3), 633–648 (1997); J. Biol. Chem. 271(9), 4999–5006 (1996); Science 280, 69–76 (1998); Biochem, J., 324, 645–651 (1997)). A wide variety of fluorescent indicators are available sensitive to specific ions (see Haugland R. P. Handbook of Fluorescent Probes and Research Chemicals, $6^{th}$ Ed. Chaps 18, 22 and 24). These indicators allow measurement of concentrations of $Mg^{2+}$, $Zn^{2+}$, $Ca^{2+}$, $Na^+$, $Fe^{2+}$ $Hg^{2+}$, $Pb^{2+}$, $Cd^{2+}$, $Ni^{2+}$, $Co^{2+}$ $Al^{3+}$, $Ga^{3+}$, $Eu^{3+}$, $Tb^{3+}$, $Tb^{3+}$, $Sm^{3+}$, and $Dy^{3+}$. In addition, assays for Na+and K+can be performed even in the presence of physiological concentrations of other monovalent cations (see J. Biol. Chem. 264, 19449 (1989)), including assays of $Na^+$ levels or $Na^+$ efflux in a variety of cells such as blood, brain and muscle cells (see J. biol. Chem. 268, 18640 (1993); J. Neurosci. 14, 2464 (1994); Am J. Physiol. 267, H568 (1994)), and changes in $K^+$ in sperm cells, nerve terminals synaptosomes and lymphocytes. In addition, the present invention can be used to assay $Cl^-$ concentrations in vesicles, liposomes and live cells (see Am. J. Physiol. 259, c375 (1990).

In addition, the present invention can be used to assay changes in membrane potential in cells and sub-cellular organelles. The ability to rapidly image changes in membrane potential is vital to assays for cell and organelle viability, nerve-impulse generation, muscle contraction, cell signaling and ion-channel gating (see Biophys J. 67, 208 (1994); Neuron 13, 1187 (1994); J. Membrane Biol. 130,1 (1992)). Fluorescent indicators are available that respond to fast (millisecond) potential changes in excitable cells such as neurons, cardiac cells and intact brain cells. (See Haugland R. P. Handbook of Fluorescent probes and Research Chemicals, $6^{th}$ Ed. Chap. 25). The fluorescent probes that respond to fast transmembrane potential changes typically show only a 2–10% change in fluorescence per 100 mv. The plasma membrane of a cell has a transmembrane potential of approximately −70 mv and some organelles such as mitochondria maintain transmembrane potentials of −150 mV. Thus, assays involving such rapid changes require the high sensitivity, rapid data acquisition ability common to the various embodiments of the present invention.

FRET-BASED MEASUREMENTS

The present invention can be advantageously used to perform assays which involve fluorescence resonance energy transfer (FRET). FRET occurs when one fluorophore, the donor, absorbs a photon and transfers the absorbed energy non-radiatively to another fluorophore, the acceptor. The acceptor then emits the energy at its characteristic wavelength. The donor and acceptor molecules must be in close proximity, less than approximately 10 nm, for efficient energy transfer to occur (see Methods Enzymol. 211, 353–388 (1992); Methods Enzymol. 246, 300–334 (1995)). The proximity requirement can be used to construct assays sensitive to small separations between the donor-acceptor pair. FRET typically requires a single excitation wavelength and two emission wavelengths, and an analysis consisting of the ratio of the donor and acceptor emission intensities. FRET donor acceptor pairs can be constructed for both bead-based assays and cell-based assays. Several green fluorescent protein (GFP) mutants displaying enhanced fluorescence and altered emission wavelengths can be paired for FRET cell-based assays by fusing the GFP FRET donor to one protein and the GFP FRET acceptor to either the same protein or to another protein expressed within the same cell. Such FRET pairing can be used to measure intramolecular changes, such as $Ca^{2+}$-calmodulin binding of $Ca^{2+}$ or intermolecular interactions, such as receptor dimerization. The Kinetic Imaging algorithm disclosed above can be preferentially used.

TRANSIENT TRANSFECTION

Among the significant advantages of an image-based measurement is the opportunity both to observe rare events, lost within the average, and to normalize the primary response on an object-by-object basis to a secondary, response. Both features can be important in assays using a cell line having a transiently transfected target. Gene expression and subsequent protein production following transfection is often inefficient and transient (see BioTechniques 24:478–482 (1998)). Methods to monitor the transfection efficiency that can be advantageously used with the present invention are known in the art. For example, the gene of interest can be transfected together with the gene for green fluorescent protein (GFP), so that the two proteins will be expressed either as a fusion or as separate entities. The present invention can be used to measure the amount of indicator present at one wavelength and the response associated with the target at another. The former signal can be used to normalize the response of the latter for the amount of target present. This allows the present invention to perform assays on targets too unstable to be used in currently available screening and to monitor transfection efficiencies of only a few percent. The Kinetic Imaging algorithm disclosed above can be used to analyze such data, where only one image frame is required. Viral infection of cells can be monitored, either directly through expression of viral proteins, or indirectly by acquisition of a new phenotype, even if only a few percent of cells are infected. Finally, this invention provides a method for detecting a rare event, such as the acquisition of a new phenotype by an individual cell or group of cells due to the transfection of a specific cDNA as a result of the transfection of the entire cell population with a library of diverse cDNAs.

ENZYME ASSAYS

The present invention can also be used to conduct general assays of enzyme activity. Exemplary intracellular enzymes include but are not limited to: carbonic anhydrase, guanine nucleotide-binding proteins (G proteins), adenyl cyclase, calmodulin, PI, PIP and PIP2 kinases, cAMP kinase and cAMP hydrolase, cytochrome P-450, serine/threonine protein kinases, tyrosine protein kinases, protein phosphatases, β-lactamase, β-galactosidase, dihydrofolate reductase, phosphodiesterases, caspases, proteosome proteases, nitric oxide synthase, thymidine kinase, nucleoside deaminase, glutathione-S-transferase, lipoxygenases, and phospholipases.

FIGS. 17(a)–17(d) depict the steps of a first embodiment of an enzyme assay according to the present invention. In FIG. 17(a), beads 310 with a known quantity of fluorescent-labeled peptides 312 attached thereto are added to a well 320 containing a liquid 330. Beads 310 have a density such that they sink to the bottom of the well. In FIG. 17(b), a test compound 314 is added to the well. In FIG. 17(c), enzymes 316 are added to the well. The order of the steps depicted in FIGS. 17(a), 17(b) and 17(c) is interchangeable except that at no time should the well contain the peptides and enzymes without the test compound. If not inhibited, enzymes 316 will cleave peptides 312, and the fluorescent labels will diffuse into the liquid. If, on the other hand, test compound 314 inhibits enzymes 316, typically by blocking the enzyme active sites, enzymes 316 will not cleave the fluorescent labels. In FIG. 17(d), the fluorescent labels still attached to the beads are imaged using, for example, a line-scan confocal microscope schematically depicted as element 340. From this image, the activity of test compound 314 can be determined.

In an alternative embodiment of the assay depicted in FIGS. 17(a)–17(d), the activity of the test compound can be determined by comparing the image obtained in FIG. 17(d) to the image obtained by imaging the fluorescence of the fluorescent labels in FIGS. 17(a) or 17(b) or the image of a control well.

FIGS. 18(a)–18(d) depict the steps of a second embodiment of an enzyme assay according to the present invention. In FIG. 18(a), a known quantity of fluorescent-labeled peptides 352 are attached to the bottom 362 of a well 360. In FIG. 18(b), a test compound 354 is added to the well. In FIG. 18(c), enzymes 356 are added to the well. In FIG. 18(d), the fluorescent labels still attached to the bottom of the well are imaged using, for example, a line-scan confocal microscope schematically depicted as element 380 to determine the activity of test compound 354.

In an alternative embodiment of the assay depicted in FIGS. 18(a)–18(d), the activity of the test compound can be determined by comparing the image obtained in FIG. 18(d) to the image obtained by imaging the fluorescence of the fluorescent labels in FIGS. 18(a) or 18(b) or the image of a control well.

Another example of an assay that may be performed according to the present invention is a tyrosine kinase assay. Tyrosine kinases phosphorylate tyrosine residues of substrate peptides. The substrate peptide has both a tyrosine residue and a fluorescent tag. In this assay, an antibody that at one end is selective for phosphorylated tyrosine is bound at the other end to a surface such as a bead or the bottom of a well. Tyrosine kinase and a fluorescent-tagged peptide with a tyrosine residue are added to the well. If the tyrosine kinase phosphorylates the peptide, the phosphorylated tyrosine will bind to the antibody, thereby localizing the fluorescent tag on the surface to which the antibody is attached. If the tyrosine kinase does not phosphorylate the peptide, the fluorescent tags on the peptides will be dispersed throughout the well. The extent of phosphorylation of the peptide can be determined by measuring the fluorescence adjacent to the surface. Such an assay can also be conducted where an antibody is used that is specific to the fluorescent product produced by the action of the enzyme upon the fluorescent substrate.

In addition, live-cell enzyme assays can be performed according to the present invention. A number of techniques for investigating enzymatic activity in live cells are known in the art (See Biochem. Histochem 70,243 (1995), J. Fluorescence 3, 119 (1993)) as are substrates that yield fluorescent products when acted on by enzymes (See Haugland R. P. Handbook of Fluorescent Probes and Research Chemical $6^{th}$ Ed. Chap. 10). In general, these assays use probes that passively enter the cell and are subsequently processed by intracellular enzymes to generate products retained within the cell. Other substrates yield insoluble fluorescent products that precipitate at the site of enzymatic activity. The present invention can assay the degree of enzymatic activity and determine the precise spatial localization of the enzymatic activity using such probes. Probes are available for assaying a wide variety of enzymes using the present invention including but not limited to phosphatases, ATPases, 5'-nucleotidase, DNA and RNA polymerases, peptidases, proteases, esterases and peroxidase.

Enzyme activity assays can be performed according either the first or second experimental embodiments and the associated image analysis protocols disclosed above.

MORPHOLOGY

The methods of the present invention can also be used to perform assays that require a determination of cellular or sub-cellular morphology, including but not limited to axons and organelles. To perform such assays, a fluorescent probe is introduced into the structure of interest, such as a cell or organelle, by direct micro-injection or by contacting cells with cell-permeant reagents that are metabolized or otherwise altered so as to be retained in the structure of interest. If it is to be used with live cells, the fluorescent label must be non-toxic and biologically inert. Many appropriate dyes are available commercially (See Haugland R. P. Handbook of Fluorescent Probes and Research Chemicals $6^{th}$ Ed. Chap. 15) for use in assays, for example, involving flow in capillaries, neuronal cell connectivity, translocation of dye through gap junctions, cell division and cell lysis and liposome fusion. In addition, these tracers can be used to track movement of labeled cells in culture, tissues or intact organisms. Many techniques employing fluorescent tracers to assay cell or subcellular morphology or movement are known in the art and may involve use of membrane tracers, biotinylated dextran conjugators, fluorescent microspheres or proteins and protein conjugates (See Meth. Cell Biol. 29, 153 (1989); Cytometry 21.230 (1995); Cell 84, 381 (1996); Biochem. Biophys. Acta 988, 319 (1989); Cytometry 14, 747 (1993). The various embodiments of the present invention have significant advantages when used in these types of assays. The present invention allows rapid imaging of multiple parameters with very fine spatial resolution.

NUCLEIC ACIDS

The present invention can also be used to conduct assays of nucleic acids. A specific DNA assay that would benefit from the spatial resolution and multi-wavelength imaging capability of the present invention is fluorescence-in-situ hybridization (FISH). FISH is an important technique for localizing and determining the relative abundance of specific nucleic acid sequences in cells, tissue, interphase nuclei and metaphase chromosomes and is used in clinical diagnostics and gene mapping (see Histohem J. 27, 4 (1995); Science 247, 64 (1990); Trends Genet. 9, 71 (1993) and Science 250, 559 (1990)). A variety of fluorescent hybridization probes are available for multicolor fluorescent DNA and RNA hybridization techniques (see Haugland R. P. Handbook of Fluorescent Probes and Research Chemicals, $6^{th}$ Ed. Chap. 8.4). An additional technique determines chromosome banding by the use of an AT or GC selective DNA-dyes with a nucleic acid counter stain. This technique is widely used for karotype analysis and chromosome structure studies (see Human Genet. 57,1 (1981)).

REACTIVE OXYGEN SPECIES

The present invention can also be used to assay levels of various reactive oxygen species such as singlet oxygen, superoxides and nitric oxide. The importance of these reactive oxygen species has only recently been realized (See Biochem Pharmacol 47,373 (1994), J. Cell Biol. 126, 901 (1994)). It is now known that singlet oxygen is responsible for much of the physiological damage caused by reactive oxygen species (See J. Photochem. Photobiol. 11,241 (1991)). Nitric Oxide (NO), in particular, is now known to play a critical role as a molecular mediator in a variety of physiological processes including neurotransmission and blood-pressure regulation (See Current Biology 2,437 (1995), J. Med. Chem. 38,4343 (1995), Cell 78, 919 (1994)). Techniques are known in the art to perform assays to measure NO indirectly. For example, under physiological conditions, NO is oxidized to nitrite and this can be detected by monitoring absorbance at 548 nm or by use of a probe which reacts with nitrite to form an identifiable fluorescent product. (See Haugland R. P., Handbook of Fluorescent Probes and Research Chemicals $6^{th}$ Ed. Chap. 21).

pH

The present invention can also be used to perform assays involving measurements of pH changes within cells or in cell-free media. The importance of the role of intracellular pH has been recognized in many diverse physiological and pathological processes including cell proliferation, apoptosis, fertilization, malignancy, multi-drug resistance, ion transport, lysosomal storage disorders and Alzheimer's disease. (See Cell Physiol. Biochem. 2, 159 (1992); J. Biol. Chem. 270, 6235 (1995); Biophys. J. 68, 739 (1995); J. Biol. Chem. 270, 19599 (1995); Cancer Res. 54, 5670 (1994)). Fluorescent probes useful for assays of pH in the physiological range are available commercially (See Haugland R. P., Handbook of Fluorescent Probes and Research Chemicals $6^{th}$ Ed. Chap. 23).

EXAMPLES

The invention described and claimed herein can be further appreciated by one skilled in the art through reference to the examples which follow. These examples are provided merely to illustrate several aspects of the invention and shall not be construed to limit the invention in any way.

Transcription Factor Translocation

Cells were grown in 96-well plates, fixed, incubated with Texas-Red-labeled antibody to the transcription factor protein, rinsed, and then stained with 5 $\mu$M Hoechst 33342 in buffer.

The images in FIG. 19 are 0.5×0.5 $mm^2$ square with 1.08×1.08 $\mu m^2$ pixelation. Texas Red emission was excited at 568 nm and detected with a 600-nm long pass filter. Hoechst emission was excited at 364 nm and detected with a 420–480-nm bandpass filter. Image acquisition time was 0.9 sec. There are ~150 cells per image FIG. 19a) is an image of a field of cells which were not activated before fixing. The Texas Red intensity in the nucleus is low compared to the cytoplasm. FIG. 19b) is the composite of the images in FIG. 19a) and that due to the Hoechst 33342 emission.

Figure 19A:
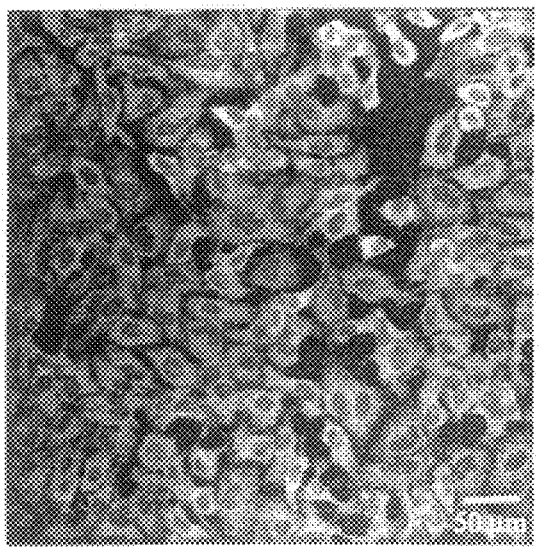
FIGS. 19(a)–19(d) show a transcription factor translocation assay.
Figure 19B:
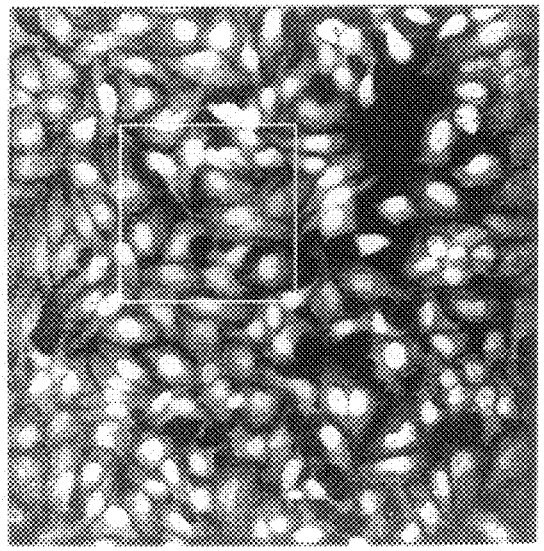
Figure 19C:
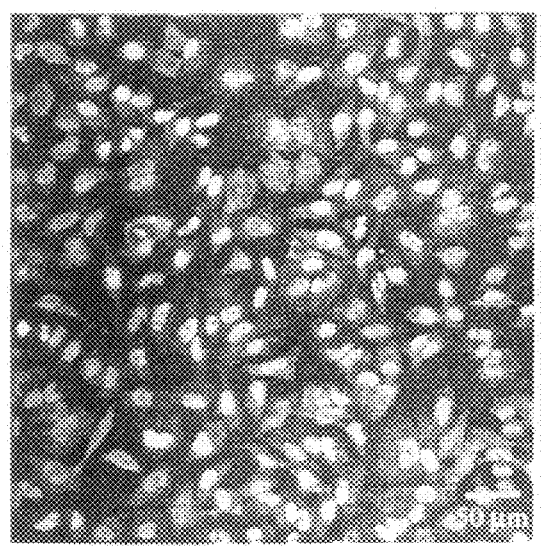
Figure 19D:
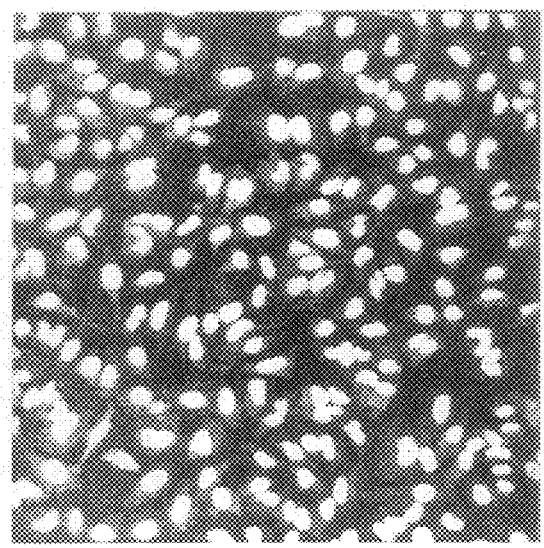
Figure 20A:
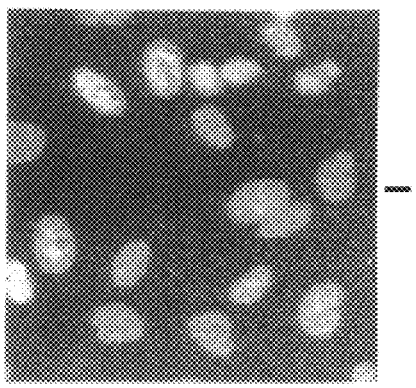
FIGS. 20(a)–20(d) show a translocation assay data analysis.
Figure 20B:
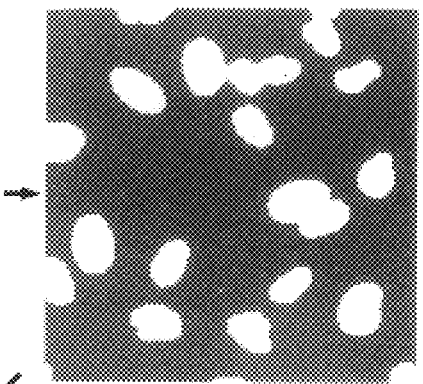
Figure 20C:
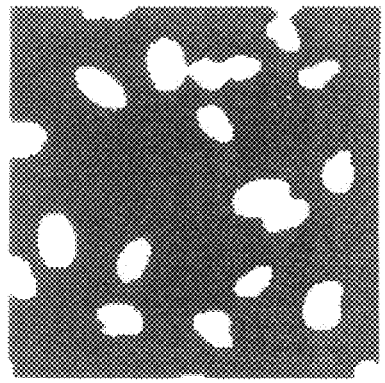
Figure 20D:
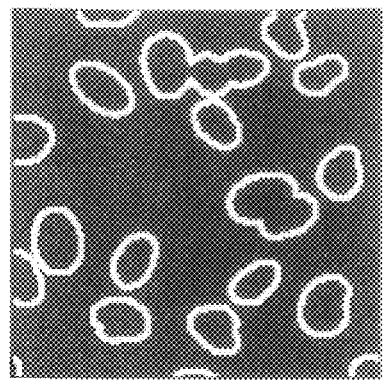
Figure 21A:
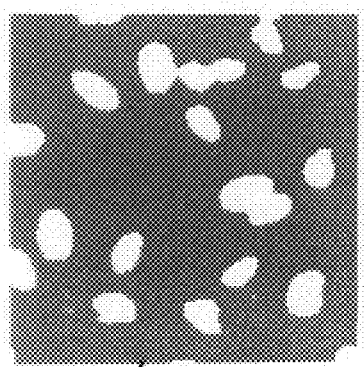
FIGS. 21(a)–21(e) show another data analysis.
Figure 21B:
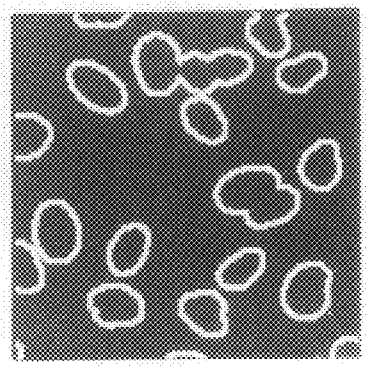
Figure 21C:
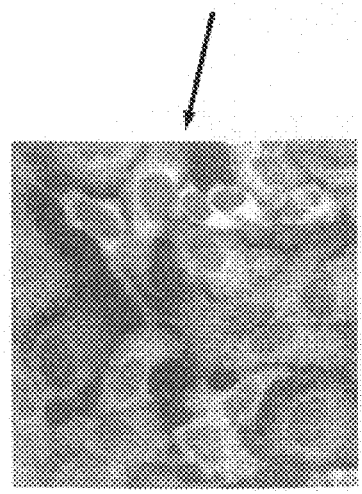
Figure 21D:
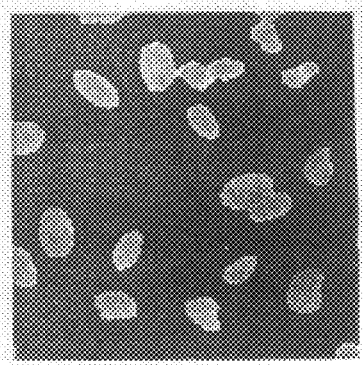
Figure 21E:
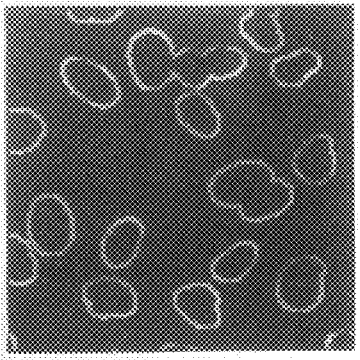
Figure 22A:
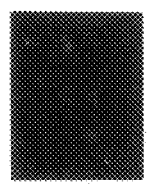
FIG. 22 shows neuroblastoma cell calcium response to Carbachol.
Figure 22B:
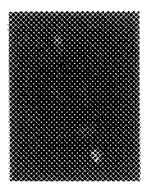
Figure 22C:
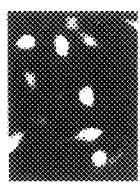
Figure 22D:
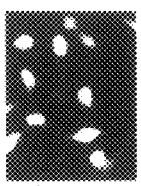
Figure 22E:
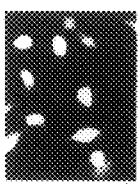
Figure 22F:
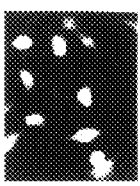
Figure 22G:
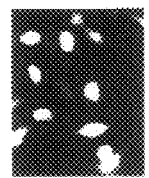
Figure 22H:
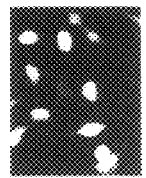
Figure 22I:
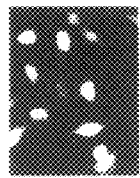
Figure 22J:
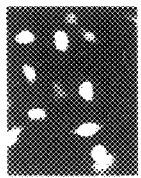
Figure 22K:
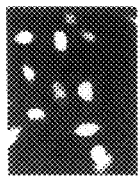
Figure 22L:
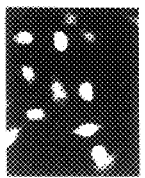
Figure 22M:
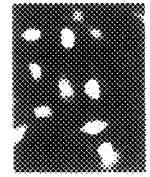
Figure 22N:
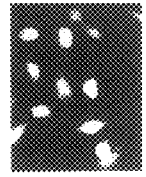
Figure 22O:
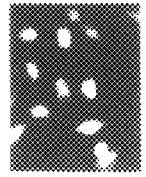
Figure 22P:
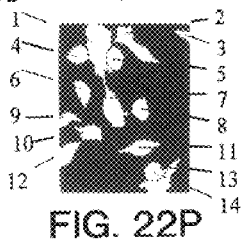
Figure 23A:
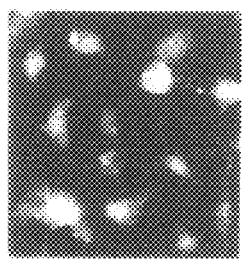
FIGS. 23(a)–23(h) show neuroblastoma cell calcium response to 50 mM KC.
Figure 23B:
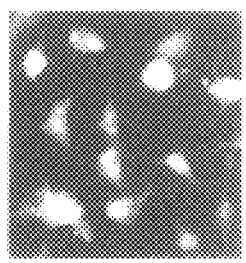
Figure 23C:
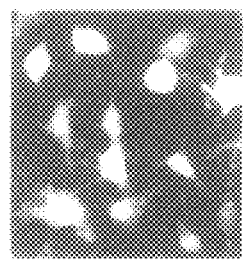
Figure 23D:
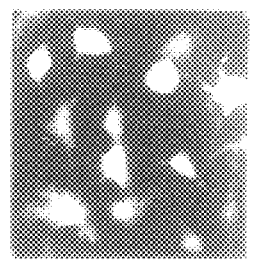
Figure 23E:
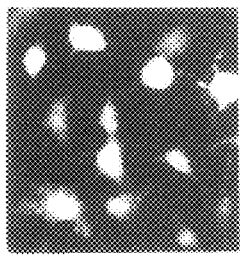
Figure 23F:
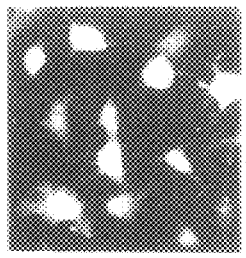
Figure 23G:
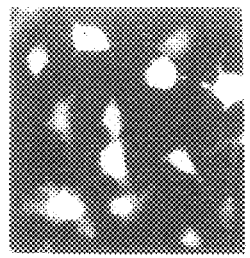
Figure 23H:
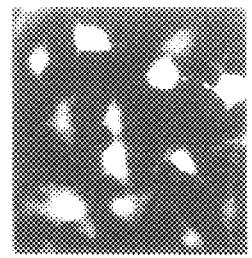

FIG. 19c) is an image of a field of cells which were activated prior to fixing. Due to color scaling, the cytoplasm is difficult to see without saturating the nucleus. FIG. 19d) is the composite of the images in FIG. 19c) and that due to the Hoechst 33342 emission from the same sample.

The data analysis was performed according to the following method. The area highlighted in FIG. 19b) is reproduced in FIG. 20 which depicts the mask generation steps. A binary representation of the Hoechst image was generated by applying an appropriate threshold, those values greater than the threshold were set to one, those less than the threshold were set to zero. This served as the primary mask. Two daughter masks were then generated, one by eroding the primary mask, the other by dilating the primary mask and subtracting the original mask to form an annular mask. The Texas-Red-emission image was multiplied by the eroded binary mask, as depicted in FIG. 21, and the pixels summed as a measure of the quantity of labeled transcription factor in the nucleus. Similarly, the Texas-Red-emission image was multiplied by the annular binary mask, as depicted in FIG. 21, and the pixels summed as a measure of the quantity of labeled transcription factor in the cytoplasm. The degree of activation is assessed using the ratio of nuclear to cytoplasmic intensity.

Figure 28A:
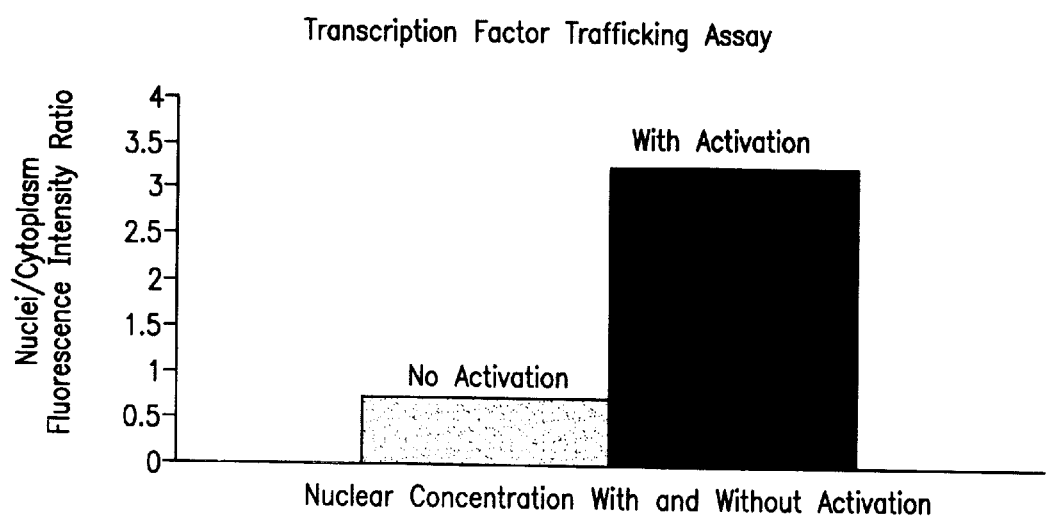
FIGS. 28(a)–28(e) how the data from the translocation assay, ion channel assay and cell surface receptor binding as graphs.

This ratio is represented in the bar graph in FIG. 28a for cells with and without activation.

Transient Ca Imaging of Muscarinic Receptor and Voltage-gated Channel Stimulation The cells in FIGS. 22 and 23 were from a neuroblastoma line. They were grown and imaged in standard media These cells express a muscarinic acetylcholine receptor that can be stimulated with Carbachol generating a large intra-cellular Ca release as a second signal. In addition the cells express a voltage-gated "L" Ca channel which can be stimulated by depolarizing the cell membrane with a large change in the external $K^+$ concentration and which can be inhibited with Verapamil.

In general, the image sequences were initiated by rapidly adding 100 $\mu$L of reagent in growth media to cells in 100 $\mu$L of growth media in a 96-well plate. The turbulence caused by the added volume generates a small distortion in cell shape. This distortion is visible as a transient alteration of the Ca fluorescence assigned to each cell in the first image frame after addition.

Figure 28B:
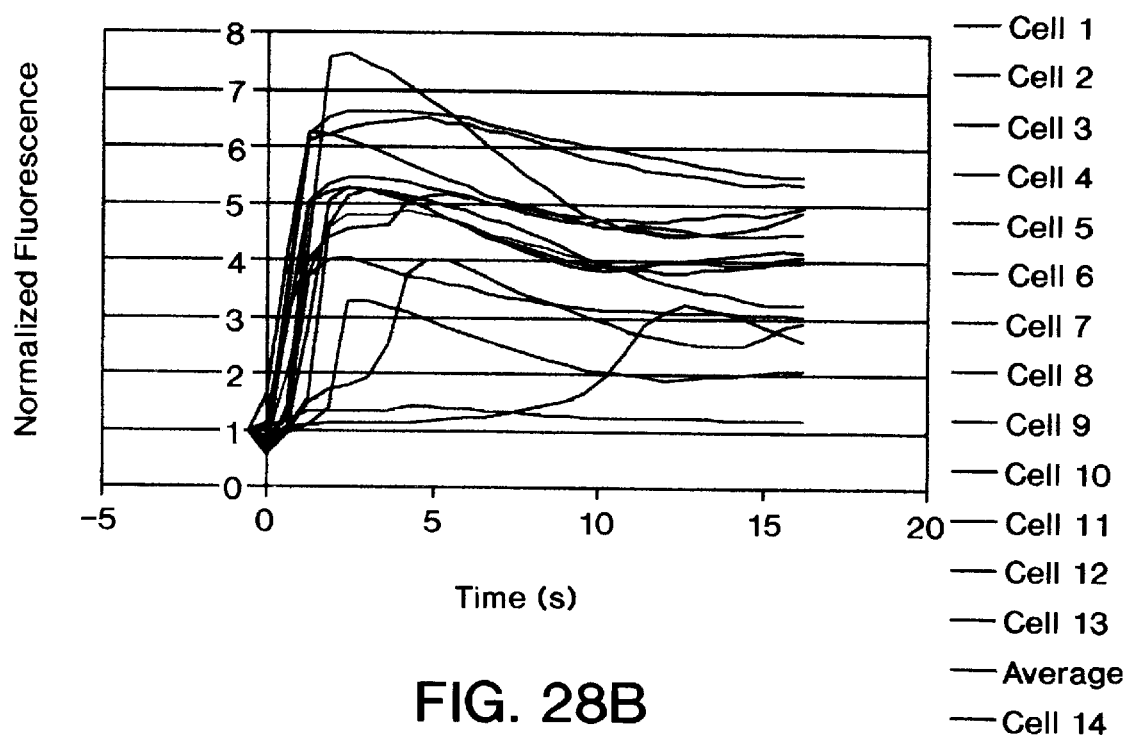

In FIG. 22 a movie with 1.2 seconds between frames is displayed. The image sequence was initiated by the rapid addition of 100 $\mu$M Carbachol. The final image is a binary mask, used to identify and enumerate fluorescent objects in the image, generated from the pre-injection frame. Even though the pre-injection image appears dim, it is quite bright. The mask is applied to each image in the series, and for each object, the integrated intensity, normalized to the pre-injection image, is plotted vs. time, as displayed in FIG. 28b. The mask was not processed for overlapping cells. For example, object 1 is likely more than one cell, but showed no response. Object 7 may be 2 overlapping cells, with one showing a delayed response.

Figure 28C:
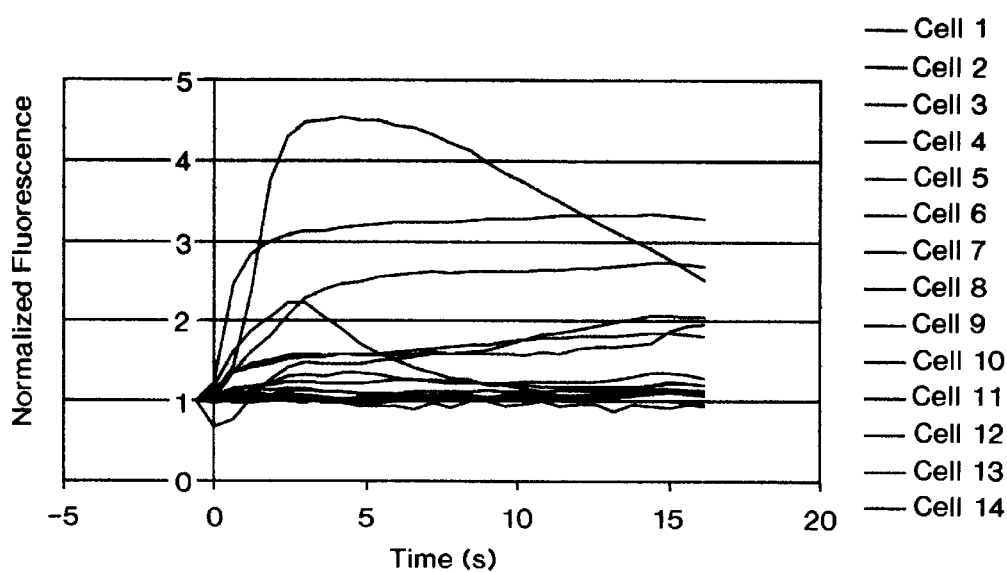
Figure 28D:
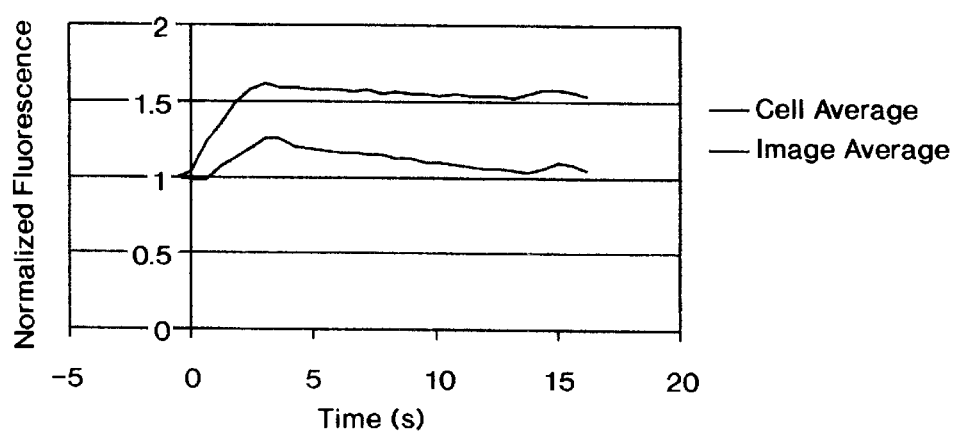

FIG. 23a–h are selected frames of a movie showing the response of the neuroblastoma cells to a depolarization event initiated by the addition of 50 mM KCl which opens the voltage-gated "L" channels. The analysis procedure was as is described above in connection to FIG. 28b. The results are displayed in FIG. 28c. Note the increased sensitivity obtained by using the "cell average" rather than the "image average".

Live-cell G-Protein Coupled Receptor Binding

The images displayed in FIGS. 24a–c to 25a–d were obtained on live cells in 96-well plates. The cells had been transfected with a G-protein coupled receptor, for which the natural peptide ligand is known. Prior to imaging, the cells were incubated with the native unlabeled ligand in normal growth media containing 10% serum for 20 minutes at 37° C., followed by 20 minutes with 20 nM fluorescein-labeled ligand and 100 nM LDS 751, also 37° C. Samples were not rinsed.

These images are (0.5×0.5) mm² are with (1.08×1.08) $\mu$m² pixelation. Fluorescein emission was excited at 488 nm and detected with a 45-nm bandpass filter centered at 535 nm. LDS 751 emission also excited at 488 nm and was detected with a 40-nm bandpass filter, centered at 690 nm. Image acquisition time was 0.9 sec. These cells have 100,000 receptors/cell or about 25 receptors/$\mu$m² of membrane surface.

Figure 24A:
FIGS. 24(a)–24(c) show homogeneous live cell receptor binding assays.
Figure 24B:
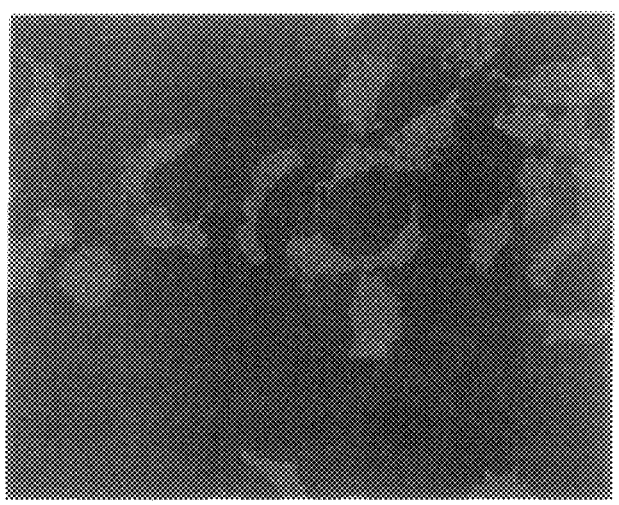
Figure 24C:
Figure 25A:
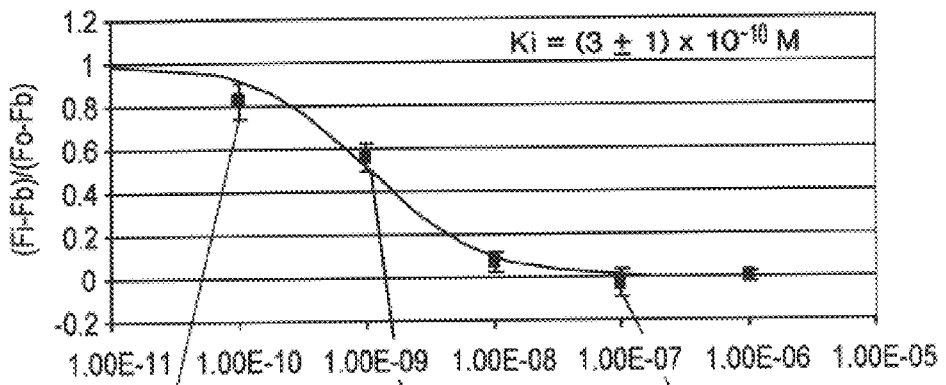
FIGS. 25(a)–25(d) show homogeneous live cell receptor binding a says.
Figure 25B:
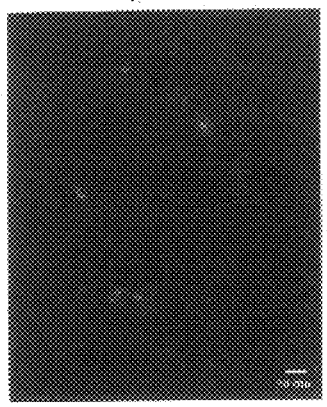
Figure 25C:
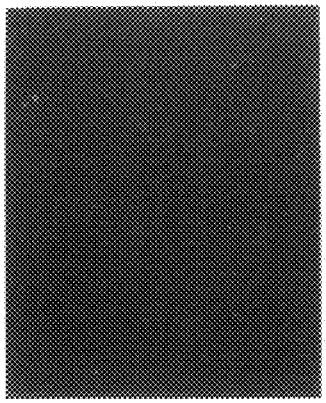
Figure 25D:
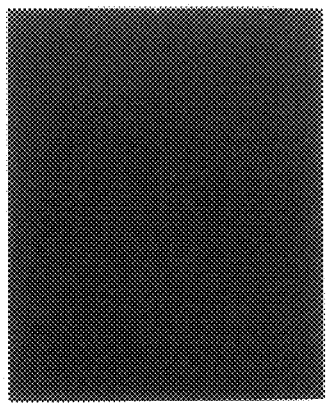

FIG. 24a is an image of the cells after incubation with the labeled ligand. No wash step was performed prior to imaging. The substantial variation in reception activity is evident. Some cells bind so little ligand that they appear as depressions in the background. A cell-by-cell analysis of the binding activity is facilitated by making a mask from an image of LDS 751 emission, a non-specific nucleic acid stain, shown in FIG. 25c. The staining is not entirely uniform, but the vast majority of cell volume is revealed. The overlay in FIG. 25d of the binary mask generated from thresholding the data in FIG. 25c with the receptor binding image yields a pseudo-color map of receptor activity. High activity is represented as yellow, while low activity is shown as orange-red.

Figure 28E:
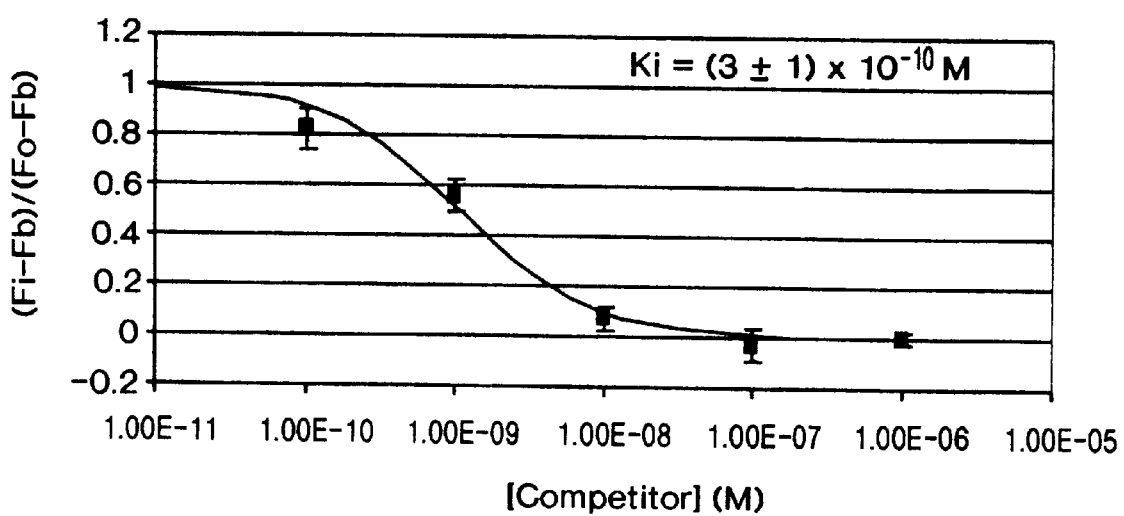

In FIG. 25 three images are displayed corresponding to points on the titration curve of the 20-nM labeled ligand with the unlabeled ligand. The curve is displayed in FIG. 28e. A $K_r = 3 \pm 1 \times 10^{10}$ M for the unlabeled ligand is calculated.

Figure 26A:
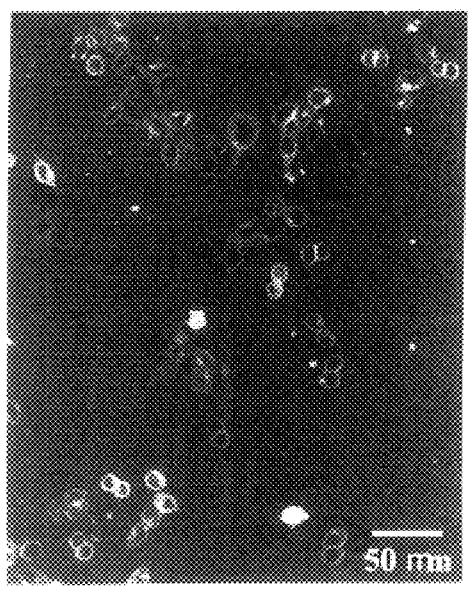
FIGS. 26(a)–26(d) show homogeneous live cell receptor binding assays with Cy3 labeled ligands.
Figure 26B:
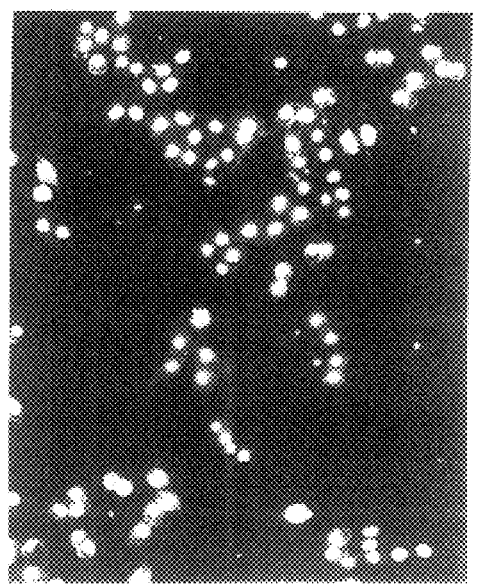
Figure 26C:
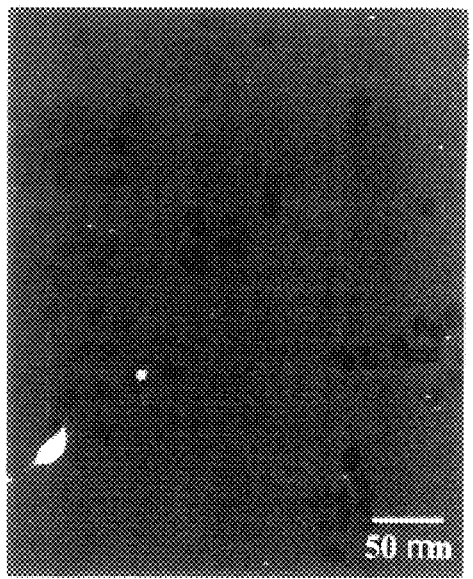
Figure 26D:
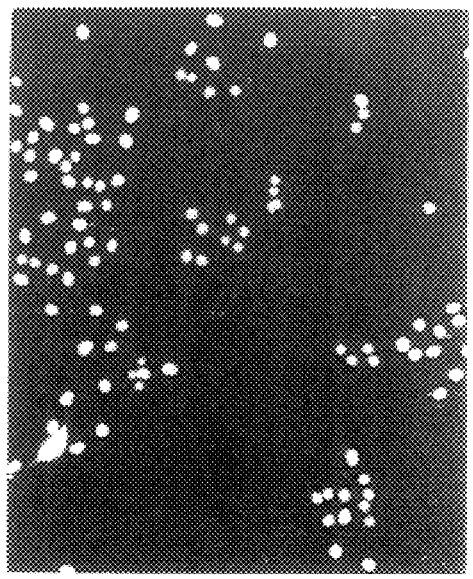
Figure 27A:
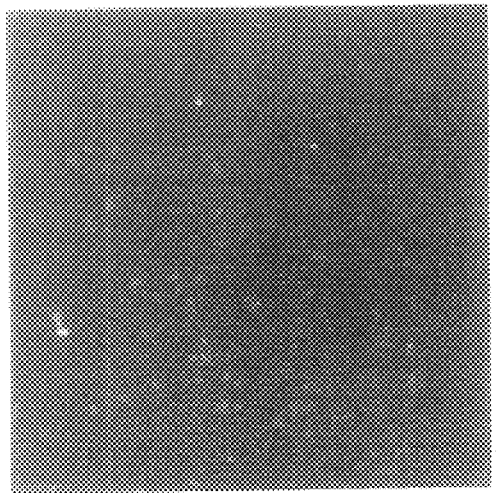
FIGS. 27(a)–27(d) show 4 µm diameter silica beads with varying numbers of Cy5 labels.
Figure 27B:
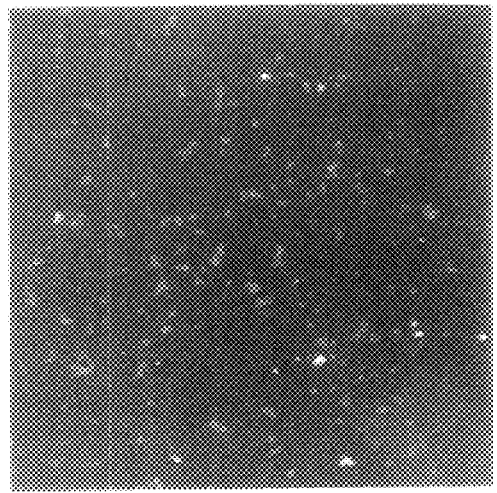
Figure 27C:
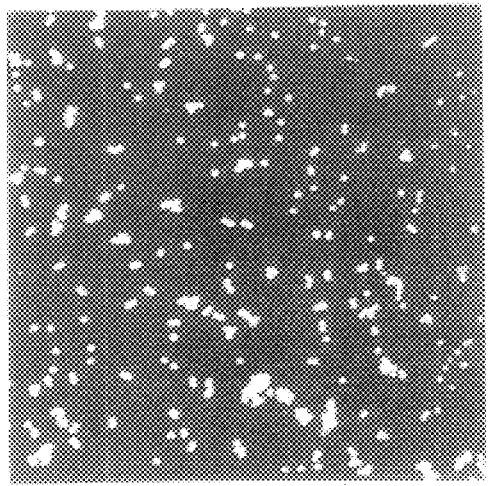
Figure 27D:
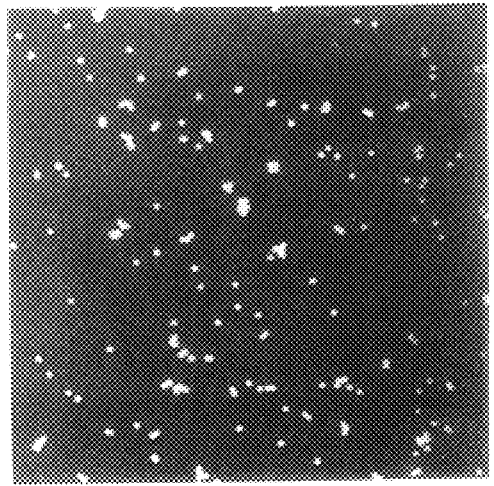

Images illustrating receptor binding on a different mammalian cell line are shown in FIGS. 26a–d. FIG. 26a is an image of the cells incubated with a 256 nM Cy3-labeled ligand. A range of binding activity is visible. FIG. 26b shows an overlay of the Cy3 data with a simultaneously acquired image of the 1-$\mu$M Hoechst 33342 stained nuclei. The latter serves as a reliable identifier of the individual cells. In FIG. 26c, the image is of the cells incubated with 256 nM Cy3-labeled ligand in the presence of 10 $\mu$M unlabeled ligand, and in FIG. 26d, this data is displayed with the image of the 1-$\mu$M Hoechst 33342 stained nuclei overlaid. The effect of displaced fluid by unlabeled cells is evident in FIG. 26c. In the high correlation between FIGS. 26c and d exemplifies the effectiveness of identifying cells by their excluded volume.

Simulated Bead-Based Receptor-Binding

In FIG. 27a–d images of Cy5-labeled silica beads are presented. The experiment is a simulation of a receptor-binding assay in which fluorescently-labeled ligands bind to membrane-bound receptors supported on microspheres.

Silica microspheres, 4 $\mu$m in diameter, were coated with polyethyleneimine and biotinylated with a biotin NHS-ester. The activity of the beads was assayed with a fluorimeter by quantifying the amount of Cy5-labeled streptavidin removed from solution by adsorption onto a known quantity of beads. Each bead was found to hold $1.3 \times 10^6$ streptavidin molecules. Beads were loaded with a known quantity of Cy5 molecules by pre-mixing an appropriate ratio of Cy5-labeled and non-labeled streptavidin and incubating with the beads. The loadings were equivalent to 0.16, 1.6 and 16 finole/200 $\mu$g of polystyrene beads. Each bead had an average of 17, 170, or 1700 labels, respectively. The samples were placed in Costar 96-well plates for imaging. Cy5 was excited with 647 nm laser light and the emitted fluorescence was detected through a 40-nm bandpass filter centered at 690 nm. The scanned images were acquired at 1-$\mu$m pixelation in approximately 0.7 seconds.

Beads loaded with 170 and 1700 molecules were readily detectable and the 17-fluor beads are discernable in images constituting FIG. 27. Beads loaded only with non-labeled streptavidin did not produce appreciable intensities.

We claim:

1. A focusing system for use with a substrate, comprising a discontinuous surface and a continuous surface extending in the same direction as the discontinuous surface, said system comprising:

a) an objective lens through which is directed a first beam of electromagnetic radiation that is to be focused on the discontinuous surface or on an object located on the discontinuous surface;

b) a second beam of electromagnetic radiation having a first wavelength, said second beam being directed through said objective lens to a focus on the discontinuous surface and reflected by said discontinuous surface back through the objective lens;

c) a third beam of electromagnetic radiation having a second wavelength, said third beam being directed through said objective lens to a focus on the continuous surface and reflected by said continuous surface back through the objective lens;

d) a means for separating the radiation of the first wavelength from the radiation of the second wavelength that is reflected back through the objective lens;

e) a first detector for detecting the second beam reflected by the discontinuous surface back through the objective lens;

f) a second detector for detecting the third beam reflected by the continuous surface back through the objective lens;

g) a moving means for moving the objective lens relative to the substrate or the substrate relative to the objective lens so as to control the focus of the beams reflected back through the objective lens; and h) a controller connected to the first and second detectors and the moving means, wherein the controller operates the moving means in response to a signal from the first detector or the second detector according to the position of the second beam or the third beam on the substrate.

2. The focusing system according to claim 1, wherein the first and second wavelengths are the same.

3. The focusing system according to claim 1, wherein the controller comprises a computer.

4. The focusing system according to claim 1, wherein the substrate is a microtiter plate.

5. The focusing system according to claim 1, wherein the discontinuous surface is a bottom of a well in a microtiter plate.

6. A focusing system for use with a substrate comprising a discontinuous surface and a continuous surface extending in the same direction as the discontinuous surface, wherein the substrate is a microtiter plate and the discontinuous surface is a bottom of a well in the microtiter plate, said system comprising:
   a) an objective lens through which is directed a first beam of electromagnetic radiation that is to be focused on the discontinuous surface or on an object located on the discontinuous surface;
   b) a second beam of electromagnetic radiation directed through the objective lens to a focus on the discontinuous surface and reflected by said discontinuous surface back through the objective lens;
   c) a focus detector for detecting the second beam reflected by the discontinuous surface back through the objective lens;
   d) a moving means for moving the objective lens relative to the substrate or the substrate relative to the objective lens so as to control the focus of the second beam reflected back through the objective lens; and
   e) a controller connected to the focus detector and the moving means, wherein the controller operates the moving means in response to a signal from the focus detector according to the position of the second beam on the substrate.

7. The focusing system of claim 6, wherein the controller comprises a computer.

8. A focusing system for use with a substrate comprising a discontinuous surface and a continuous surface extending in the same direction as the discontinuous surface, said system comprising:
   a) an objective lens through which is directed a first beam of electromagnetic radiation that is to be focused on the discontinuous surface or on an object located on the discontinuous surface;
   b) a second beam of electromagnetic radiation having a first polarization state, said second beam being directed through the objective lens to a focus on the discontinuous surface and reflected by said discontinuous surface back through the objective lens;
   c) a third beam of electromagnetic radiation having a second polarization state, said third beam being directed through said objective lens to a focus on the continuous surface and reflected by said continuous surface back through the objective lens;
   d) a means for separating the polarization state of the second beam from the polarization state of the third beam, wherein the second and third beams are reflected back through the objective lens;
   e) a first detector for detecting the second beam reflected by the discontinuous surface back through the objective lens;
   f) a second detector for detecting the third beam reflected by the continuous surface back through the objective lens;
   g) a moving means for moving the objective lens relative to the substrate or the substrate relative to the objective lens so as to control the focus of the beams reflected back through the objective lens; and
   h) a controller connected to the first and second detectors and the moving means, wherein the controller operates the moving means in response to a signal from the first detector or the second detector according to the position of the second beam or the third beam on the substrate.

9. The system of claim 8, wherein the second beam and the third beam are from the same source of electromagnetic radiation.

10. The system of claim 8, wherein the second beam and the third beam have the same wavelengths.

11. The system of claim 8, wherein the means for separating the polarization state comprises a polarizing beamsplitter.

12. The system of claim 8, wherein the controller comprises a computer.

13. The system of claim 8, wherein the substrate is a microtiter plate.

14. The system of claim 8, wherein the discontinuous surface is a bottom of a well in a microtiter plate.

15. The system of claim 8, wherein the first polarization state and the second polarization state are perpendicular.

16. A method for focusing onto a substrate comprising a discontinuous surface and a continuous surface extending in the same direction as the discontinuous surface, comprising:
   a) focusing a first beam of electromagnetic radiation on the discontinuous surface or on an object located on the discontinuous surface through an objective lens;
   b) focusing a second beam of electromagnetic radiation having a first wavelength through the objective lens onto the discontinuous surface, and directing the reflection of said second beam by said discontinuous surface back through the objective lens;
   c) focusing a third beam of electromagnetic radiation having a second wavelength through the objective lens onto the continuous surface, and directing the reflection of said third beam by said continuous surface back through the objective lens;
   d) separating the radiation of the first wavelength from the radiation of the second wavelength that is reflected back through the objective lens;
   e) detecting the reflected second beam;
   f) detecting the reflected third beam;
   g) moving the objective lens relative to the substrate or the substrate relative to the objective lens so as to control the focus of the beams reflected back through the objective lens; and
   h) controlling the movement in step g in response to a signal generated from detecting the reflected second beam or the reflected third beam according to the position of the second beam or the third beam on the substrate.

17. The method of claim 16, wherein the controlling is performed by a computer.

18. The method of claim 16, wherein the substrate is a microtiter plate.

19. The method of claim 16, wherein the discontinuous surface is a bottom of a well in a microtiter plate.

20. A method for focusing onto a substrate comprising a discontinuous surface and a continuous surface extending in the same direction as the discontinuous surface, wherein the substrate is a microtiter plate and the discontinuous surface is a bottom of a well in the microtiter plate, comprising:
   a) focusing a first beam of electromagnetic radiation on the discontinuous surface or on an object located on the discontinuous surface through an objective lens;

b) focusing a second beam of electromagnetic radiation through the objective lens to the discontinuous surface and directing the reflection the second beam by said discontinuous surface back through the objective lens;

c) detecting the second beam reflected by the discontinuous surface back through the objective lens;

d) moving the objective lens relative to the substrate or the substrate relative to the objective lens so as to control the focus of the second beam reflected back through the objective lens; and e) controlling the movement in step d in response to a signal generated from detecting the reflected second beam according to the position of the second beam on the substrate.

21. The method of claim 20, wherein the controlling is performed by a computer.

22. A method for focusing onto a substrate comprising a discontinuous surface and a continuous surface extending in the same direction as the discontinuous surface, comprising:

a) focusing a first beam of electromagnetic radiation on the discontinuous surface or on an object located on the discontinuous surface through an objective lens;

b) focusing a second beam of electromagnetic radiation having a first polarization state through an objective lens and directing the reflection of said second beam by the discontinuous surface back through the objective lens;

c) focusing a third beam of electromagnetic radiation having a second polarization state on the continuous surface, and directing the reflection of said third beam by said continuous surface back through the objective lens;

d) separating the polarization state of the second beam from the polarization state of the third beam;

e) detecting the reflected second beam;

f) detecting the reflected third beam;

g) moving the objective lens relative to the substrate or the substrate relative to the objective lens so as to control the focus of the beams reflected hack through the objective lens; and h) controlling the movement in step g in response to a signal generated from detecting the reflected second beam or the reflected third beam according to the position of the second beam or the third beam on the substrate.

23. The method of claim 22, wherein the second beam and the third beam are formed using the same source of electromagnetic radiation.

24. The method of claim 22, wherein the second beam and the third beam have the same wavelengths.

25. The method of claim 22, wherein the separating of the polarization state is performed by a polarizing beamsplitter.

26. The method of claim 22, wherein the controlling is performed by a computer.

27. The method of claim 22, wherein the substrate is a microtiter plate.

28. The system of claim 22, wherein the discontinuous surface is a bottom of a well in a microtiter plate.

29. The system of claim 22, wherein the first polarization state and the second polarization state are perpendicular.

* * * * *